(12) United States Patent
Kem et al.

(10) Patent No.: US 8,592,458 B2
(45) Date of Patent: *Nov. 26, 2013

(54) ALPHA7 NICOTINIC RECEPTOR SELECTIVE LIGANDS

(75) Inventors: William Reade Kem, Gainesville, FL (US); Ferenc Soti, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/328,841

(22) Filed: Dec. 16, 2011

(65) Prior Publication Data

US 2012/0094943 A1     Apr. 19, 2012

Related U.S. Application Data

(63) Continuation of application No. 11/921,832, filed as application No. PCT/US2006/022136 on Jun. 7, 2006, now Pat. No. 8,093,269.

(60) Provisional application No. 60/688,216, filed on Jun. 7, 2005.

(51) Int. Cl.
*C07D 401/14* (2006.01)
*A61K 31/44* (2006.01)

(52) U.S. Cl.
USPC ............ 514/333; 514/334; 546/256; 546/257

(58) Field of Classification Search
None
See application file for complete search history.

(56) References Cited

U.S. PATENT DOCUMENTS

| 5,741,802 | A | 4/1998 | Kem et al. |
| 5,977,144 | A | 11/1999 | Meyer et al. |
| 7,244,745 | B2 | 7/2007 | Herbert et al. |
| 8,093,269 | B2 * | 1/2012 | Kem et al. ..................... 514/333 |
| 2007/0232651 | A1 | 10/2007 | Habgood et al. |

FOREIGN PATENT DOCUMENTS

WO    WO-2004/019943 A    3/2004

OTHER PUBLICATIONS

West, Anthony R., Solid State Chemistry and its Applications, Wiley, New York, 1988, pp. 358 & 365.*
Wu et al, Toxicology, vol. 236, 2007, pp. 1-6.*
Arendash. G.W. Brain Research. 1995, vol. 674. No. 2, pp. 252-259, see especially p. 253, 2nd column.
de Fiebre CM, et al. Characterization of a series of anabaseine-derived compounds reveals that the 3-(4)-dimethylaminocinnamylidine derivative is a selective agonist at neuronal nicotinic alpha 7/125I-alpha-bungarotoxin receptor subtypes. Mol Pharmacol. Jan. 1995;47(1):164-71.
Kem et. al., Mol. Pharmacol. 2004, vol. 65. No. 1, pp. 56-67.
Kem, Behav. Brain Res. 2000, vol. 113, pp. 169-181.
Papke et al., Br. J. Pharmacol. 2002, vol. 137, pp. 49-61.
Stokes et al., Mol. Pharmacol. 2004, vol. 66. No. 1, pp. 14-24.

* cited by examiner

*Primary Examiner* — Zinna Northington Davis
(74) *Attorney, Agent, or Firm* — Edwards Wildman Palmer LLP; Jeffrey D. Hsi; Peter F. Corless

(57) ABSTRACT

The invention relates to the design and synthesis of 3-arylidene-anabaseine compounds that exhibit enhanced selectivity toward alpha7 nicotinic receptors. The compounds are expected to be useful in treating a wide variety of conditions, including neurodegenerative conditions such as Alzheimer's Disease, neurodevelopmental diseases such as schizophrenia, and certain peripherally located inflammations mediated by macrophage infiltration.

37 Claims, No Drawings

ALPHA7 NICOTINIC RECEPTOR SELECTIVE LIGANDS

CROSS-REFERENCE TO RELATED APPLICATIONS

The present application is a Continuation of U.S. patent application Ser. No. 11/921,832, filed Feb. 17, 2009, now U.S. Pat. No. 8,093,269, which is a U.S. national phase application, pursuant to 35 U.S.C. §371, of PCT International Application Ser. No. PCT/US2006/022136, filed Jun. 7, 2006, designating the United States and published in English on Dec. 14, 2006 as publication WO 2006/133303 A1, which claims priority under 35 I/S/C/ §119(e) to U.S. Provisional Application 60/688,216, filed Jun. 7, 2005, each of which are hereby incorporated by reference in its entirety.

STATEMENT AS TO FEDERALLY SPONSORED RESEARCH

This invention was made with U.S. government support under grant number MH-61412 awarded by the National Institutes of Health. The U.S. government may have certain rights in the invention.

BACKGROUND OF THE INVENTION

Several types of nicotinic acetylcholine receptors (nAChRs) are known to play a role in central nervous system activity and as such are involved in cognition, mood and neuroprotection. The various types of known nicotinic ligands appear to have different combinations of effects on nicotine-modulated functions, depending on the subtypes of nAChRs affected, some affecting all receptors, others having more selective actions. A multitude of compounds has been investigated, including quinuclidines (AR17776 and congeners); azabicycyclic compounds for treating dementia (U.S. Pat. No. 5,217,975); 2-aroylaminothiazole derivatives that may be useful for treating cognitive disorders (U.S. Pat. No. 5,510,478); and 5-hydroxytryptophan receptor antagonists based on 1-azabicyclo nonane derivatives (U.S. Pat. No. 4,798,829). Published U.S. application (2004/0087616) discloses 1H-pyrazole and 1H-pyrrole-azabicyclic compounds reported to have alpha7 ($\alpha$7) nicotinic acetylcholine receptor agonist activity which may be useful in treating the cognitive and attention deficit symptoms of Alzheimer's disease (AD) and other degenerative CNS conditions.

A large number of 3-arylidene-anabaseine compounds have been prepared (WO 2004/019943) for potential use in treating neurodegenerative diseases, and particularly with the hope that some compounds would bind to nicotinic alpha7 receptors. No particular nicotinic receptor activity (agonist or antagonist) or nicotinic receptor subtype selectivity has been demonstrated for any of these anabaseine analogs, all of which contain fused-ring heteroaromatic moieties attached through a methylene group to the 3-position of anabaseine without substitutions on the tetrahydropyridyl ring in the anabaseine molecule.

Acetylcholine receptors can be divided into muscarinic (mAChR) and nicotinic (nAChR) subtypes in the mammalian central nervous system (CNS). These subtypes are distinguished based on their ability to be stimulated by either the mushroom toxin muscarine or the plant alkaloid nicotine. Nicotinic receptors are important in cholinergic transmission in autonomic ganglia, striated muscles, the neuromuscular junction, and in brain and spinal synapses. Some nAChRs are also expressed in non-neuronal or muscle cells. Within the nervous system, these non-neuronal cells include microglia and astrocytes; outside the nervous system non-neuronal cells expressing alpha7 receptors include macrophages, vascular endothelium and pulmonary epithelial cells.

All known mammalian nAChRs are cation selective ligand-gated ion channels that form pentameric structures in the plasma membrane. Each subunit of the pentamer contains four transmembrane domains. There are at least seventeen different nAChR subunit genes, including five found in striated muscle ($\alpha$1, $\beta$1, $\gamma$, $\delta$, $\epsilon$) and twelve neuronal nAChR subunits ($\alpha$2-10, $\beta$2-4). These channels can be composed of a number of different combinations of subunits. Examples of the most abundant subtypes in the brain include the $\alpha$7 subtype ($\alpha$-bungarotoxin sensitive) and the $\alpha$4$\beta$2 subtypes ($\alpha$4(2)$\beta$2(3) or $\alpha$4(3)$\ominus$2(2)). There is strong evidence supporting the idea that most $\alpha$7 receptors are expressed as homopentamers. Functional bungarotoxin sensitive channels are expressed in *Xenopus oocytes* when only $\alpha$7 cDNA is injected. However, rat hippocampal interneurons have $\alpha$7-containing nAChRs that exhibit pharmacological and functional properties different from those of homomeric $\alpha$7 receptors. The co-expression of the $\alpha$7 subunit with the $\beta$2 subunit in *Xenopus oocytes* has produced functional heteromeric channels with similar properties to the rat hippocampal interneuron $\alpha$7-containing receptor (Khiroug et al. 2004 *J. Physiol.* (*London*) 540:425-434). In addition to its ability to assemble into homomeric channels, the $\alpha$7 nAChR channel displays much greater permeability to calcium ions than other nAChRs or the NMDA glutamate receptor subtype.

Neuronal nAChR deficits have been implicated in several diseases including AD and schizophrenia. Until recently, the study of neurodegenerative diseases focused on the muscarinic type neuronal acetylcholine receptor (mAChR) because of its abundance in the brain when compared to the population of neuronal nicotinic receptors (nAChRs). However, the discovery of a greater relative loss of nicotinic receptors than of muscarinic receptors in the Alzheimer's brain, as well as evidence that nicotinic agonists enhance cognition has spurred interest in nAChRs. This is supported by the observation of enhanced attentiveness and rapid information processing in humans receiving nicotine or DMXBA (GTS-21) treatment. The two major brain nAChRs alpha4beta2 ($\alpha$4$\beta$2) and alpha 7 are important for cognitive processes such as attention, learning and memory. Since brain alpha7 nicotinic receptors are spared relative to the alpha4beta2 nAChRs in Alzheimer's disease and also possess exceptionally high calcium ion permeability, they are considered a particularly promising therapeutic target for treatment of Alzheimer's disease. In addition to their direct involvement in synaptic transmission, certain nicotinic receptor subtypes, particularly alpha7, because of their very high calcium permeability also stimulate calcium-dependent intracellular signal transduction processes that are neuroprotective by maintaining neuronal integrity in the presence of stressful states such as ischemia or mechanical trauma.

Central cholinergic neurons have been implicated in a number of neurodegenerative conditions including, AD and schizophrenia. AD affects an estimated 15 million people worldwide and accounts for approximately 50-60% of the overall cases of dementia for people over the age of 65. The characteristic pathology of AD includes extracellular $\beta$-amyloid plaques, intracellular neurofibrillary tangles, loss of neuronal synapses and pyramidal cells. The cholinergic dysfunction in AD is represented by a reduction in the activity of the ACh-synthesizing enzyme cholineactyltransferase (ChAT) and a loss in functional nAChRs. This alteration is possibly attributable to a reduction in nAChR synthesis, and/or to changes in nicotinic receptor pharmacology due to modifications in the binding site. In schizophrenia, there is a disruption in the normal brain mechanism that eliminates repetitive stimuli in order to reduce the flow of information. This malfunction in the simple filter for sensory input causes an overload of stimuli, which may lead to misperceptions of sensory stimuli producing delusions, or withdrawal from stimuli causing schizoid behavior.

It is now known that selective alpha7 nicotinic receptor agonists can improve memory-related behaviors and protect against neurotoxicity induced by trophic factor deprivation, amyloid exposure, excitotoxicity, in viva ischemia and axotomy (Li et al., 2000). The α7nAChR subtype is known to cause long-term synaptic modulation through its influence on glutamatergic synapses. Strong, brief stimulation of presynaptic α7-containing nAChRs can enhance hippocampal glutamatergic synaptic transmission for some time after the nicotinic agonist has been removed (Radcliffe and Dani, 1998).

DMXBA, 3-(2,4-dimethoxy benzylidene)-anabaseine is a well-studied compound that selectively activates alpha7 receptors in rats and has shown promise in Phase I human clinical trials. It also is an antagonist at alpha4beta2 receptors. DMXBA is less toxic than nicotine and does not affect autonomic and skeletal muscle systems at doses used to enhance cognitive behavior. Clinical tests of DMXBA indicate that large doses could be safely administered orally without adverse effects (Kitagawa et al., 2003. *Neuropsychopharmacology* 28:542-551; Olincy et al., 2006. *Arch. Gen. Psychiat.*, in press).

Despite promising results in studies of anabaseine-related compounds such as DMXBA for potential treatment of cognitive disorders, these compounds penetrate into all tissues of the body, making them unsuitable for treating certain peripheral diseases. The action of DMXBA, for example, cannot be restricted to peripheral (accessible from the blood compartment) alpha7 receptors, which have recently been shown to have therapeutic importance for treating certain diseases.

The importance of developing highly selective alpha7 nicotinic receptor agonists has increased as the role of these receptors in degenerative disease becomes clearer. There is a particular need for new compounds useful in treating cognitive dysfunctions such as AD where degenerative processes drastically interfere with cognitive and physiological processes. Accordingly, compounds that are safe and are highly selective as alpha7 nicotinic receptor agonists would be prime candidates for therapeutics to treat human diseases involving neurodegeneration or defective development of the brain.

While some anabaseine-related compounds hold promise as alpha7 agonist drugs, they are not completely selective and can have antagonistic effects on brain alpha4beta2 subtype nicotinic receptors, which also participate in cognitive processes. Development of selective alpha7 agonists would allow less drug to be used, possibly with fewer side effects arising from interaction with other nicotinic receptor subtypes.

An additional advantage of new alpha7 agonist drugs would be identification of selective alpha7 agonists that do not penetrate into all tissues of the body, thus allowing their use in selectively targeting peripheral (accessible from the blood or pulmonary compartments) alpha7 receptors, which have recently been shown to have therapeutic importance for treating certain diseases.

SUMMARY OF THE INVENTION

Provided herein are novel 3-arylidene-anabaseine compounds as well as pharmaceutical formulations and kits including these anabaseine compounds and methods of using the anabaseine compounds, pharmaceutical formulations and kits.

Thus, in one aspect of the invention are provided novel 3-arylidene-anabaseine compounds as described in detail herein. These 3-arylidene-anabaseine compounds include particular 3-benzylidene-anabaseines (including 3-benzylidene-anabaseines that are alkyl-substituted on the tetrahydropyridyl ring carbons, as well as 3-benzylidene-anabaseines with particular combinations of substituents (other than hydrogen) on the phenyl ring of the benzylidene), 3-cinnamylidene-anabaseines, 3-(benzofuran-2-ylmethylene)-anabaseines, 3-(1H-indol-2-ylmethylene)-anabaseines, and 3-benzylidene-glucuronide-anabaseines as described herein.

In certain embodiments are provided 3-benzylidene-anabaseines of the formula:

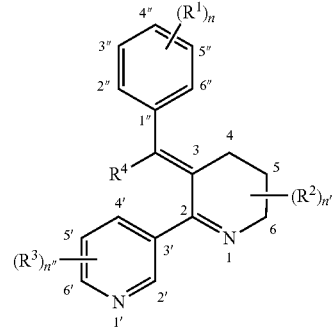

where $R^1$ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkyl hydroxy, hydroxyl, $C_1$-$C_3$ alkoxy, trifluoromethoxy, methylamino or thiomethoxy and n is 0-5; $R^2$ is independently $C_1$-$C_3$ alkyl and n' is 1-3, wherein at least one $R^2$ is present at position 4, 5, or 6; $R^3$ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; $R^4$ is hydrogen or $C_1$-$C_3$ alkyl or $C_1$-$C_3$ alkylhydroxy; or a pharmaceutically acceptable salt, solvate, clathrate, stereoisomer, enantiomer, prodrug or combination thereof.

In some embodiments of the 3-benzylidene-anabaseine, n is 1-3. In particular embodiments, $R^2$ is methyl. In certain of these embodiments, n is 1. In some embodiments, n is 2. In other embodiments, n is 3.

In some embodiments of the 3-benzylidene-anabaseine, n is 1-3. In particular embodiments, $R^2$ is ethyl. In certain of these embodiments, n is 1. In some embodiments, n is 2. In other embodiments, n is 3.

In some embodiments of the 3-benzylidene-anabaseine, n is 1-3. In particular embodiments, $R^2$ is propyl. In certain of these embodiments, n is 1. In some embodiments, n is 2. In other embodiments, n is 3.

In some embodiments of the 3-benzylidene-anabaseines, the anabaseine is enriched in one enantiomer and shows greater relative selectivity for the α7 nicotinic receptor versus the α4β2 nicotinic receptor when compared to the anabaseine enriched in the other enantiomer.

In certain embodiments of the 3-benzylidene-anabaseines, the anabaseine is enriched in one enantiomer and shows greater relative selectivity for the α7 nicotinic receptor versus the α4β2 nicotinic receptor when compared to a racemic mixture of the anabaseine.

In certain embodiments of the 3-benzylidene-anabaseines, $R^2$ is at position 4. In some embodiments, $R^2$ is at position 5.

In other embodiments, R² is at position 6. In some of these embodiments, n is 1. In others, n is 2 or 3. In certain embodiments, R² is methyl. In others, R² is ethyl. In still others, R² is propyl.

In certain embodiments of the 3-benzylidene-anabaseines, R¹ is, independently, hydroxy, amino, methylamino, thiomethoxy, or methoxy. In certain of these embodiments, n is 1. In others, n is 2. In still others, n is 3. In particular of these embodiments, each R¹ is methoxy. In some embodiments, R¹ is at the 2" and 4" positions. In particular embodiments, wherein n is 1-5 and one of said R¹s is, independently, at the 2" or 4" position. In other embodiments, n is 1 and R¹ is at the 4" position.

In certain embodiments are provided enantiomerically enriched 3-arylidene-anabaseine compounds, wherein the anabaseine compound is C₁-C₃ alkyl-substituted at one or more carbon atoms of the tetrahydropyridyl ring. In particular embodiments, the enantiomerically enriched 3-arylidene-anabaseine compound is a 3-benzylidene-anabaseine as described herein. In certain embodiments, the 3-arylidene-anabaseine compound is enriched in the R-isomer. In other embodiments, the 3-arylidene-anabaseine compound is enriched in the S-isomer. In particular embodiments, the enantiomerically enriched 3-arylidene-anabaseine compound is 4-methyl-DMXBA, 5-methyl-DMXBA, 6-methyl-DMXBA, 3-(4-hydroxybenzylidene)-4-methylanabaseine, or 3-(4-hydroxybenzylidene)-6-methylanabaseine. In certain embodiments, the enantiomerically enriched 3-arylidene-anabaseine compound is 4-methyl-DMXBA, 5-methyl-DMXBA, or 6-methyl-DMXBA. In other embodiments, the enantiomerically enriched 3-arylidene-anabaseine compound is 3-(4-hydroxybenzylidene)-4-methylanabaseine or 3-(4-hydroxybenzylidene)-6-methylanabaseine. In certain of these embodiments, the 3-arylidene-anabaseine compound is enriched in the S-isomer. In others it is enriched in the R-isomer.

In some embodiments of the 3-benzylidene-anabaseines, the anabaseine is 4-methyl-DMXBA. In certain embodiments the 4-methyl-DMXBA is enriched in the one enantiomer that has a greater retention time on a Chiracel OJ-H column than the other enantiomer. In certain embodiments, the solvent profile is as described herein. In certain embodiments, the greater retention time is about 26 minutes. In other embodiments, the 4-methyl-DMXBA is enriched in the one enantiomer which has a shorter retention time on a Chiracel OJ-H column than the other enantiomer. In certain embodiments, the shorter retention time is about 21 minutes.

In some embodiments of the 3-benzylidene-anabaseines, the anabaseine is 4-methyl-DMXBA and the 4-methyl-DMXBA is enriched in one enantiomer and shows greater relative selectivity for the α7 nicotinic receptor versus the α4β2 nicotinic receptor when compared to the other enantiomer of 4-methyl-DMXBA.

In some embodiments of the 3-benzylidene-anabaseines, the anabaseine is 4-methyl-DMXBA and the 4-methyl-DMXBA is enriched in one enantiomer and shows greater relative selectivity for the α7 nicotinic receptor versus the α4β2 nicotinic receptor when compared to the racemic mixture of 4-methyl-DMXBA.

In some embodiments of the 3-benzylidene-anabaseines, the anabaseine is 6-methyl-DMXBA. In certain embodiments the 6-methyl-DMXBA is enriched in the one enantiomer that has a greater retention time on a Chiracel OJ-H column than the other enantiomer. In certain embodiments, the greater retention time is about 29 minutes. In other embodiments, the 6-methyl-DMXBA is enriched in the one enantiomer which has a shorter retention time on a Chiracel OJ-H column than the other enantiomer. In certain embodiments, the shorter retention time is about 21 minutes.

In some embodiments of the 3-benzylidene-anabaseines, the anabaseine is 6-methyl-DMXBA and the 6-methyl-DMXBA is enriched in one enantiomer and shows greater relative selectivity for the α7 nicotinic receptor versus the α4β2 nicotinic receptor when compared to the other enantiomer of 6-methyl-DMXBA.

In some embodiments of the 3-benzylidene-anabaseines, the anabaseine is 6-methyl-DMXBA and the 6-methyl-DMXBA is enriched in one enantiomer and shows greater relative selectivity for the α7 nicotinic receptor versus the α4β2 nicotinic receptor when compared to the racemic mixture of 6-methyl-DMXBA.

In some embodiments of the 3-benzylidene-anabaseines, the anabaseine is 5-methyl-DMXBA. In certain embodiments the 5-methyl-DMXBA is enriched in the one enantiomer that has a greater retention time on a Chiracel OJ-H column than the other enantiomer. In certain embodiments, the greater retention time is about 27 minutes. In other embodiments, the 5-methyl-DMXBA is enriched in the one enantiomer which has a shorter retention time on a Chiracel OJ-H column than the other enantiomer. In certain embodiments, the shorter retention time is about 25 minutes.

In some embodiments of the 3-benzylidene-anabaseines, the anabaseine is 5-methyl-DMXBA and the 5-methyl-DMXBA is enriched in one enantiomer and shows greater relative selectivity for the α7 nicotinic receptor versus the α4β2 nicotinic receptor when compared to the other enantiomer of 5-methyl-DMXBA.

In some embodiments of the 3-benzylidene-anabaseines, the anabaseine is 5-methyl-DMXBA and the 5-methyl-DMXBA is enriched in one enantiomer and shows greater relative selectivity for the α7 nicotinic receptor versus the α4β2 nicotinic receptor when compared to the racemic mixture of 5-methyl-DMXBA.

In some embodiments of the 3-benzylidene-anabaseines, the 3-benzylidene-anabaseine is a α7 nicotinic receptor agonist.

In certain embodiments of the 3-benzylidene-anabaseines, the 3-benzylidene-anabaseine is a α7 nicotinic receptor full agonist. In particular embodiments, the 3-benzylidene-anabaseine is a α7 nicotinic receptor partial agonist.

In some embodiments of the 3-benzylidene-anabaseines, the 3-benzylidene-anabaseine is a α7 nicotinic receptor antagonist.

In certain embodiments are provided a 3-benzylidene-anabaseines of the formula:

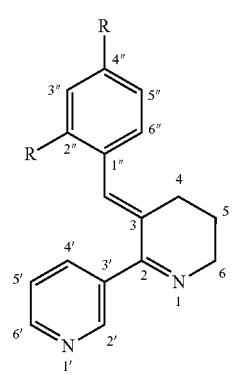

where the 2"R and 4"R are, independently, acetoxy, acetamido, amino, methylamino, dimethylamino, dimethylcarbamoyl, diethylcarbamoyl, methylcarbamoyl, ethylcarbamoyl, difluoromethoxy, dimethylaminopropoxy, hydroxyl, C₁-C₅ alkoxy, trifluoromethoxy, methylamino or thiomethoxy, provided that at least one of 2"R or 4"R is, independently, methylamino or dimethylcarbamoyl, diethylcarbamoyl, ethylcarbamoyl, methylcarbamoyl; or a pharmaceutically acceptable salt, solvate, clathrate, stereoisomer, enantiomer, prodrug or combination thereof.

In certain embodiments of the 3-benzylidene-anabaseines, 2"R and 4"R are each methylamino.

In some embodiments of the 3-benzylidene-anabaseines, 2"R is methylamino and 4"R is methoxy.

In some embodiments of the 3-benzylidene-anabaseines, 2"R is methylamino and 4"R is isopropoxy.

In some embodiments of the 3-benzylidene-anabaseines, 2"R and 4"R are each dimethylcarbamoyl.

In some embodiments of the 3-benzylidene-anabaseines, 2"R is dimethylcarbamoyl and 4"R is methoxy.

In some embodiments of the 3-benzylidene-anabaseines, 2"R is dimethylcarbamoyl and 4"R is isopropoxy.

In some embodiments of the 3-benzylidene-anabaseines, the 3-benzylidene-anabaseine is a α7 nicotinic receptor agonist. In certain embodiments, the 3-benzylidene-anabaseine is a α7 nicotinic receptor full agonist. In particular embodiments the 3-benzylidene-anabaseine is a α7 nicotinic receptor partial agonist.

In some embodiments of the 3-benzylidene-anabaseines the 3-benzylidene-anabaseine is a α7 nicotinic receptor antagonist.

In certain embodiments are provided 3-cinnamylidene-anabaseines of the formula:

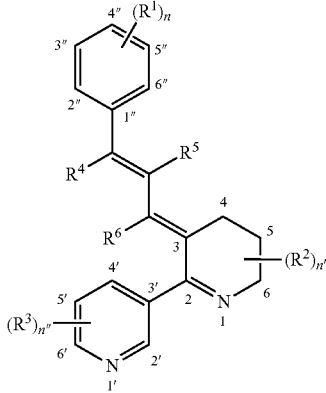

where $R^1$ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino or thiomethoxy and n is 0-5; $R^2$ is independently $C_1$-$C_3$ alkyl and n' is 1-3, wherein at least one $R^2$ is present at position 4, 5, or 6; $R^3$ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; $R^4$, $R^5$ and $R^6$ are, independently, hydrogen or $C_1$-$C_3$ alkyl or $C_1$-$C_3$ alkylhydroxy; or a pharmaceutically acceptable salt, solvate, clathrate, stereoisomer, enantiomer, prodrug or combination thereof.

In some embodiments of the 3-cinnamylidene-anabaseines, n is 1-3. In certain embodiments, $R^2$ is methyl.

In some embodiments of the 3-cinnamylidene-anabaseines, the 3-cinnamylidene-anabaseine is a α7 nicotinic receptor agonist. In certain embodiments, the 3-cinnamylidene-anabaseine is a α7 nicotinic receptor full agonist. In particular embodiments, the 3-cinnamylidene-anabaseine is a α7 nicotinic receptor partial agonist.

In some embodiments of the 3-cinnamylidene-anabaseines, the 3-cinnamylidene-anabaseine is a α7 nicotinic receptor antagonist.

In certain embodiments are provided 3-(benzofuran-2-ylmethylene)-anabaseines of the formula:

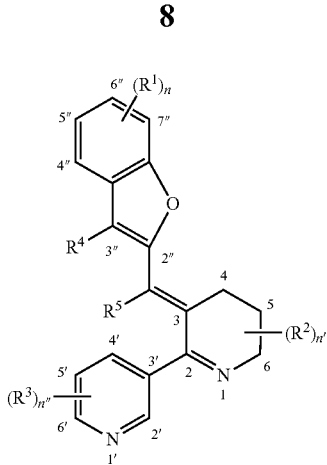

where $R^1$ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino or thiomethoxy and n is 0-4; $R^2$ is independently $C_1$-$C_3$ alkyl and n' is 1-3, wherein at least one $R^2$ is present at position 4, 5, or 6; $R^3$ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; $R^4$ and $R^5$ are, independently, hydrogen, $C_1$-$C_3$ alkyl or $C_1$-$C_3$ alkylhydroxy; or a pharmaceutically acceptable salt, solvate, clathrate, stereoisomer, enantiomer, prodrug or combination thereof.

In some embodiments of the 3-(benzofuran-2-ylmethylene)-anabaseines, n is 1-3. In certain embodiments, $R^2$ is methyl.

In some embodiments of the 3-(benzofuran-2-ylmethylene)-anabaseines, the 3-(benzofuran-2-ylmethylene)-anabaseine is a α7 nicotinic receptor agonist. In certain embodiments, the 3-(benzofuran-2-ylmethylene)-anabaseine is a α7 nicotinic receptor full agonist. In particular embodiments, the 3-(benzofuran-2-ylmethylene)-anabaseine is a α7 nicotinic receptor partial agonist.

In some embodiments of the 3-(benzofuran-2-ylmethylene)-anabaseines, the 3-(benzofuran-2-ylmethylene)-anabaseine is a α7 nicotinic receptor antagonist.

In certain embodiments are provided 3-(1H-indol-2-ylmethylene)-anabaseines having the formula:

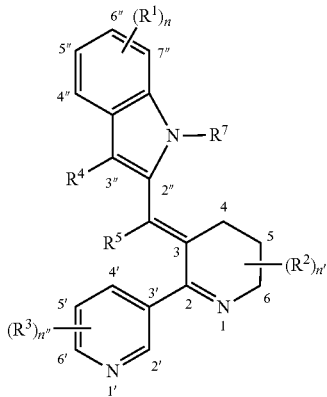

where $R^1$ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino or thiomethoxy and n is 0-4; $R^2$ is independently $C_1$-$C_3$ alkyl and n' is 1-3, wherein at least one $R^2$ is present at position 4, 5, or 6; $R^3$ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; $R^4$ and $R^5$ are, independently, hydrogen, $C_1$-$C_3$ alkyl or $C_1$-$C_3$ alkylhydroxy; $R^7$ is hydrogen, $C_1$-$C_5$ alkyl, $C_1$-$C_5$ dialkoxy, or $C_1$-$C_5$ alkoxy; or a pharmaceutically acceptable salt, solvate, clathrate, stereoisomer, enantiomer, prodrug or combination thereof.

In some embodiments of the 3-(1H-indol-2-ylmethylene)-anabaseines, n is 1-3. In certain embodiments, $R^2$ is methyl.

In some embodiments of the 3-(1H-indol-2-ylmethylene)-anabaseines, the 3-(1H-indol-2-ylmethylene)-anabaseine is a α7 nicotinic receptor agonist. In certain embodiments, the 3-(1H-indol-2-ylmethylene)-anabaseine is a α7 nicotinic receptor full agonist. In particular embodiments, the 3-(1H-indol-2-ylmethylene)-anabaseine is a α7 nicotinic receptor partial agonist.

In some embodiments of the 3-(1H-indol-2-ylmethylene)-anabaseines, the 3-(1H-indol-2-ylmethylene)-anabaseine is a α7 nicotinic receptor antagonist.

In certain embodiments are provided 3-arylidene-anabaseines of the formula:

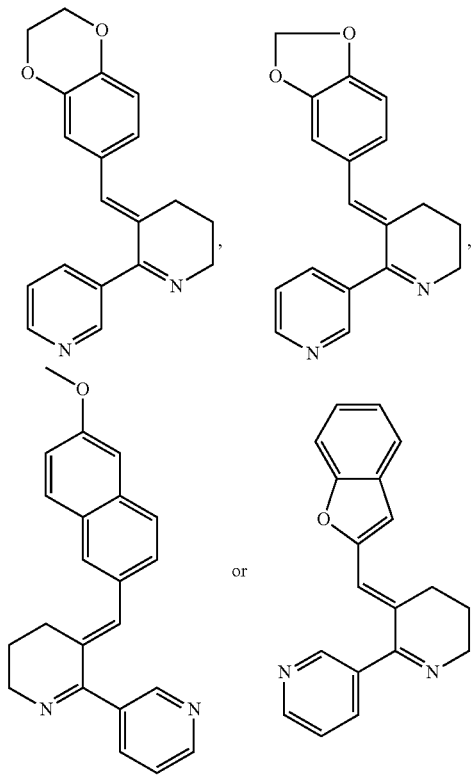

or a pharmaceutically acceptable salt, solvate, clathrate, stereoisomer, enantiomer, prodrug or combination thereof.

In particular embodiments are provided 3-arylidene-anabaseines selected from the group consisting of 3-(3,4-(ethylenedioxy)benzylidene)-anabaseine, 3-(3,4-(methylenedioxy)benzylidene)-anabaseine, 3-((6-methoxynaphth-2-yl)methylene)-anabaseine, and 3-((benzofuran-2-yl)methylene)-anabaseine.

In some embodiments are provided 3-benzylidene-glucuronide-anabaseines, which include a modified glucuronide, of the formula:

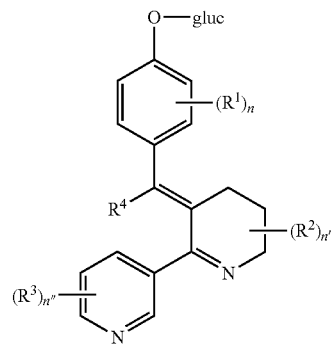

where $R^1$ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino, acylated glucuronidyl, or thiomethoxy and n is 0-4; $R^2$ is independently $C_1$-$C_3$ alkyl and n' is 0-3; $R^3$ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; $R^4$ is hydrogen, $C_1$-$C_3$ alkyl or $C_1$-$C_3$ alkylhydroxy; gluc is glucuronidyl optionally esterified with a $C_1$-$C_4$ alkylhydroxy and where the glucuronidyl hydroxy groups can be acylated with a $C_1$-$C_3$ acyl group (e.g., acetyl, propionyl, butyryl, etc.); or a pharmaceutically acceptable salt, solvate, clathrate, stereoisomer, enantiomer, prodrug or combination thereof.

In some embodiments of the 3-benzylidene-glucuronide-anabaseines, n' is 1-3 and an $R^2$ is present at position 4, 5, or 6.

In some embodiments of the 3-benzylidene-glucuronide-anabaseines, n is 1-3. In certain embodiments, $R^2$ is methyl.

In some embodiments of the 3-benzylidene-glucuronide-anabaseines, the 3-benzylidene-glucuronide-anabaseine is a α7 nicotinic receptor agonist. In certain embodiments, the 3-benzylidene-glucuronide-anabaseine is a α7 nicotinic receptor full agonist. In particular embodiments, the 3-benzylidene-glucuronide-anabaseine is a α7 nicotinic receptor partial agonist.

In some embodiments of the 3-benzylidene-glucuronide-anabaseines, the 3-benzylidene-glucuronide-anabaseine is a α7 nicotinic receptor antagonist.

In some embodiments are provided 3-benzylidene-glucuronide-anabaseines, which include a modified glucuronide, of the formula:

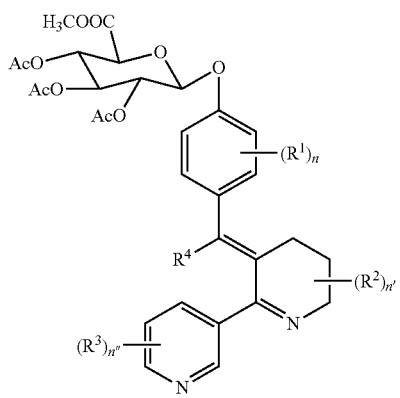

where $R^1$ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino, acylated glucuronidyl, or thiomethoxy and n is 0-4; $R^2$ is independently $C_1$-$C_3$ alkyl and n' is 0-3; $R^3$ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; $R^4$ is hydrogen, $C_1$-$C_3$ alkyl or $C_1$-$C_3$ alkylhydroxy; or a pharmaceutically acceptable salt, solvate, clathrate, stereoisomer, enantiomer, prodrug or combination thereof.

In some embodiments of the 3-benzylidene-glucuronide-anabaseines, n' is 1-3 and an $R^2$ is present at position 4, 5, or 6.

In some embodiments of the 3-benzylidene-glucuronide-anabaseines, n is 1-3. In certain embodiments, $R^2$ is methyl.

In some embodiments of the 3-benzylidene-glucuronide-anabaseines, the 3-benzylidene-glucuronide-anabaseine is a α7 nicotinic receptor agonist. In certain embodiments, the 3-benzylidene-glucuronide-anabaseine is a α7 nicotinic receptor full agonist. In particular embodiments, the 3-benzylidene-glucuronide-anabaseine is a α7 nicotinic receptor partial agonist.

In some embodiments of the 3-benzylidene-glucuronide-anabaseines, the 3-benzylidene-glucuronide-anabaseine is a α7 nicotinic receptor antagonist.

In another aspect of the present invention are provided pharmaceutical formulations of the 3-arylidene-anabaseine compounds described herein, comprising at least one of the 3-arylidene-anabaseines as described herein and one or more pharmaceutically acceptable carriers, excipients, diluents, stabilizers or preservatives.

In still another aspect of the invention are provided methods of using the 3-arylidene-anabaseine compounds, or pharmaceutical formulations thereof, as described herein.

In certain embodiments are provided pharmaceutically acceptable compositions comprising at least one of the 3-benzylidene-anabaseines described herein and one or more pharmaceutically acceptable carriers, excipients, diluents, stabilizers or preservatives.

In certain embodiments are provided pharmaceutically acceptable compositions comprising at least one of the 3-cinnamylidene-anabaseines described herein and one or more pharmaceutically acceptable carriers, excipients, diluents, stabilizers or preservatives.

In certain embodiments are provided pharmaceutically acceptable compositions comprising at least one of the 3-(1H-indol-2-ylmethylene)-anabaseines described herein and one or more pharmaceutically acceptable carriers, excipients, diluents, stabilizers or preservatives.

In certain embodiments are provided pharmaceutically acceptable compositions comprising at least one of the 3-(benzofuran-2-ylmethylene)-anabaseines described herein and one or more pharmaceutically acceptable carriers, excipients, diluents, stabilizers or preservatives.

In certain embodiments are provided pharmaceutically acceptable compositions comprising at least one of the-3-benzylidene-glucuronide-anabaseine described herein and one or more pharmaceutically acceptable carriers, excipients, diluents, stabilizers or preservatives.

In particular embodiments, the 3-arylidene-anabaseines may be used to selectively stimulate α7 nicotinic receptors as described herein.

In certain embodiments are provided methods of selectively stimulating alpha7 nicotinic receptors, comprising the step (a) administering a therapeutically effective amount of a 3-benzylidene-anabaseine as described herein to an individual in need thereof.

In certain embodiments are provided methods of selectively stimulating alpha7 nicotinic receptors, comprising the step (a) administering a therapeutically effective amount of a 3-benzylidene-anabaseine as described herein to an individual in need thereof.

In certain embodiments are provided methods of selectively stimulating alpha7 nicotinic receptors, comprising the step (a) administering a therapeutically effective amount of a 3-cinnamylidene-anabaseine as described herein to an individual in need thereof.

In certain embodiments are provided methods of selectively stimulating alpha7 nicotinic receptors, comprising the step (a) administering a therapeutically effective amount of a 3-(benzofuran-2-ylmethylene)-anabaseine as described herein to an individual in need thereof.

In certain embodiments are provided methods of selectively stimulating alpha7 nicotinic receptors, comprising the step (a) administering a therapeutically effective amount of a 3-(1H-indol-2-ylmethylene)-anabaseine as described herein to an individual in need thereof.

In certain embodiments are provided methods of selectively stimulating alpha7 nicotinic receptors, comprising the step (a) administering a therapeutically effective amount of a benzylidene-glucuronide-anabaseine as described herein to an individual in need thereof.

In certain embodiments are provided methods of selectively inhibiting alpha7 nicotinic receptors, comprising the step (a) administering a therapeutically effective amount of a 3-benzylidene-anabaseine as described herein to an individual in need thereof.

In certain embodiments are provided methods of selectively inhibiting alpha7 nicotinic receptors, comprising the step (a) administering a therapeutically effective amount of a 3-benzylidene-anabaseine of as described herein to an individual in need thereof.

In certain embodiments are provided methods of selectively inhibiting alpha7 nicotinic receptors, comprising the step (a) administering a therapeutically effective amount of a 3-cinnamylidene-anabaseine as described herein to an individual in need thereof.

In certain embodiments are provided methods of selectively inhibiting alpha7 nicotinic receptors, comprising the step (a) administering a therapeutically effective amount of a 3-(benzofuran-2-ylmethylene)-anabaseine as described herein to an individual in need thereof.

In certain embodiments are provided methods of selectively inhibiting alpha7 nicotinic receptors, comprising the step (a) administering a therapeutically effective amount of a 3-(1H-indol-2-ylmethylene)-anabaseine as described herein to an individual in need thereof.

In certain embodiments are provided methods of selectively inhibiting alpha7 nicotinic receptors, comprising the step (a) administering a therapeutically effective amount of a benzylidene-glucuronide-anabaseine as described herein to an individual in need thereof.

In certain embodiments the condition to be treated is a neurological condition characterized by a reduced number of α7 nicotinic receptors. In some embodiments, the condition to be treated is a neurological condition characterized by degeneration or impairment of nicotinic alpha7 receptors. In some embodiments, the neurological condition is Alzheimer's disease, Parkinson's Disease, vascular dementia, age-related cognitive decline (AACD), mild cognitive impairment (MCI), AIDS-related dementia, schizophrenia, bipolar disorder, stimulant addiction (e.g., to cocaine, amphetamines, etc.), or psychoses (e.g., manic psychoses, etc.).

In particular embodiments the methods of using the 3-arylidene-anabaseine compounds described herein (or pharmaceutical formulations thereof) include methods of enhancing cognitive behavior in an individual, comprising the step (a) administering to individual in need thereof, a therapeutically effective amount of a 3-arylidene-anabaseine (or pharmaceutical composition thereof) described herein.

In particular embodiments, the cognitive behavior is learning or memory retention.

Some embodiments of the methods of using the 3-arylidene-anabaseine compounds described herein (or pharmaceutical formulations thereof) include methods of ameliorating glutamate-induced toxicity toward cortical cells, comprising the step (a) administering to an individual in need thereof a therapeutically effective amount of a 3-arylidene-anabaseine compound (or pharmaceutical formulation thereof) as described herein.

Some embodiments of the methods of using the 3-arylidene-anabaseine compounds described herein (or pharmaceutical formulations thereof) include methods of reducing or ameliorating inflammation, comprising the step (a) administering to an individual in need thereof, therapeutically effective amount of a 3-arylidene-anabaseine compound (or pharmaceutical formulation thereof) as described herein to selectively stimulate alpha7 receptors in peripheral macrophages.

In certain embodiments, the inflammation is peripheral.

Particular embodiments of the methods of using the 3-arylidene-anabaseine compounds described herein (or pharmaceutical formulations thereof) include methods of reducing angiogenesis, comprising the step (a) administering a therapeutically effective amount of a 3-arylidene-anabaseine (or pharmaceutical formulation thereof) as described herein to the In some embodiments of each of the methods of using the compounds described herein, step (a) is performed once per day, twice per day, three times per day, four times per day, once every other day, once per week, or twice per week. In particular embodiments, step (a) is performed once per day or twice per day.

In some embodiments the methods further include a step (b), where step (b) includes administering to the individual a pharmaceutical agent (e.g., an anabaseine compound not described herein as a 3-arylidene-anabaseine or a pharmaceutical agent unrelated to anabaseines (e.g., a pro-angiogenic compound (e.g., nicotine, etc.); anti-angiogenic compound (e.g., mecamylamine, etc.); cancer chemotherapeutic compound (e.g., taxanes (e.g., paclitaxel, etc.), alkylating agents, etc.); cognition enhancement compound, etc.); additional treatment modality, or combinations of the foregoing. Step (b) may be performed prior to, concomitantly with, or after step (a). And, in some variations, step (b) may be performed more than once (e.g., twice, three times, etc.) (e.g., both prior to and after step (a), both concomitantly with and after step (a), both prior to and concomitantly with step (a), etc.). For example, in certain variations, step (b) may be performed prior to or concomitantly with step (a). In other variations, step (b) may be performed concomitantly with or after step (a). In still other variations, step (b) may be performed prior to or after step (a). In particular variations, step (b) may be performed prior to step (a). In some variations, step (b) may be performed concomitantly with step (a). In certain variations, step (b) may be performed after step (a).

Where step (b) includes administration of a combination of a pharmaceutical agent and an additional treatment modality (ies), each may be independently administered prior to, concomitantly with, or after step (a). In particular embodiments, step (b) includes a pharmaceutical agent. In particular embodiments, step (b) includes an additional treatment modality (e.g., surgical intervention (e.g., in the treatment of cancer, including tumors), radiation therapy, etc.).

In yet another aspect are provided kits including the 3-arylidene-anabaseine compounds or pharmaceutical formulations thereof as described herein. It is intended that any of the 3-arylidene-anabaseine compounds or pharmaceutical formulations thereof described herein may be included in the kits of the present invention. In certain embodiments are provided kits including any of the 3-arylidene-anabaseine compound(s) or pharmaceutical formulations thereof described herein, packaging and instructions for use.

In some embodiments, the kits include one or more additional pharmaceutical agents (non-3-arylidene-anabaseine compound pharmaceutical agents). In certain embodiments, the kits may include one or more non-3-arylidene-anabaseine compound nicotinic acetylcholine receptor agonists. In certain embodiments, the kits may include one or more non-3-arylidene-anabaseine compound nicotinic acetylcholine receptor antagonists. In particular embodiments, the pharmaceutical agent is provided in a separate container from the 3-arylidene-anabaseine compound or pharmaceutical formulations thereof.

In certain embodiments, the 3-arylidene-anabaseine compound(s) or pharmaceutical formulation(s) thereof is provided in a multi-dose form.

In particular embodiments, the 3-arylidene-anabaseine compound(s) or pharmaceutical formulation(s) thereof is provided in one or more single unit dose forms.

In some embodiments, sufficient 3-arylidene-anabaseine compound(s) or pharmaceutical formulation(s) thereof (in either unit dose or multi-dose form) is provided for treatment over a period of about 1 day, about 1 week, about 2 weeks, about 3 weeks, about 4 weeks, about 1 month, about 2 months, about 3 months, about 4 months, about 6 months, about 9 months, or about 1 year. In particular embodiments, sufficient 3-arylidene-anabaseine compound(s) or pharmaceutical formulation(s) thereof is provided for about 3 months. In other embodiments, sufficient compound or formulation is provided for about 1 or 2 months.

In some embodiments, the kits include more than one 3-arylidene-anabaseine compound or pharmaceutical formulation thereof (e.g., two, three, four or more 3-arylidene-anabaseine compounds).

Unless otherwise noted, the 3-arylidene-anabaseines described herein, and pharmaceutical formulations containing one or more 3-arylidene-anabaseines as described herein, are intended for use in the methods of treatment and/or prevention as described herein and may be incorporated in the kits described herein. The 3-arylidene-anabaseines and pharmaceutical formulations described herein may, unless clearly dictated otherwise by the context in which they appear, be made as described herein and, additionally using techniques known in the field in light of the teaching provided herein.

In a further aspect of the invention is provided use of the 3-arylidene-anabaseines and pharmaceutical formulations as described herein in the manufacture of a medicament, particularly the manufacture of a medicament for use in the treatment and/or prevention of conditions as described herein. Further, the 3-arylidene-anabaseine compounds and pharmaceutical formulations thereof, variously described herein, are also intended for use in the manufacture of a medicament for use in treatment and/or prevention of the conditions and, in accordance with the methods, described herein, unless clearly dictated otherwise by context or specifically noted.

DETAILED DESCRIPTION OF THE INVENTION

An important aspect of the invention is the development and identification of novel selective alpha7 subtype nicotinic acetylcholine receptor (nAChR) ligands that can either be receptor agonists (including partial agonists and full agonists) or antagonists. These compounds have potential therapeutic applications for the treatment of a variety of human and animal diseases. Because of their selectivity for animal nAChRs that are homologous to the mammalian alpha7 nAChR, these compositions may also be active as selective anti-parasitic drugs and pesticides.

The invention also encompasses the rational development of new compounds structurally related to arylidene-anabaseines, but which exhibit significantly enhanced alpha7 nAChR selectivity, relative to these basic structures. While previously described arylidene-anabaseines are selectively agonistic to alpha7 receptors, they also non-selectively bind to other nAChRs and prevent them from being stimulated by their natural transmitter acetylcholine. Since at least one of these other nAChRs (alpha4 beta2) also is important for normal CNS function, antagonism of this receptor would be counterproductive therapeutically and could cause adverse effects on mental function. Because of their greatly enhanced selectivity toward alpha7 receptors, these new structures, and compounds containing the important elements of these structures, will provide a panel of useful therapeutic agents that can be targeted not only to specific diseases, but also to particular areas of the body. For example, these agents can be targeted to the CNS for neurodegenerative conditions, or to peripheral areas in cases of systemic inflammation.

The present invention shows that selection of appropriate substituents on the arylidene, tetrahydropyridyl and pyridyl ring portions of anabaseine compounds determines alpha7 selectivity, either when done separately or in combinations. Certain substituents also determine alpha7 receptor efficacy; some substituents increase efficacy over benzylidene-anabaseines such as DMXBA, while other reduce efficacy to essentially zero, thereby creating a new group of alpha7 nAChR antagonists.

The invention is in broad terms the development of a series of 3-arylidene-anabaseine compounds that display significantly enhanced alpha7 receptor binding selectivity relative to other benzylidene- and cinnamylidene-anabaseine compounds that selectively stimulate alpha7 nicotinic receptors but are inhibitory at other nAChRs, particularly the neuronal alpha4beta2 subtype also involved in cognition-enhancing neuronal pathways. These benzylidene- and cinnamylidene-anabaseine compounds are not selective-binding ligands for the ACh-binding site on the alpha7 nAChR; rather, they are selectively stimulatory to the alpha7 subtype. Since transgenic mice lacking alpha4beta2 receptors experience distorted learning and enhanced neurodegeneration during aging (Picciotto et al., 1995, 1998), alpha7 nAChR-targeted drugs should avoid blocking this receptor whenever possible to avoid cognitive dysfunction.

Because inhibition of alpha4beta2 would be counterproductive therapeutically, the identification of 3-arylidene-anabaseine compounds that also selectively bind to the alpha7 receptor provides a new opportunity to simultaneously achieve greater enhancement of cognition and reduce adverse effects mediated through other, non-alpha7 nicotinic receptors. The unexpected selectivity of the disclosed compounds toward the apha7 receptor strongly suggests the utility of these compounds for development of agents for treatment of several conditions now known to involve either the alpha7 nicotinic receptors in the central nervous system, or alpha7 receptors occurring peripherally.

Abbreviations and definitions used herein include:

DMXBA (sometimes referred to as GTS-21 or DMXB) which is (E)-3-(2,4-dimethoxybenzylidene)-3,4,5,6-tetrahydro-2,3'-bipyridine (also known as 3-(2,4-dimethoxybenzylidene)-anabaseine. Similarly, 4-methyl-DMXBA may be used herein to refer to 3-(2,4-dimethoxybenzylidene)-(4-methyl)-3,4,5,6-tetrahydro-2,3'-bipyridine (also known as 3-(2,4-dimethoxybenzylidene)-4-methyl-anabaseine); 5-methyl-DMXBA may be used herein to refer to 3-(2,4-dimethoxybenzylidene)-(5-methyl)-3,4,5,6-tetrahydro-2,3'-bipyridine (also known as 3-(2,4-dimethoxybenzylidene)-5-methyl-anabaseine); 6-methyl-DMXBA may be used herein to refer to 3-(2,4-dimethoxybenzylidene)-(6-methyl)-3,4,5,6-tetrahydro-2,3'-bipyridine (also known as 3-(2,4-dimethoxybenzylidene)-6-methyl-anabaseine); etc.

As used herein, the terms "3-arylidene-anabaseine compounds," "3-arylidene-anabaseines," including cognates of the foregoing, refer collectively to the 3-arylidene-anabaseine compounds described herein, including the 3-arylidene compounds encompassed by the formulae disclosed herein (explicitly including the 3-benzylidene-anabaseines, 3-cinnamylidene-anabaseines, benzofuran-2-ylmethylene-anabaseine, 3-(1H-indol-2-ylmethylene)-anabaseines, and 3-benzylidene-glucuronide-anabaseines, described herein, unless otherwise noted). It is intended that this term also collectively refers to pharmaceutically acceptable salts, solvates, clathrates, stereoisomers, enantiomers, and prodrugs of the 3-arylidene-anabaseine compounds described herein, including where a sample of a 3-arylidene-anabaseine compound is enriched in a particular enantiomer compared to the racemic mixture (e.g., a sample enriched in the (S)-isomer, or a sample enriched in the (R)-isomer, when compared to the racemic mixture), as is also described in greater detail herein. It is not intended that these terms or the formulae described herein encompass any of the anabaseine compounds disclosed in U.S. Pat. Nos. 5,977,144 and 5,741, 802.

The term "acyl" refers to the radical —C(O)R, where R can be H or a $C_1$-$C_6$ alkyl group (as described herein), including straight-chain alkyl groups, and branched-chain alkyl groups. In some embodiments, R is a $C_1$-$C_4$ alkyl, $C_1$-$C_5$ alkyl, $C_1$-$C_3$ alkyl. Acyl groups include formyl, acetyl, etc.)

The term "alkyl" refers to the radical of saturated aliphatic groups, including straight-chain alkyl groups, and branched-chain alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 6 or fewer carbon atoms in its backbone (e.g., $C_1$-$C_6$ for straight chain, $C_3$-$C_6$ for branched chain), preferably 6 or fewer, and more preferably 4 or fewer, and still more preferably 3 or fewer.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, acylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate.

The term "alkyl" also includes unsaturated aliphatic groups analogous in length and possible substitution to the alkyls described above, but that contain at least one double or triple bond respectively. An "alkylaryl" moiety is an alkyl substituted with an aryl (e.g., phenyl methyl (benzyl)). An "alkylhydroxy" is an alkyl substituted with a hydroxy group (e.g., $C_1$-$C_3$ alkylhydroxy includes —$CH_2OH$, —$(CH_2)_2OH$, —$(CH_2)_3OH$).

The terms "alkoxy," "amino alkyl" and "thioalkoxy" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aralkyl" means an aryl group that is attached to another group by a ($C_1$-$C_6$)alkylene group. Aralkyl groups may be optionally substituted, either on the aryl portion of the aralkyl group or on the alkylene portion of the aralkyl group, with one or more substituents.

The term "aryl" as used herein, refers to the radical of aryl groups, including 5- and 6-membered single-ring aromatic groups that may include from zero to four heteroatoms (heteroaryl), for example, phenyl, pyrrolyl, furyl, thiophen-yl, imidazolyl, benzoxazolyl, benzothiazolyl, triazolyl, tetrazolyl, pyrazolyl, pyridyl, pyrazinyl, pyridazinyl and pyrimidinyl, and the like. Aryl groups also include polycyclic fused aromatic groups such as naphthyl, quinolyl, indolyl, and the like.

Those aryl groups having heteroatoms in the ring structure may also be referred to as "heteroaryls" or "heteroaromatics." The aromatic ring can be substituted at one or more ring positions with such substituents as described above, as for example, halogen, hydroxy, alkoxy, alkylcarbonyloxy, arylcarbonyloxy, alkoxycarbonyloxy, aryloxycarbonyloxy, carboxylate, alkylthiocarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, halogenated alkyl (including trifluoromethyl, difluoromethyl and flurormethyl), halogenated alkoxy (including trifluoromethoxy, difluoromethoxy and fluoromethoxy), cyano, azido, heterocyclyl, alkylaryl, arylalkyl or an aromatic or heteroaromatic moiety. Aryl groups can also be fused or bridged with alicyclic or heterocyclic rings, which are not aromatic so as to form a polycycle (e.g., tetralin).

The term "cyclyl" refers to a hydrocarbon 3-8 membered monocyclic or 7-14 membered bicyclic ring system having at least one non-aromatic ring, wherein the non-aromatic ring has some degree of unsaturation. Cyclyl groups may be optionally substituted with one or more substituents. In one embodiment, 0, 1, 2, 3, or 4 atoms of each ring of a cyclyl group may be substituted by a substituent. The term "cycloalkyl" refers to a hydrocarbon 3-8 membered monocyclic or 7-14 membered bicyclic ring system having at least one saturated ring. Cycloalkyl groups may be optionally substituted with one or more substituents. In one embodiment, 0, 1, 2, 3, or 4 atoms of each ring of a cycloalkyl group may be substituted by a substituent. Cycloalkyls can be further substituted, e.g., with the substituents described above. Preferred cyclyls and cycloalkyls have from 3-10 carbon atoms in their ring structure, and more preferably have 3, 4, 5, 6 or 7 carbons in the ring structure. Those cyclic groups having heteroatoms in the ring structure may also be referred to as "heterocyclyl," "heterocycloalkyl" or "heteroaralkyl." The aromatic ring can be substituted at one or more ring positions with such substituents as described above.

The terms "cyclyl" or "cycloalkyl" refer to the radical of two or more cyclic rings (e.g., cycloalkyls, cycloalkenyls, cycloalkynyls, aryls, heteroaryls, and/or heterocyclyls). In some cases, two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, halogenated alkyl (including trifluoromethyl, difluoromethyl and flurormethyl), halogenated alkoxy (including trifluoromethoxy, difluoromethoxy and fluoromethoxy), cyano, azido, heterocyclyl, alkyl, alkylaryl, or an aromatic or heteroaromatic moiety.

The term "carbamoyl" refers to the radical —C(O)—$NH_2$, where one or both hydrogens bound to the nitrogen atom may optionally be independently replaced with a $C_1$-$C_4$ alkyl (e.g., —C(O)—NH($C_1$-$C_4$ alkyl), —C(O)—N($C_1$-$C_4$ alkyl)$_2$ or an aromatic moiety (e.g., phenyl (either substituted or unsubstituted) or heteroaryl moiety (e.g., pyridyl (either substituted or unsubstituted), etc.). In certain embodiments, the carbamoyl may be, for example, dimethylcarbamoyl, methylcarbamoyl, ethylcarbomoyl, diethylcarbamoyl, methyl-phenylcarbamoyl, methyl-pyridylcarbamoyl, etc.

The term "haloalkyl" is intended to include alkyl groups as defined above that are mono-, di- or polysubstituted by halogen, e.g., fluoromethyl and trifluoromethyl.

The term "halogen" or "halo" designates —F, —Cl, —Br or —I.

The term "hydroxy" means —OH.

The term "heteroatom" as used herein means an atom of any element other than carbon or hydrogen. Preferred heteroatoms are nitrogen, oxygen, sulfur and phosphorus.

The term "mercapto" refers to a —SH group.

The term "sulfhydryl" or "thiol" means —SH.

The compounds of the invention encompass various isomeric forms. Such isomers include, e.g., stereoisomers, e.g., chiral compounds, e.g., diastereomers and enantiomers.

The term "chiral" refers to molecules, which have the property of non-superimposability of the mirror image partner, while the term "achiral" refers to molecules, which are superimposable on their mirror image partner.

The term "diastereomers" refers to stereoisomers with two or more centers of dissymmetry and whose molecules are not mirror images of one another.

The term "enantiomers" refers to two stereoisomers of a compound, which are non-superimposable mirror images of one another. An equimolar mixture of two enantiomers is called a "racemic mixture" or a "racemate."

When a 3-arylidene-anabaseine compound (or pharmaceutical formulation thereof) is referred to as "enriched" in a particular enantiomer, it is intended that more of one particular enantiomer is present than the other enantiomer. For example, where a sample is said to be enriched in the (S)-enantiomer, it is to be understood that more of the (S)-enantiomer is present in the sample of compound than the (R)-isomer. Samples enriched in a particular isomer can include samples in which greater than about 50%, greater than about 60%, greater than about 70%, greater than about 80%, greater than about 90%, and about 100% of that particular isomer. Particular enantiomers may also be characterized by (including differentiated from each other and/or the racemic mixture) and/or referred to by their relative retention times on a given chiral chromatography column compared to each other or compared to the racemic mixture of the same compound. Similarly, particular enantiomers can also be characterized (including differentiated from each other and/or the racemic mixture) by their optical rotation, which can be determined readily by the skilled artisan.

The term "isomers" or "stereoisomers" refers to compounds, which have identical chemical constitution, but differ with regard to the arrangement of the atoms or groups in space.

Furthermore the indication of configuration across a carbon-carbon double bond can be "Z" referring to what is often referred to as a "cis" (same side) conformation whereas "E" refers to what is often referred to as a "trans" (opposite side) conformation. Regardless, both configurations, cis/trans and/or Z/E are contemplated for the compounds for use in the present invention.

With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

Natural amino acids represented by the compounds utilized in the present invention are in the "L" configuration, unless otherwise designated. Unnatural or synthetic amino acids represented by the compounds utilized in the present invention may be in either the "D" or "L" configurations. Similarly, glycosidic bonds may be in either alpha- or beta-configuration.

Another aspect is an isotopologue compound of any of the formulae delineated herein. Such compounds have one or more isotopic atoms (e.g., $^3$H, $^2$H, $^{14}$C, $^{13}$C, $^{35}$S, $^{32}$P, $^{125}$I, $^{131}$I) introduced into the compound. Such compounds are useful for drug metabolism studies and diagnostics, as well as therapeutic applications.

The term "obtaining" as used in obtaining the benzylidene-anabaseine or cinnamylidene-3-arylidene-anabaseine compound as used herein is intended to include purchasing, synthesizing or otherwise acquiring the benzylidene-anabaseine or cinnamylidene-3-arylidene-anabaseine compound.

The term "prodrug" includes compounds with moieties, which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19; Silverman (2004) *The Organic Chemistry of Drug Design and Drug Action*, Second Ed., Elsevier Press, Chapter 8, pp. 497-549). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halogen, or methoxy substituents) aryl and aryl-lower alkyl esters, amides, lower-alkyl amides, di-lower alkyl amides, and hydroxy amides. Preferred prodrug moieties are propionoic and succinic acid esters, acyl esters and substituted carbamates. Prodrugs, which are converted to active forms through other mechanisms in vivo, are also included.

3-Arylidene-Anabaseine Compounds

The compounds of the invention are generally selective ligands (agonists or antagonists) of alpha7 nicotinic receptors, which have little or no activity with respect to other nACh receptor subtypes, particularly α4β2 receptors. Exemplary 3-arylidene-anabaseine compounds include compounds with substituents on one or more of the three ring systems present; i.e., pyridyl, tetrahydropyridyl and 3-arylidene. It has been discovered that selection of a particular substituent to be placed on one of these rings can improve selectivity of binding for the alpha7 receptor and can also determine whether the occupied receptor will be activated or inhibited (i.e., whether the 3-arylidene-anabaseines described herein are agonists or antagonists of the alpha7 nicotinic receptor). For example, arylidenes at the 3-position of the tetrahydropyridyl ring expected to provide these properties include 3-benzylidene-anabaseines, cinnamylidene-anabaseines, benzofuran-2-ylmethylene-anabaseine, (1H-indol-2-ylmethylene)-anabaseines, and 3-benzylidene-glucuronide-anabaseines, as described in greater detail herein. These arylidenes may be further substituted on the phenyl ring of the 3-arylidene ($R^1$ in the formulae described herein) with 0-5 substituents, such as acetoxy, acetamido, amino, dimethylcarbamoyl, diethylcarbamoyl, methylcarbamoyl, ethylcarbamoyl, difluoromethoxy, dimethylaminopropoxy, hydroxy, $C_1$-$C_3$ alkoxy, trifluoromethoxy, methylamino or thiomethoxy. Surprisingly, substitution, particularly by $C_1$-$C_3$ alkyl at the alpha- or beta-oriented sites at positions 4, 5 and 6 of the tetrahydropyridyl ring form chiral products that display improved alpha7 receptor selectivity in comparison with non-alkylated versions of the same anabaseine. In addition, when the anabaseine compounds are enriched with a particular enantiomer, the enriched anabaseine shows surprisingly enhanced selectivity for the alpha7 nicotinic receptor when compared to the selectivity of the corresponding racemic substituted compounds, as described, for example, in Table 1. Combinations of substituents on two or all three different ring portions of these 3-arylidene-anabaseine compounds are expected to provide even greater selectivity than when they are made individually on just one of the three ring structures.

Particular 3-benzylidene-anabaseine compounds include:

3-(4-thiomethoxybenzylidene)-anabaseine 3-(4-(3-trimethylammoniumpropoxy)benzylidene)-anabaseine 3-(4-acetoxybenzylidene)-anabaseine 3-(2-acetoxybenzylidene)-anabaseine 3-(2,4-diacetoxybenzylidene)-anabaseine 3-(2-(3-pentoxy-4-methoxybenzylidene)-anabaseine 3-(4-acetamidobenzylidene)-anabaseine 3-(2-acetamidobenzylidene)-anabaseine 3-(2,4-diacetamidobenzylidene)-anabaseine 3(4-hydroxybenzylidene)-4-methyl-anabaseine 3(4-hydroxybenzylidene)-4'-methyl-anabaseine 3(4-hydroxybenzylidene)-5'-methyl-anabaseine 3(4-hydroxybenzylidene)-6'-methyl-anabaseine 3-(4-anthranoylbenzylidene)-anabaseine 3-(4-pivaloylbenzylidene)-anabaseine 3-(2-pivaloylbenzylidene)-anabaseine 3-(2,4-dipivaloylbenzylidene)-anabaseine Particular cinnamylidene-3-arylidene-anabaseine compounds include 3-(2,4-dimethoxycinnamylidene)-4-methyl-anabaseine 3-(2,4-dimethoxycinnamylidene)-5-methyl-anabaseine 3-(2,4-dimethoxycinnamylidene)-6-methyl-anabaseine 3-(2,4-dimethoxycinnamylidene)-4'-methyl-anabaseine 3-(2,4-diacetamidocinnamylidene)-6-methyl-anabaseine 3-(2,4-dihydroxycinnamylidene)-6-methyl-anabaseine Particular 3-(benzofuran-2-ylmethylene)-3-arylidene-anabaseine compounds include: 3-(Benzofuran-2-ylmethylene)-anabaseine.

Particular 3-(1H-Indol-2-ylmethylene)-3-arylidene-anabaseine compounds include: 3-(Indol-2-ylmethylene)-anabaseine.

A particular embodiment of the invention includes modified glucuronide metabolites of 3-arylidene-anabaseines; in particular where hydroxy functions at the para-position (as shown below) and/or ortho-position or on the carbohydrate unit are modified with a protecting group such as acetoxy (shown below) or methyl-esterified carboxyl group. A particular compound is 3-[4-(2,3,4-Triacetyl-6-methyl-B-glucuronidinyl)-2-methoxybenzylidene]-anabaseine:

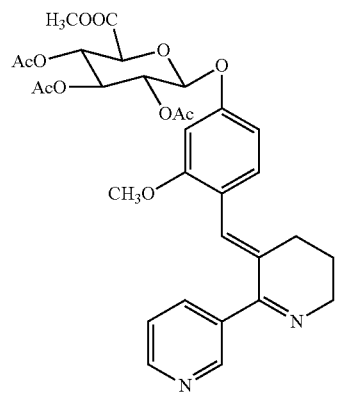

From a comparison of the eight possible carbon-methylated anabaseines synthesized in our laboratory, it was observed that twisting of the two anabaseine rings (as measured by NMR in aqueous solution) with respect to each other simultaneously reduces affinity and efficacy at the alpha7 receptor. Since coplanar orientation of unsubstituted anabaseine appears to be optimal for selective stimulation of the alpha7 receptor, it is believed that addition of an additional connection or bridge between one of the anabaseine rings and the 3-arylidene group would improve coplanarity of the bridged rings and also permanently place the two anabaseine nitrogen atoms into the most optimal, cisoid orientation for receptor binding. The 4'C on the pyridyl ring can be connected through an added methylene, ether O, S or other group, with the vinyl-bond forming methylene C linking the benzylidene group to the 3-position C on the tetrahydropyridyl ring; this forms a structure where the two N atoms on the anabaseine portion will be cisoid with respect to each other, and is expected to be the correct conformation for efficient receptor binding.

Accordingly, in another embodiment of the invention are provided bridged benzylidene-anabaseines of the structure shown below.

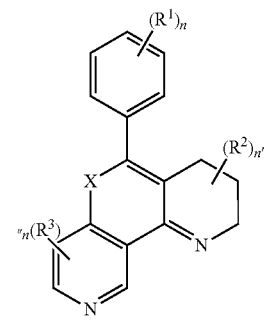

where $R^1$ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino or thiomethoxy and n is 0-5; $R^2$ is independently $C_1$-$C_3$ alkyl and n' is 0-3, $R^3$ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-3; X is $CH_2$, O, S, NH or $NR^8$, wherein $R^8$ is $C_1$-$C_5$ alkyl or $C_1$-$C_5$ alkylhydroxy; or a pharmaceutically acceptable salt, solvate, clathrate, stereoisomer, enantiomer, prodrug or combination thereof.

In some embodiments of the 3-bridged-benzylidene-anabaseines, n' is 1-3 and an $R^2$ is present at position 4, 5, or 6.

Although a benzylidene ring is shown in the structure above, the bridged structure could also lack the benzylidene, or have another arylmethylene substituent (cinnamylidene, etc.).

In particular embodiments, the 3-arylidene-anabaseine is an agonist of the alpha7 nicotinic receptor. In certain embodiments, the 3-arylidene-anabaseine is a partial agonist of the alpha7 nicotinic receptor. In certain embodiments, the 3-arylidene-anabaseine is a full agonist of the alpha7 nicotinic receptor. In certain of these embodiments, the 3-arylidene-anabaseine is a 3-benzylidene. In certain of these embodiments, the 3-arylidene-anabaseine is a 3-cinnamylidene. In others, the 3-arylidene-anabaseine is a 3-(benzofuran-2-ylmethylene)-anabaseine. In still others, the 3-arylidene-anabaseine is a 3-(1H-indol-2-ylmethylene)-anabaseine. In yet others, the 3-arylidene-anabaseine is a 3-benzylidene-glucuronide-anabaseine.

In certain of these embodiments, the agonist is 3-(3,4-(ethylenedioxy)benzylidene)-anabaseine, 3-(3,4-(methylenedioxy)benzylidene)-anabaseine, 3-((6-Methoxynaphth-2-yl)methylene)-anabaseine, or 3-((benzofuran-2-yl)methylene)-anabaseine. In certain embodiments, combinations of two or more of the foregoing may be used in the methods of treatment. In some embodiments, the anabaseine is 3-((benzofuran-2-yl)methylene)-anabaseine. In other embodiments, the anabaseine is 3-(3,4-(ethylenedioxy)benzylidene)-anabaseine or 3-(3,4-(methylenedioxy)benzylidene)-anabaseine. In particular embodiments, the anabaseine is 3-(4-thiomethoxybenzylidene)-anabaseine.

In certain embodiments, the 3-arylidene is an antagonist of the alpha7 nicotinic receptor. In certain of these embodiments, the 3-arylidene-anabaseine is a 3-benzylidene. In certain of these embodiments, the 3-arylidene-anabaseine is a 3-cinnamylidene-anabaseine. In others, the 3-arylidene-anabaseine is a 3-(benzofuran-2-ylmethylene)-anabaseine. In still others, the 3-arylidene-anabaseine is a 3-(1H-indol-2-ylmethylene)-anabaseine. In yet others, the 3-arylidene-anabaseine is a 3-benzylidene-glucuronide-anabaseine.

In particular embodiments, the phenyl ring of the 3-arylidene is substituted, valence permitting, by 0-5 $R^1$ (e.g., n is 0-5 for benzylidene-anabaseines and cinnamylidene-anabaseines, n is 0-4 for 3-(benzofuran-2-ylmethylene)-anabaseines, n is 0-4 for 3-(1H-indol-2-ylmethylene)-anabaseines, and n is 0-4 for 3-benzylidene-glucuronide-anabaseines, as previously described herein). In other embodiments, n is 0, 1, 2, 3, 4, or 5 (benzylidene/cinnamylidene-anabaseines only). In certain embodiments, n is 0-4, 0-3, 0-2, or 0-1. In still other embodiments, n is 1-5 (benzylidene/cinnamylidene-anabaseines only), 1-4, 1-3 or 1-2. In some embodiments, n is 0, 1, 2 or 3. In particular embodiments, n is 1, 2, or 3. In some embodiments, n is 1. In some embodiments, n is 2. In other embodiments, n is 3.

In certain embodiments of the 3-arylidenes, is $R^1$ is, independently, acetoxy, acetamido, $C_1$-$C_3$ alkyl, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkylhydroxy (e.g., —CH$_2$OH, —(CH$_2$)$_2$OH, —(CH$_2$)$_3$ OH), hydroxy, $C_1$-$C_3$ alkoxy, trifluoromethoxy, methylamino or thiomethoxy. In some embodiments, $R^1$ may be independently, hydroxy, amino, methylamino, thiomethoxy, or $C_1$-$C_3$ alkoxy, including combinations of the foregoing (where n is 2 or more), and including where $R^1$ may be the same or different (e.g., $R^1$ is methoxy and n is 2 or 3, etc.; where $R^1$ is methoxy and hydroxy and n is 2 or 3, or more;

where $R^1$ is thiomethoxy and n is n is 2 or 3, or more; etc.). In certain of these embodiments, n is 0, 1, 2, 3, or 4. In some embodiments, n is 0, 1, 2 or 3. In particular embodiments, n is 1, 2, or 3. In some embodiments, n is 1. In some embodiments, n is 2. In other embodiments, n is 3. In certain embodiments, the 3-arylidene-anabaseine is a 3-benzylidene-anabaseine. In certain embodiments, the 3-arylidene-anabaseine is a 3-benzylidene-anabaseine substituted by a $C_1$-$C_3$ alkyl on the tetrahydropyridyl ring. In certain embodiments, the 3-arylidene-anabaseine is a 3-benzylidene-glucuronide-anabaseine. In certain embodiments, the 3-arylidene-anabaseine is a 3-benzylidene-glucuronide-anabaseine substituted by a $C_1$-$C_3$ alkyl on the tetrahydropyridyl ring.

In particular embodiments, at least one $R^1$ is, independently, $C_1$-$C_3$ alkoxy, thiomethoxy, or dimethylcarabamoyl.

In particular embodiments, at least one $R^1$ is, independently, $C_1$-$C_3$ alkoxy (e.g., methoxy, ethoxy, or propoxy (including e.g., isopropoxy)). In particular embodiments, at least one $R^1$ is methoxy or isopropoxy. In some embodiments, at least one $R^1$ is methoxy. In still other embodiments, at least one $R^1$ is isopropoxy. In some embodiments, at least one $R^1$ is thiomethoxy. In some embodiments, at least one $R^1$ is dimethylcarbamoyl, diethylcarbamoyl, methylcarbamoyl, or ethylcarbamoyl. In certain of these embodiments, n is 1, 2, 3, 4, or 5. In particular embodiments, n is 1-3. In certain embodiments n is 2.

In certain embodiments, the 3-arylidene-anabaseine is a 3-benzylidene. In certain of these embodiments, the 3-arylidene-anabaseine is a 3-cinnamylidene. In others, the 3-arylidene-anabaseine is a 3-(benzofuran-2-ylmethylene)-anabaseine. In still others, the 3-arylidene-anabaseine is a 3-(1H-indol-2-ylmethylene)-anabaseine. In yet others, the 3-arylidene-anabaseine is a glucuronide-benzylidene-anabaseine. In some of these embodiments, $R^1$ may be independently, hydroxy, amino, methylamino, thiomethoxy, or methoxy, including combinations of the foregoing (where n is 2 or more), and including where $R^1$ may be the same or different (e.g., $R^1$ is methoxy and n is 2 or 3, etc.; where $R^1$ is methoxy and hydroxy and n is 2 or 3, or more; where $R^1$ is thiomethoxy and n is n is 2 or 3, or more; etc.). In particular embodiments, $R^1$ is thiomethoxy and n is 1, 2, or 3. In particular embodiments, at least one $R^1$ is thiomethoxy and n is 1, 2, or 3. In particular embodiments, at least one $R^1$ is thiomethoxy and a different $R^1$ is methylamino, and n is 1, 2, or 3.

In particular embodiments, $R^1$ is, independently, hydroxy, amino, methylamino, thiomethoxy, or $C_1$-$C_3$ alkoxy, including combinations of the foregoing (where n is 2 or more), and including where $R^1$ may be the same of different (e.g., $R^1$ is methoxy and n is 2 or 3, etc.).

In certain of embodiments, n is 1 or 2 and $R^1$ is $C_1$-$C_3$ alkoxy. In certain embodiments, n is 1 or 2 and $R^1$ is, independently, methoxy or isopropoxy. In certain embodiments, n is 2 and $R^1$ is, independently, methoxy or isopropoxy (e.g., both $R^1$ are methoxy, both $R^1$ are isopropoxy, or one $R^1$ is methoxy and the other is isopropoxy). In certain embodiments, $R^1$ includes hydroxy. In particular embodiments, n is one and $R^1$ is hydroxy.

In particular embodiments of the 3-arylidene-anabaseines, n is 2 and $R^1$ may be, independently, acetoxy, acetamido, amino, methylamino, dimethylamino, dimethylcarbamoyl, diethylcarbamoyl, methylcarbamoyl, ethylcarbamoyl, difluoromethoxy, dimethylaminopropoxy, hydroxyl, $C_1$-$C_5$ alkoxy (e.g., methoxy, isopropoxy, etc. and including $C_3$-$C_5$ isoalkoxy), trifluoromethoxy, methylamino or thiomethoxy, wherein at least one $R^1$ is methylamino or dimethylcarbamoyl. In particular embodiments, the 3-arylidene is a benzylidene. In certain embodiments, the two $R^1$ are at positions 2" and 4" on the benzylidene ring. In particular embodiments, both $R^1$ are methylamino. In other embodiments, both $R^1$ are dimethylcarbamoyl. In some embodiments, one $R^1$ is methylamino and the other $R^1$ is acetoxy, acetamido, amino, dimethylcarbamoyl, diethylcarbamoyl, methylcarbamoyl, ethylcarbamoyl, difluoromethoxy, dimethylaminopropoxy, hydroxy, $C_1$-$C_3$ alkoxy (e.g., methoxy, isopropoxy, etc.), trifluoromethoxy, or thiomethoxy. In other embodiments, one $R^1$ is dimethylcarbamoyl and the other $R^1$ is acetoxy, acetamido, amino, methylamino, dimethylaminopropoxy, hydroxy, $C_1$-$C_3$ alkoxy (e.g., methoxy, isopropoxy, etc.), trifluoromethoxy, or thiomethoxy. In certain embodiments, one $R^1$ is dimethylcarbamoyl and the other $R^1$ is methoxy or ispopropoxy. In certain embodiments, one $R^1$ is methylamino and the other $R^1$ is methoxy or ispopropoxy. In certain of these embodiments, the dimethylcarbamoyl is at the 2" position. In certain of these embodiments, the dimethylcarbamoyl is at the 4" position. In certain of these embodiments, the dimethylcarbamoyl, diethylcarbamoyl, methylcarbamoyl, or ethylcarbamoyl is at the 4" position. In certain of these embodiments, the methoxy is at the 2" position. In certain of these embodiments, the methoxy is at the 4" position.

In particular embodiments, the pyridyl ring of the 3-arylidene-anabaseine is substituted, by 0-3 $R^3$ (e.g., n" is 0-3). In other embodiments, n" is 0, 1, 2, or 3. In certain embodiments, n" is 0-3, 0-2, or 0-1. In still other embodiments, n" is 1-3 or 1-2. In some embodiments, n" is 0, 1, 2 or 3. In particular embodiments, n" is 1, or 2. In some embodiments, n" is 1. In some embodiments, n" is 2. In other embodiments, n" is 3.

In some embodiments, $R^3$ is, independently, $C_1$-$C_3$ alkyl, $C_1$-$C_3$ alkylhydroxy, $C_1$-$C_3$ alkoxy, cyano, halo, phenoxy, phenyl, pyridyl or benzyl.

In certain embodiments, n" is 3 and $R^3$ are present at the 4', 5' and 6' positions of the pyridyl ring. In other embodiments, n" is 1 and $R^2$ is present at the 4', 5' or 6' position. In still other embodiments, n" is 2 and $R^3$ are present at the 4' and 5', 4' and 6', or 5' and 6' positions. In certain embodiments, n" is 1 and $R^3$ is present at the 4' position. In certain embodiments, n" is 1 and $R^3$ is present at the 5' position. In certain embodiments, n" is 1 and $R^3$ is present at the 6' position. In certain of these embodiments, n is 1 or 2 and $R^1$ is, independently, $C_1$-$C_3$ alkoxy. In certain embodiments, n is 1 or 2 and $R^1$ is, independently, methoxy or isopropoxy. In certain embodiments, n is 2 and $R^1$ is, independently, methoxy or isopropoxy (e.g., both $R^1$ are methoxy, both $R^1$ are isopropoxy, or one $R^1$ is methoxy and the other is isopropoxy). In certain embodiments, $R^1$ includes hydroxy. In particular embodiments, n is one and $R^1$ is hydroxy. In certain embodiments, $R^1$ is, independently, hydroxy, amino, methylamino, thiomethoxy, or $C_1$-$C_3$ alkoxy.

In particular embodiments of the 3-(1H-Indol-2-ylmethylene)-anabaseine compounds, $R^7$ is hydrogen, $C_1$-$C_5$ alkyl (e.g., methyl, ethyl, pentyl, etc.), $C_1$-$C_5$ dialkoxy, or $C_1$-$C_5$ alkoxy. In some embodiments, $R^7$ is hydrogen or $C_1$-$C_5$ alkyl. In some embodiments, $R^7$ is hydrogen. In other embodiments, $R^7$ is methyl, ethyl, propyl or pentyl. In certain embodiments, the $C_1$-$C_5$ alkoxy is optionally further substituted by halo, $C_1$-$C_5$ alkyl, etc.

In certain embodiments, the anabaseine compound is a 3-cinnamylidene-anabaseine as described herein.

In certain embodiments, the anabaseine compound is a 3-benzylidene-anabaseine as described herein (e.g., tetrahydropyridyl-alkylated-benzylidene-anabaseine, bridged benzylidene-anabaseine, disubstituted (at phenyl of benzylidene)-benzylidene-anabaseine or modified benzylidene-glucuronide-anabaseine as described herein).

In certain embodiments, the anabaseine compound is a 3-((benzofuran-2-yl)methylene)-anabaseine as described herein.

In other embodiments, the anabaseine compound is a 3-((1J-indol-2-yl)methylene)anabaseine as described herein.

In some embodiments, the anabaseine compound is 6-methyl-anabaseine; dimethoxy)-benzylidene)-4-methyl-anabaseine, 3-(4-Hydroxybenzylidene)-4-methyl-anabaseine; 3-(2,4-dimethoxy)-benzylidene)-5-methyl-anabaseine, or 3-(2,4-dimethoxy)-benzylidene)-6-methyl-anabaseine. In certain embodiments, the anabaseine compound is 3-(2,4-dimethoxy)-benzylidene)-4-methyl-anabaseine, 3-(4-Hydroxybenzylidene)-4-methyl-anabaseine; dimethoxy)-benzylidene)-5-methyl-anabaseine, or 3-(2,4-dimethoxy)-benzylidene)-6-methyl-anabaseine.

The following new 3-(di-substituted benzylidene)-anabaseines are expected to have improved efficacy compared with GTS-21, considering that at least two polar benzylidene substituents improve efficacy.

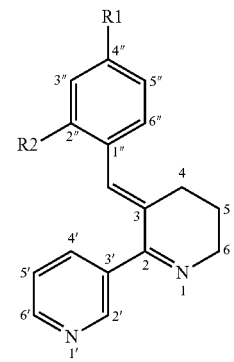

|  | R1 | R2 |
|---|---|---|
| Bis-compounds | | |
| 1 | methylamino | methylamino |
| 2 | amino | amino |
| 3 | acetoxy | acetoxy |
| 4 | isopropoxy | isopropoxy |
| 5 | acetamido | acetamido |
| 6 | dimethylcarbamate | dimethylcarbamate |
| Mixed-compounds | | |
| 7 | methoxy | methylamino |
| 8 | isopropoxy | methylamino |
| 9 | methoxy | amino |
| 10 | isopropoxy | amino |
| 11 | methoxy | pivaloyloxy |
| 12 | isopropoxy | pivaloyloxy |
| 13 | methoxy | dimethylcarbamate |
| 14 | isopropoxy | dimethylcarbamate |
| 15 | methoxy | acetamido |
| 16 | isopropoxy | acetamido |

It is expected that removal of certain metabolically labile groups on some of these compounds will expose other active substituents and that some of these compounds may also possess good pharmacological activity. Synthesis of the compounds is expected to involve routine procedures well-known to those skilled in the art. In general, the appropriate benzaldehyde will be prepared by routine alkylation, esterification or amidation reaction methods.

Cinnamylidene-anabaseine compounds with expected improved activities will also be prepared. 3-(Dimethylaminocinnamylidene)-anabaseine (DMACA) displays higher alpha7 affinity and efficacy than 3-(Dimethylaminobenzylidene)-anabaseine (DMABA) and DMABA. New compounds based on DMAC-anabaseine would also be expected to have the same lack of toxicity as the benzylidene-anabaseines. The following shows the structure of the new compounds, the synthesis of which requires only routine skill in the art.

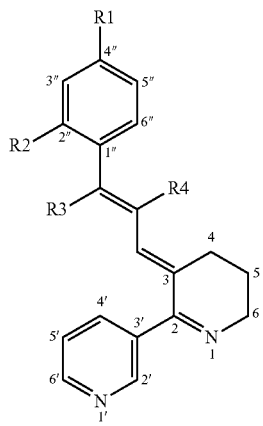

| Cpd | R1 | R2 | R3 | R4 |
|---|---|---|---|---|
| 17 | methoxy | methoxy | hydrogen | hydrogen |
| 18 | methoxy | methoxy | methyl | methyl |
| 19 | hydrogen | dimethylamino | hydrogen | hydrogen |
| 20 | hydrogen | dimethylamino | methyl | methyl |
| 21 | hydroxyl | hydroxyl | hydrogen | hydrogen |
| 22 | hydroxyl | hydroxyl | methyl | methyl |

3-Arylidene-Anabaseines with Alkyl Substitution

Contrary to what was initially expected from analogous substitution experiments with nicotine, it was observed that alkylation of individual carbons in otherwise unsubstituted anabaseines sometimes caused remarkable losses in affinity for the alpha7 and alpha4beta2 receptors. This was particularly the case for methyl substitutions at the 3-position of the tetrahydropyridyl ring, and the 2' and 4'-positions of the pyridyl ring of anabaseine. Thus, it was surprising that methylations at available carbon atoms on the tetrahydropyridyl ring of the substituted anabaseine structure on the available ring carbons (particularly at the 4, 5 and 6 positions), would lead to compounds with unpredicted improvements, including alpha7 receptor affinity and selectivity of binding. Addition of a methyl substituent at the 6-position of the THP ring preferentially reduces alpha4beta2 receptor affinity, whereas substituting a methyl at the 6' position on the pyridyl ring preferentially reduces alpha7 nAChR affinity and also produces a >90% loss of efficacy in activating the alpha7 receptor (the alpha4beta2 receptor efficacy is unchanged by this substitution). Methyl substitutions at the 2', 4', and 3 positions cause very drastic decreases in alpha7 and alpha4beta2 receptor affinity and efficacy due to at least two different factors: altering stability of the active cyclic iminium forms of the anabaseine compound, and second, interfering with close contacts within the binding site of the nAChR.

When alkylation of the tetrahydropyridyl ring carbons is coupled with substitution of the tetrahydropyridyl ring at position 3 with an arylidene (including where the arylidene ring itself may be additionally substituted), for example, as in 2, 4-dimethoxybenzylidene, p-hydroxy-benzylidene, p-amino-benzylidene, or (benzofuran-2-yl)methylene groups at the 3-position, this leads to compounds with unpredicted improvements, including alpha7 receptor affinity and selectivity of binding relative to DMXB-anabaseine and related arylidene-anabaseine compounds in which the tetrahydropyridyl and pyridyl anabaseine rings are otherwise unsubstituted.

For example, while 4'-methyl-anabaseine displayed significantly diminished nAChR agonistic or binding activity, relative to anabaseine or DMXBA, a significant improvement (>10-fold) in alpha7 selectivity was observed relative to DMXBA when the DMXB group was attached to the 3-position of the methylated-anabaseine (e.g., 4-methyl-DMXBA, 5-methyl-DMXBA, 6-methyl-DMXBA). Improvements in selectivity, binding affinity, etc. of the new anabaseine compounds in comparison to DMXBA represent a significant step forward in the possible development of therapeutic products, because DMXBA, as is known to those of skill in the field, is a promising anabaseine compound under development in the fields of cognition enhancement and the treatment of neurodegenerative conditions.

Although alkylation (e.g., methylation, etc.) of individual carbons in the tetrahydropyridyl and pyridyl rings of the anabaseine compounds did not lead to an enhancement of agonist activity at central nicotinic receptors including alpha7 and alpha4beta2 types involved in various mental processes, some methylations at the available carbon atoms on the tetrahydropyridyl ring of the anabaseine structure lead to compounds with unpredicted improvements in alpha7 receptor affinity and selectivity of binding relative to GTS-21 and related compounds. Particularly, alkylation at positions 4', 4, 5 and/or 6, when coupled with addition of 2,4-dimethoxybenzylidene, para-hydroxy-benzylidene or para-amino-benzylidene groups at the 3-position provided unexpected increases in alpha7 receptor affinity and selectivity, as demonstrated by the data provided in Table 1.

Additionally, potency ($EC_{50}$), and receptor selectivity are both affected by the THP (tetrahydropyridyl) ring substituents at positions 4, 5 and 6. The anticipated therapeutic advantage of applying a single high affinity (for alpha7) enantiomer is that adverse side effects of the relatively low affinity enantiomer at other nAChR subtypes, including alpha4beta2 and other sites, on the alpha 7 receptor will be minimized. Regarding the latter site of action, we have recently shown that many benzylidene-anabaseines also enter the nAChR ion channel to cause block of ion flux through the channel, usually at higher concentrations than cause channel opening (Arias et al., submitted). Since both DMXB-methylanabaseine enantiomers bind equally well within the ion channel, it can be predicted that application of the enantiomer displaying high affinity for the ACh binding site on the alpha7 receptor, rather than the racemic compound, should produce a greater activating effect on this receptor and less adverse effect. Since channel blockers generally show little structural specificity and block a variety of related ion channels (other ligand-gated channels including GABA and glycine receptors), alpha7 agonists which display less channel blocking activity at otherwise effective concentrations are expected to be safer drugs.

For example, in some embodiments of the 3-benzylidene-anabaseines, the anabaseine is 4-methyl-DMXBA. In certain embodiments the 4-methyl-DMXBA is enriched in the one enantiomer that has a shorter retention time on a Chiracel OJ-H column than the other enantiomer. This enantiomer displayed a relative alpha7 nAChR (versus alpha4beta2) receptor binding selectivity that was 6.5-fold higher than that of the other enantiomer (See Table 1). In other embodiments, 4-methyl-DMXBA is enriched in the one enantiomer, which had a longer retention time on a Chiracel OJ-H column than the other enantiomer. The relative alpha7 nAChR binding selectivity of this enantiomer was similar (1.28) to unmethylated DMXBA (1.00). The first, enantiomer, on the basis of its binding properties to rat brain nAChR, would be predicted to be twice as potent as the racemic compound. Also, because of the greater nAChR selectivity of this faster eluting species, it would also be predicted to be less likely to produce adverse side effects related to alpha4beta2 nAChR In some embodiments, the relative alpha7 receptor/alpha4beta2 receptor selectivity of the enantiomerically enriched 3-arylidene-anabaseine compound is about 2 times (i.e., about 2×), about 5×, about 6×, about 7×, about 8×, about 9×, about 10×, about 12×, about 14×, about 15×, about 18×, about 20×, about 25×, about 30×, about 40×, about 50×, about 60×, about 70×, about 80×, about 90×, about 100×, or about 150× more selective than the relative alpha7 receptor/alpha4beta2 receptor selectivity of DMXBA measured under the same conditions. In particular embodiments, relative selectivity is as described in Example 1 herein. In certain of these embodiments, the enantiomerically enriched 3-arylidene-anabaseine compound is enriched in the S-isomer. In others, the enantiomerically enriched 3-arylidene-anabaseine compound is enriched in the R-isomer. In certain of these embodiments of 4-methyl-DMXBA, 5-methyl-DMXBA, or 6-methyl-DMXBA, the anabaseine compound is enriched in the most selective enantiomer, which has a shorter retention time on a Chiracel OJ-H column, in particular when measured as described herein.

In some embodiments, the relative alpha7 receptor/alpha4beta2 receptor selectivity of the enantiomerically enriched 3-arylidene-anabaseine compound, which is the more selective enantiomer, is about 2 times (i.e., about 2×), about 5×, about 6×, about 7×, about 8×, about 9×, about 10×, about 12×, about 14×, about 15×, about 18×, about 20×, about 25×, about 30×, about 40×, about 50×, about 60×, about 70×, about 80×, about 90×, about 100×, or about 150× more selective than the relative alpha7 receptor/alpha4beta2 receptor selectivity of the racemic mixture of the same anabaseine compound, measured under the same conditions. In particular embodiments, relative selectivity is as described in Example 1 herein. In certain of these embodiments, the enantiomerically enriched 3-arylidene-anabaseine compound is enriched in the S-isomer. In others, the enantiomerically enriched 3-arylidene-anabaseine compound is enriched in the R-isomer. In certain embodiments of 4-methyl-DMXBA, 5-methyl-DMXBA, or 6-methyl-DMXBA, the anabaseine compound is enriched in the most selective enantiomer, which has a shorter retention time on a Chiracel OJ-H column, in particular when measured as described herein.

In some embodiments, the relative alpha7 receptor/alpha4beta2 receptor selectivity of the enantiomerically enriched 3-arylidene-anabaseine compound, which is the more selective enantiomer, is about 2 times (L e., about 2×), about 5×, about 6×, about 7×, about 8×, about 9×, about 10×, about 12×, about 14×, about 15×, about 18×, about 20×, about 25×, about 30×, about 40×, about 50×, about 60×, about 70×, about 80×, about 90×, about 100×, or about 150× more selective than the relative alpha7 receptor/alpha4beta2 receptor selectivity of the opposite enantiomer (less selective enantiomer) of the same anabaseine compound, measured under the same conditions. In particular embodiments, relative selectivity is as described in Example 1 herein. In certain of these embodiments, the enantiomerically enriched more selective 3-arylidene-anabaseine compound is enriched in the S-isomer. In others, the enantiomerically enriched more selective 3-arylidene-anabaseine compound is enriched in the R-isomer. In certain embodiments of 4-methyl-DMXBA, 5-methyl-DMXBA, or 6-methyl-DMXBA, the anabaseine compound is enriched in the most selective enantiomer, which has a shorter retention time on a Chiracel OJ-H column, in particular when measured as described herein.

In certain embodiments are provided 3-arylidene-anabaseines, as described herein, which are substituted with $C_1$-$C_3$ alkyl at the 4, 5, or 6 position of the tetrahydropyridyl ring (corresponding to $(R^2)_{n'}$). In particular embodiments, there is one alkyl group at position 4 (i.e., n'=1). In other embodiments, there is one alkyl group at position 5. In still other embodiments there is one alkyl group at position 6. In particular embodiments, n' is 2 or n' is 3. In some of these embodiments, the alkyl group is methyl. In other embodiments, the alkyl group is ethyl. In still other embodiments, the alkyl group is propyl. In particular of these embodiments, the phenyl ring of the arylidene is substituted, valence permitting, by 0-5 $R^1$ (e.g., n is 0-5 for benzylidene-anabaseines/cinnamylidene-anabaseines; n is 0-4 for 3-(benzofuran-2-ylmethylene)-anabaseines, n is 0-4 for 3-(1H-indol-2-ylmethylene)-anabaseines, and n is 0-4 for 3-benzylidene-glucuronide-anabaseines (as previously described herein)). In other embodiments, n is 0, 1, 2, 3, 4, or 5 (benzylidene/cinnamylidene-anabaseines only). In certain embodiments, n is 0-4, 0-3, 0-2, or 0-1. In still other embodiments, n is 1-5 (benzylidene/cinnamylidene-anabaseines only), 1-4, 1-3 or 1-2. In particular embodiments, $R^1$ is, independently, hydroxy, amino, methylamino, thiomethoxy, or methoxy, including combinations of the foregoing (where n is 2 or more), and including where $R^1$ may be the same of different (e.g., $R^1$ is methoxy and n is 2 or 3, etc.). In certain of these embodiments, n is 1 or 2 and $R^1$ is $C_1$-$C_3$ alkoxy. In certain embodiments, n is 1 or 2 and $R^1$ is, independently, methoxy or isopropoxy. In certain embodiments, n is 2 and $R^1$ is, independently, methoxy or isopropoxy (e.g., both $R^1$ are methoxy, both $R^1$ are isopropoxy, or one $R^1$ is methoxy and the other is isopropoxy). In certain embodiments, $R^1$ includes hydroxy. In particular embodiments, n is 1 and $R^1$ is hydroxy. In certain of these embodiments, the 3-arylidene-anabaseine is enriched in the R-isomer. In other embodiments the 3-arylidene-anabaseine is enriched in the S-isomer.

In certain embodiments are provided 3-benzylidene-anabaseines, as described herein, which are substituted with $C_1$-$C_3$ alkyl at the 4, 5, or 6 position of the tetrahydropyridyl ring (corresponding to $(R^2)_{n'}$). In particular embodiments, there is one alkyl group at position 4 (i.e., n'=1). In other embodiments, there is one alkyl group at position 5. In still other embodiments there is one alkyl group at position 6. In particular embodiments, n' is 2 or n' is 3. In some of these embodiments, the alkyl group is methyl. In other embodiments, the alkyl group is ethyl. In still other embodiments, the alkyl group is propyl. In certain of these embodiments, the benzylidene ring is substituted by 0-5 $R^1$ (i.e., n=0-5). In other embodiments, n is 0, 1, 2, 3, 4, or 5. In certain embodiments, n is 0-4, 0-3, 0-2, or 0-1. In still other embodiments, n is 1-5, 1-4, 1-3 or 1-2. In particular embodiments, $R^1$ is, independently, hydroxy, amino, methylamino, thiomethoxy, or methoxy, including combinations of the foregoing (where n is 2 or more), and including where $R^1$ may be the same of different (e.g., $R^1$ is methoxy and n is 2 or 3, etc.). In certain of these embodiments, n is 1 or 2 and $R^1$ is $C_1$-$C_3$ alkoxy. In certain embodiments, n is 1 or 2 and $R^1$ is, independently, methoxy or isopropoxy. In certain embodiments, n is 2 and $R^1$ is, independently, methoxy or isopropoxy (e.g., both $R^1$ are methoxy, both $R^1$ are isopropoxy, or one $R^1$ is methoxy and the other is isopropoxy). In certain embodiments, $R^1$ includes hydroxy. In particular embodiments, n is one and $R^1$ is hydroxy. In certain embodiments, the 3-benzylidene-anabaseine is enriched in the R-isomer. In other embodiments the 3-benzylidene-anabaseine is enriched in the S-isomer.

In some embodiments of the 3-arylidene-anabaseines, $R^1$ is methoxy, n is 2, $R^2$ is methyl, n' is 1, n" is 0 and $R^4$ is H. In certain of these embodiments, the 3-arylidene-anabaseine is enriched in the R-isomer. In other embodiments the 3-arylidene-anabaseine is enriched in the S-isomer.

In certain embodiments, the 3-arylidene-anabaseine is a 3-benzylidene-anabaseine and $R^1$ is methoxy, n is 2, $R^2$ is methyl, n' is 1, n" is 0 and $R^4$ is H. In certain of these embodiments, the 3-benzylidene-anabaseine is 4-methyl-DMXBA. In other embodiments, the 3-benzylidene-anabaseine is 5-methyl-DMXBA. In still other embodiments, the 3-benzylidene-anabaseine is 6-methyl-DMXBA. In certain of these embodiments, the 4-methyl-DMXBA is enriched in the R-isomer. In others, the 4-methyl-DMXBA is enriched in the S-isomer. In other embodiments, the 5-methyl-DMXBA is enriched in the R-isomer. In others, the 5-methyl-DMXBA is enriched in the S-isomer. In still other embodiments, the 6-methyl-DMXBA is enriched in the R-isomer. In others, the 6-methyl-DMXBA is enriched in the S-isomer.

In some embodiments of the 3-arylidene-anabaseines, $R^1$ is hydroxy, n is 1, $R^2$ is methyl, n' is 1, n" is 0 and $R^4$ is H. In certain of these embodiments, the 3-arylidene-anabaseine is enriched in the R-isomer. In other embodiments the 3-arylidene-anabaseine is enriched in the S-isomer.

In certain embodiments, the 3-arylidene-anabaseine is a benzylidene-anabaseine and $R^1$ is hydroxy, n is 1, $R^2$ is methyl, n' is 1, n" is 0 and $R^4$ is H. In certain of these embodiments, the 3-benzylidene-anabaseine is 3-(4-hydroxybenzylidene)-4-methylanabaseine. In certain of these embodiments, the 3-benzylidene-anabaseine is 3-(4-hydroxybenzylidene)-6-methylanabaseine. In certain of these embodiments, the 3-benzylidene-anabaseine is enriched in the R-isomer. In other embodiments the 3-benzylidene-anabaseine is enriched in the S-isomer.

Replacement of a hydrogen with an alkyl (methyl, ethyl or propyl) group at the methylene C, which links the benzylidene group to the 3-position C on the tetrahydropyridyl ring, also is expected to effect alpha7 binding selectivity.

Thus in certain embodiments are provided 3-arylidenes where $R^4$ is $C_1$-$C_3$ alkyl or $C_1$-$C_3$ alkylhydroxy. In some embodiments are provided 3-arylidenes where $R^5$ is $C_1$-$C_3$ alkyl. In some embodiments are provided 3-arylidenes where $R^6$ is $C_1$-$C_3$ alkyl. In certain embodiments, $R^4$, $R^5$, and $R^6$ are hydrogen. In certain embodiments $R^4$ is hydrogen. In other embodiments $R^4$ is methyl. In certain embodiments $R^5$ is hydrogen. In other embodiments $R^5$ is methyl. In certain embodiments $R^6$ is hydrogen. In other embodiments $R^6$ is methyl. In certain embodiments, $R^4$ is hydrogen and, where present, $R^5$ and/or $R^6$ are hydrogen. In certain embodiments $R^4$ is methylhydroxy, ethylhydroxy, or propylhydroxy. In certain embodiments $R^4$ is hydrogen, methylhydroxy, ethylhydroxy, or propylhydroxy.

In particular embodiments of the 3-(1H-Indol-2-ylmethylene)-anabaseine compounds, $R^7$ is hydrogen, $C_1$-$C_5$ alkyl (e.g., methyl, ethyl, pentyl, etc.), $C_1$-$C_5$ dialkoxy, or $C_1$-$C_4$ alkoxy. In some embodiments, $R^7$ is hydrogen or $C_1$-$C_5$ alkyl. In some embodiments, $R^7$ is hydrogen. In other embodiments, $R^7$ is methyl, ethyl, propyl or pentyl. In certain embodiments, the $C_1$-$C_4$ alkoxy is optionally further substituted.

As is clearly demonstrated by the data in Table 1, the orientation (chirality) of the alkyl group at positions 4, 5 or 6 of the tetrahydropyridyl ring is also important for alpha7 versus alpha4beta2 selectivity. The data in Table 1 was obtained by resolution and subsequent characterization of the enantiomerically enriched compounds obtained by chiral chromatography of the racemic 4, 5, or 6-methyl-DMXBA compounds.

Thus, in certain embodiments are provided 3-arylidene-anabaseines as described herein, where the anabaseine includes a $C_1$-$C_3$ alkyl substituent on the tetrahydropyridyl ring. In particular of these embodiments, the 3-arylidene-anabaseines is enriched in the R-isomer. In other embodiments, the 3-arylidene-anabaseine is enriched in the S-isomer. In certain of these embodiments, the arylidene is a benzylidene-anabaseine, a 3-cinnamylidene-anabaseine a 3-(benzofuran-2-ylmethylene)-anabaseine, a 3-(1H-indol-2-ylmethylene)-anabaseine, or a glucuronide-benzylidene-anabaseine, as described herein. In certain embodiments, the 3-arylidene-anabaseine is a benzylidene. In certain of these embodiments, the 3-arylidene-anabaseine is a 3-cinnamylidene. In others, the 3-arylidene-anabaseine is a 3-(benzofuran-2-ylmethylene)-anabaseine. In still others, the 3-arylidene-anabaseine is a 3-(1H-indol-2-ylmethylene)-anabaseine. In yet others, the 3-arylidene-anabaseine is a 3-benzylidene-glucuronide-anabaseine. In some of these embodiments, $R^1$ may be independently, hydroxy, amino, methylamino, thiomethoxy, or methoxy, including combinations of the foregoing (where n is 2 or more), and including where $R^1$ may be the same or different (e.g., $R^1$ is methoxy and n is 2 or 3, etc.; where $R^1$ is methoxy and hydroxy and n is 2 or 3, or more; where $R^1$ is thiomethoxy and n is n is 2 or 3, or more; etc.). In particular embodiments, $R^1$ is thiomethoxy and n is 1, 2, or 3. In other embodiments, at least one $R^1$ is thiomethoxy and n is 1, 2, or 3. In particular embodiments, at least one $R^1$ is thiomethoxy and a different $R^1$ is methylamino, and n is 1, 2, or 3. In certain of these embodiments, n is 1 or 2 and $R^1$ is $C_1$-$C_3$ alkoxy. In certain embodiments, n is 1 or 2 and $R^1$ is, independently, methoxy or isopropoxy. In certain embodiments, n is 2 and $R^1$ is, independently, methoxy or isopropoxy (e.g., both $R^1$ are methoxy, both $R^1$ are isopropoxy, or one $R^1$ is methoxy and the other is isopropoxy). In certain embodiments, $R^1$ includes hydroxy. In particular embodiments, n is one and $R^1$ is hydroxy.

In addition to the use of chiral chromatography, separation of enantiomers can be achieved by methods well known to the skilled artisan, such as, for example, fractional crystallization with optically active salts.

Separation by chiral chromatography is well understood in the field, particular in light of the teaching provided herein. The use of chiral chromatography for the separation of racemic mixtures or 3-arylidene-anabaseines is described in more detail herein.

The 3-arylidene-anabaseine enantiomers can also be synthesized by methods well known to those skilled in the art, including preparation of the appropriate chiral methyl-piperidone precursor of the tetrahydropyridyl ring. Both traditional asymmetric synthesis and biocatalysis approaches will yield the required chiral precursors for synthesis of a large variety of substituted benzylidene-anabaseine, benzofuran-2-yl-methylene-anabaseine, and cinnamylidene-anabaseines displaying significantly enhanced alpha7 selectivity. Furthermore, other chiral substituents at the 4, 5, or 6 positions are expected to also display different Alpha7 nAChr selectivities and efficacies. Besides asymmetric synthesis, the individual enantiomers may also be obtained by fractional crystallization of a chiral salt or by chiral chromatography.

3-Arylidene-Anabaseine Metabolites

The metabolism of DMXBA has been studied in the rat, dog, and human. The primary metabolites are O-demethylated products that are excreted as glucuronic acid conjugates. The three main metabolites in rat urine are the 4-hydroxy- DMXBA and 2-hydroxy-DMXBA glucuronides and to a lesser extent unconjugated 4-hydroxy-DMXBA. DMXBA is rapidly absorbed and distributed to the brain and other organs after oral administration. Most of the administered DMXBA is excreted in the feces as the above-mentioned metabolites. As demonstrated herein, these glucuronides are even more selective (>10-fold relative to DMXBA) and efficacious partial agonists on the human alpha7 receptor than the parent compound. Lipophilic derivatives of these polar drug metabolites should enter the brain and permit selective alpha7 nAChR stimulation. Alternately, conjugation of the polar metabolite to small organic moieties (such as aromatic carboxylic acids), peptides or proteins that have carrier-mediated passage across the blood-brain barrier should facilitate their entry into the brain. Thus a variety of analogs of arylidene-anabaseine polar metabolites may be useful drugs. Polar metabolites of DMXBA and related arylidene-anabaseines that do not pass across the blood-brain barrier could also be used to target peripherally-distributed alpha7 receptors such as are found on macrophages, vascular endothelium and bronchial epithelium.

Methods of Preparation of 3-Arylidene-Anabaseines

Generally, the 3-arylidene-anabaseines may be prepared using synthetic methods known to the skilled artisan, particular in view of the teaching provided herein, for example, as described in U.S. Pat. Nos. 5,581,785; 5,741,802; 5,977,144; 5,602,257; 5,840,906, 5,734,059 and 6,630,491 and in the scientific literature (Kem et al., 1971; Kern, 1973; Zoltewicz et al., 1989; Kern et al., 2004.), which are incorporated herein by reference in their entirety. Basically, a slight excess of the selected aryl aldehyde is dissolved in a weakly acidic ethanolic solution of the appropriate anabaseine and then refluxed for several hours depending on the reactivity of the aldehyde. The resulting product can be precipitated with a less polar solvent such as ether and then recrystallized, or otherwise purified by silica gel or reversed-phase low pressure or high pressure chromatography. Particular synthetic methods are also set forth in the Examples.

Pharmaceutical Compositions

In another aspect, the present invention provides pharmaceutical formulations for treatment of individuals in need thereof, comprising the 3-arylidene-anabaseine compounds (including pharmaceutically acceptable salt, solvate, clathrate, stereoisomer, enantiomers, prodrug or combination thereof) as described herein and one or more pharmaceutically acceptable carriers, excipients, diluents, stabilizers, preservatives, or other inactive ingredients, including combinations of the foregoing, known to skilled artisans and described further herein.

Pharmaceutical compositions and dosage forms of the invention comprise one or more active ingredients in relative amounts and formulated so that a given pharmaceutical composition or dosage form is in a therapeutically effective amount.

Pharmaceutical compositions and dosage forms of the invention include formulations that comprise one or more active ingredients (including at least one 3-arylidene-anabaseine compound as described herein) in relative amounts and formulated so that a given pharmaceutical composition or dosage form inhibits cancer cell proliferation.

Additional pharmaceutical agents (which do not include the 3-arylidene-anabaseine compounds described herein), can include, but are not limited to, anabaseine-related compounds known to those of skill in the art (e.g., as described in U.S. Pat. Nos. 5,977,144 and 5,741,802, incorporated by reference in their entirety) as well as additional non-anabaseine active agents. For example, where a 3-arylidene-anabaseine compound as described herein is a α7 nicotinic receptor full agonist or partial agonist, the pharmaceutical formulation or method of treatment as described herein may include additional pharmaceutical agents known to be efficacious for treatment of the particular condition (e.g., pro-angiogenic compounds for use in wound healing (e.g., nicotine, etc.), including those described in U.S. Pat. Nos. 6,417,205; and 6,720,340, incorporated by reference in their entirety.

Exemplary nicotine receptor agonists include, but are not necessarily limited to, naturally occurring plant alkaloids (e.g., lobeline, lobeline derivatives, and the like), which plant-derived compounds can be provided in a herbal preparation (e.g., in the form of dried tobacco leaves, in a poultice, in a botanical preparation, etc.), in isolated form (e.g., separated or partially separated from the materials that naturally accompany it), or in a substantially purified form. Other nicotine receptor agonists include choline esterase inhibitors (e.g., that increase local concentration of acetylcholine), derivatives of epibatidine that specifically bind the neuronal type of nicotinic receptors (with reduced binding to the muscarinic receptor) and having reduced deleterious side effects (e.g., Epidoxidine, ABT-154, ABT-418, ABT-594, Abbott Laboratories; and Damaj et al. (1998) J. Pharmacol Exp. Ther. 284: 1058-65, describing several analogs of epibatidine of equal potency but with high specificity to the neuronal type of nicotinic receptors). Further nicotine receptor agonists of interest include, but are not necessarily limited to, N-methylcarbamyl and N-methylthi-O-carbamyl esters of choline e.g., trimethylaminoethanol (Abood et al. (1988) Pharmacol. Biochem. Behav. 30:403-8); acetylcholine (an endogenous ligand for the nicotine receptor); and the like.

Additionally, where a 3-arylidene-anabaseine compound as described herein is a α7 nicotinic receptor antagonist, the pharmaceutical formulation or method of treatment as described herein may include additional pharmaceutical agents known to be efficacious for treatment of the particular condition to be treated. For example, anti-angiogenic compounds (e.g., nicotine receptor antagonists) e.g., for the treatment of proliferative retinopathies, for treatment of cancer (e.g., cancer chemotherapeutics, etc.), include, but are not limited to, mecamylamine; hexamethonium (Wotring et al., 1995 Neuroscience 67: 293-300); dihydro-beta-erythroidine (Stolerman et al., 1997 Psychopharmacology 129: 390-397); d-tubocurarine (Wotring et al., 1995); pempidine (Rapier et al., 1990 J. Neurochem. 54: 937-945); chlorisondamine (Caggiula et al., 1995 Psychopharmacology 122: 301-306); erysodine (Decker et al., 1995 Eur. J Pharmacol. 280: 79-80); trimethaphan camsylate (Hisayama et al., 1988 Br. J. Pharmacol. 95:465-472); pentolinium; bungarotoxin; succinylcholine; tetraethylammonium; trimethaphan; chlorisondamine; and trimethidinium.

Preferred pharmaceutical compositions and dosage forms comprise a compound of formula I or a pharmaceutically acceptable prodrug, salt, solvate or clathrate thereof, optionally in combination with one or more additional active agents.

Uses of the 3-Arylidene Compounds

As noted previously, in one aspect are provided methods of treating and/or preventing the conditions described herein using the 3-arylidene-anabaseine compounds and pharmaceutical formulations thereof as described herein. Unless clearly indicated otherwise by the context, the 3-arylidene-anabaseine compounds (and pharmaceutical formulations thereof) described herein may be used without limitation in the methods herein described.

The methods may be practiced as a therapeutic approach towards the treatment and/or prevention of the conditions described herein. Thus, in certain embodiments, the 3-arylidene-anabaseine compounds and pharmaceutical formulations thereof may be used to treat and/or prevent the conditions described herein in individuals in need thereof, including humans.

In some embodiments, the individual is a mammal, including, but not limited to, bovine, equine, feline, rabbit, canine, rodent, or primate. In particular embodiments, the mammal is a primate. In certain embodiments, the primate is a human. In certain embodiments, the individual is human, including adults, children and premature infants.

In certain embodiments, the individual has been identified as having one or more of the conditions described herein. Identification of the conditions as described herein by a skilled physician is routine in the art and may also be suspected by the individual. As for example, in proliferative retinopathies, when an individual notices to loss of vision or visual acuity (e.g., reduction in the field of vision, blurriness, etc.).

In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions (e.g., diabetes for diabetic ulcers, proliferative retinopathies, etc.), lifestyle or habits).

The terms, "pharmaceutically effective amount" or "therapeutically effective amount," and cognates of these terms, as used herein refer to an amount of a formulation sufficient to treat a specified condition (e.g., disease, disorder, etc.) or one or more of its symptoms and/or to prevent the occurrence of the condition. In reference to cancers, a pharmaceutically or therapeutically effective amount comprises an amount sufficient to, among other things, cause a tumor to shrink, or to decrease the growth rate of the tumor.

While many of the 3-arylidene-anabaseine compounds described herein are full agonists or partial agonists of the $\alpha 7$ nicotinic receptor, some 3-arylidene-anabaseine compounds are $\alpha 7$ nicotinic receptor antagonists. Determination of agonist/antagonist activity can be accomplished using techniques known to those of skill in the art, particularly in view of the teaching provided herein. The most direct method of determining whether a compound is a nicotinic agonist or antagonist is to measure the ion flux caused by activation of the nAChR ion channel as a result of exposure to that compound. A number of cell lines expressing a particular mammalian nAChR are available for such use. The ion flux or change in intracellular calcium concentration can be measured with radioisotopically labeled ions or in some cases by calcium ion imaging (nAChRs are permeable to calcium ions as well as sodium and potassium ions). Additionally, the net flux of all ions can be measured electrophysiologically, probably the customary method for assessing the functional properties of nAChR compounds. As described herein, in the present application we transiently transfected messenger RNAs of the particular nAChR in marine frog (*Xenopus laevis*) oocytes, which readily express the subunits for which mRNA are injected over a period of several days. The response of a perfused oocyte to a rapid application of compound was measured with a standard two microelectrode voltage-clamp method where one intracellular electrode measures the internal potential relative to a large external electrode and the other intracellular microelectrode is used to pass a current needed to maintain the cell membrane potential at a predetermined intracellular voltage (usually –60 millivolts). When the nicotinic receptors are stimulated by an agonist, the inward current needed to clamp the membrane potential at –60 mV is recorded as a function of time and either the peak current or the integrated current over several hundred milliseconds is used as a measure of nAChR activation. Current responses were always measured relative to the response to a standard concentration of acetylcholine, usually 100 micromolar for the alpha7 receptor. A series of concentrations was tested on a minimum of three oocytes per concentration to construct a concentration-response curve. The concentration of compound required to produce 50% of the maximal normalized current that could be produced by that compound was measured by curve-fitting with a modified Hill equation. This $EC_{50}$ is a measure of agonist potency. If a compound was not stimulatory, its ability to be an antagonist was measured by coapplying different concentrations with the standard ACh calibrating pulse. The median inhibitory concentration ($IC_{50}$) was thus measured. The lower the $IC_{50}$ concentration, the more potent the compound's inhibitory potency.

As will be understood by the skilled artisan, the 3-arylidene-anabaseine compounds described herein, when identified as agonists (including partial agonists and full agonists) or antagonists of the $\alpha 7$ nicotinic receptor can be used in the treatment and/or prevention of conditions that are mediated by agonism or antagonism of the $\alpha 7$ nicotinic receptor, such as the conditions described herein. For example, antagonists can be used in the treatment of conditions where a reduction in angiogenesis is desirable (e.g., macular degeneration and related conditions (e.g., age-related macular degeneration and other conditions characterized by abnormal neovascularization of the retina and/or choroid, or proliferative retinopathies); cancer or other conditions related to abnormal proliferation, etc. Additional conditions amenable to treatment with $\alpha 7$ nicotinic receptor antagonists are known in the field and described, for example, in WO 03/068208, the disclosure of which is herein incorporated by reference in its entirety.

As used herein, the terms "alpha7 nicotinic acetyl choline receptor agonist," "alpha7 nicotinic agonist," and "alpha7 nicotinergic receptor agonist," and cognates thereof, refer to compounds that bind to the alpha7 nicotinic acetylcholine receptor (nAChR) and stimulate the alpha7 nicotinic receptor (e.g., provide a pharmacological effect, for example, stimulation of angiogenesis). The agonist effect of a compound may be determined using methods routine in the field, for example, by measuring electrophysiologically or radioisotopically the ion flux or change in intracellular calcium concentration as described herein. A "partial agonist" is a compound that stimulates the alpha7 receptor, but whose maximal response is less than that of acetylcholine when measured under the same conditions. A "full agonist" is a compound whose maximal response is the same or greater than that of acetylcholine when measured under the same conditions. Relatedly, chronic administration of alpha7 nicotinic agonists can stimulate or upregulate the concentration of alpha7 nAChRs.

Similarly, 3-arylidene-anabaseine compounds that are $\alpha 7$ nicotinic receptor agonists can be used in conditions where stimulation of $\alpha 7$ nicotinic receptor function is desired. For example, where stimulation of angiogenesis is indicated for therapeutic effect (e.g., wound healing, e.g., of diabetic ulcers, non-healing wounds, etc.) and where nicotinic receptor deficits have been implicated in neurodegenerative conditions and cognitive disorders (such as, e.g., AD and schizophrenia). Additional conditions amenable to treatment with $\alpha 7$ nicotinic receptor full agonists or partial agonists are known in the field and described, for example, in U.S. Pat.

Nos. 6,417,205; 6,720,340, 5,977,144; 5,741,802; and U.S. Pat. App. Pub. No. 2005/004550, the disclosures of which are incorporated by reference in their entirety.

In certain embodiments, the pharmaceutically effective amount is sufficient to prevent the condition, as in being administered to an individual prophylactically.

The 3-arylidene-anabaseine compounds and pharmaceutical formulations thereof and methods described herein may be used alone or in conjunction with (e.g., prior to, concurrently with, or after) other modes of treatment (e.g., adjunctive therapy with additional agents used to treat or prevent the condition being treated and/or administration of an additional treatment modality, or combinations thereof). For example, the compounds may be used in combination with one or more additional pharmaceutical agents (also referred to as therapeutic agents) as described herein and known to those of skill in the art and/or currently available as treatment modalities. As used herein, the term "additional treatment modality" refers to treatment of the conditions described herein without the use of a pharmaceutical agent (e.g., for proliferative retinopathies, one or more of thermal laser photocoagulation, photodynamic therapy, etc.; for cancer, one or more of surgery, radiation therapy, etc). Where combinations of pharmaceutical agent(s) and/or additional treatment modality(ies) are used, they may be, independently, administered prior to, concurrently with, or after administration of the 3-arylidene-anabaseine compounds or pharmaceutical formulations thereof, as described herein.

The 3-arylidene-anabaseine compounds or pharmaceutical formulations thereof described herein can be administered in conjunction with one or more of the pharmaceutical agents as described herein and, as known in the art, one or more additional agents to further reduce the occurrence and/or severity of side effects reactions and/or clinical manifestations thereof, or in conjunction with (e.g., prior to, concurrently with, or after) adjunctive therapies as described herein. The 3-arylidene-anabaseine compounds or pharmaceutical formulations thereof as described herein may be administered before, concurrently with, or after the administration of one or more of the pharmaceutical agents described herein. The formulations thereof described herein may also be administered in conjunction with (e.g., prior to, concurrently with, or after) agents to alleviate the symptoms associated with either the condition or the treatment regimen.

The optimal combination of one or more of surgery and/or additional agents in conjunction with administration of the 3-arylidene-anabaseine compounds or pharmaceutical formulations thereof described herein can be determined by an attending physician based on the individual and taking into consideration the various factors effecting the particular individual, including those described herein.

Conditions to be Treated

The invention is expected to be useful in a number of applications, particularly in treatment of diseases or conditions where it is advantageous to upregulate alpha7 nicotinic receptor activity. Loss of alpha7 receptors occurs in the progression of AD and there is deficient expression of this receptor subtype in schizophrenia. It has been shown that chronic administration of alpha7 agonists like DMXBA can lead to an increased expression of functional alpha7 receptors on cell surfaces. Thus, chronic administration of an alpha7-selective drug may have an even greater effect than before up-regulation in alpha7 number and responsiveness has occurred. In contrast to alpha7 selective ligands, alpha4beta2 receptor ligands generally cause a down-regulation of overall responsiveness of a cell while at the same time there may be an increase in alpha4beta2 receptor number. Thus, chronic administration of alpha4beta2 agonists is more likely to cause tolerance. An up-regulation in responsiveness is expected with the compounds of the invention, either alone or in combination, in appropriate pharmaceutically acceptable forms. Possible applications of these new alpha7 agonists and antagonists based on the anabaseine structure include therapeutic treatments for neurodegenerative diseases and addictions involving nicotinic receptors, as well as potential development as antiproliferation drugs. In particular, it is shown that altering anabaseine compound polarity and ionization can permit drug application and localization to the peripheral (blood and interstitial fluid) compartments without significant entry into the central nervous system.

The nAChR population in the AD brain at death is greatly reduced relative to a normal aging brain. Neurodegeneration is most obvious in the neocortex and the hippocampus regions associated with higher mental functions. The two most abundant nAChR subtypes can be separately measured using the radiolabeled snake toxin alpha-bungarotoxin for the $\alpha 7$ subtype and radiolabeled (S)-nicotine or cytisine for the $\alpha 4\beta 2$ nAChR subtype. Recent studies in AD brains showed that in the neocortex the major loss of binding sites with nicotine agonists is associated with a marked reduction in the $\alpha 4\beta 2$ nAChRs and a much smaller reduction in $\alpha 7$ nAChRs. Using either in situ hybridization or monoclonal antibodies, there is a decrease in both the alpha4 (40%) and the alpha7 (17%) subunit protein expression in AD cortices compared to age-matched controls. Since there is less significant reduction in the $\alpha 7$ nAChR subtype in Alzheimer's disease patients, it is an attractive target for therapeutic drugs that can stimulate the function of the remaining receptors.

Harmful peptides such as $\beta$-amyloid$_{1-42}$ formed through the abnormal cleavage of amyloid precursor protein (APP) may be responsible for AD. APP is a transmembrane protein located on the surface of cells in many tissues and organs. The exact function of this protein is not known; however, it has been implicated in nerve cell growth and movement and as a gene switch. $\beta$-amyloid$_{1-40}$ is present in the brain and cerebrospinal fluid of normal subjects in picomolar concentrations. In AD patients, there is evidence of an elevated level of $\beta$-amyloid$_{1-42}$, which exhibits toxic effects on neurons. The $\beta$-amyloid$_{1-42}$ peptide may lose its helical shape and form fibrils with other proteins, making them less soluble. As these fibrils bind with other fibrils, amyloid plaques are ultimately formed; neuronal degeneration associated with AD seems to be related to some as yet unidentified, insolubilized form of $\beta$-amyloid.

Evidence for a more direct involvement of the $\alpha 7$ nAChR in Alzheimer's disease is the ability of $\beta$-amyloid$_{1-42}$ to bind to the $\alpha 7$ receptor, as suggested by the co-immunoprecipitation of $\beta$-Amyloid$_{1-42}$ with the $\alpha 7$ receptor in samples from postmortem AD hippocampus. Additionally, $\alpha 7$ antagonists and $\beta$-amyloid competitively bind to heterologously expressed $\alpha 7$ receptors. If the $\alpha 7$ receptor is a receptor for $\beta$-amyloid$_{1-42}$ neurotoxicity, selective $\alpha 7$ nAChR full agonists, partial agonists, or antagonists which prevent $\beta$-amyloid from binding to this receptor may also inhibit the development of AD.

In addition to CNS applications, this invention is expected to provide therapeutic agents that selectively stimulate peripheral alpha7 receptors expressed on non-neuronal cells such as macrophages, vascular endothelium and bronchial epithelium, which are peripheral cells known to express functional alpha7 nAChRs. When macrophage alpha7 receptors are stimulated, the secretion of inflammatory cytokines such as TNF is inhibited. These cytokines are known to exacerbate an immune response when overproduced and not efficiently removed from the system. Stimulation of vascular endothelial cells, for example, is known to enhance angiogenesis.

Alpha7 nAChRs have also been found on non-neuronal cells within the nervous system (for example, astrocytes and microglia) and outside the nervous system; e.g., on macrophages, bronchial epithelium and vascular endothelium. Alpha7 receptors on peripheral macrophages, when stimulated by appropriate agonists, inhibit the secretion of cytokines, including tumor necrosis factor alpha (TNF-α), which cause inflammation. Similarly, stimulation of alpha7 nAChRs in vascular endothelium enhances the formation of new blood vessels (angiogenesis), an important process in wound healing. On the other hand, proliferation of certain small cell lung cancers expressing primarily alpha7 nAChRs can be stimulated by nicotinic agonists and possibly inhibited with certain nicotinic antagonists. Thus, besides being implicated as useful therapeutic targets for treating nervous system disorders such as AD and schizophrenia, alpha7 nAChRs on non-neuronal cells may also be therapeutic targets for treating other disease states involving inflammation, trauma, deficient or excessive angiogenesis, and abnormal proliferation (cancer).

An important aspect of the invention is the expectation of providing a variety of substituted 3-arylidene-anabaseines displaying a range of agonistic efficacies at alpha7 nicotinic receptors. Factors to be taken into consideration include disposition of the therapeutic target, whether CNS or peripheral within systemic circulation, or contained within an organ with unique access such as the lung; possible side effects of the alpha7 drug at sites other than the intended target as well as through the intended target; and the need for a highly selective agonist, in addition to the age, sex, and general health of the patient. For example, it may be advantageous to use an arylidene-3-arylidene-anabaseine compound that does not cross the blood brain barrier when systemic and other peripheral inflammations are being treated and the alpha7 receptors on macrophages are being targeted. In treating pulmonary inflammation, it may be preferable to utilize an anabaseine that does not readily pass into the systemic circulation after being administered through an inhaler directly into the pulmonary space.

It is expected that the disclosed compounds may also exhibit pharmacokinetic as well as pharmacodynamic properties that are distinctly superior to previously synthesized and tested compounds and which would not have been predicted. Addition of a chemical group to improve compound potency, efficacy and selectivity may also make the compound less readily metabolized by protecting otherwise reactive sites on the molecule. For example, benzylidene-anabaseines containing methoxy substituents on the arylidene ring are readily O-dealkylated by hepatic cytochrome P450 enzymes to hydroxy- and ultimately glucuronido-hydroxy metabolites. Replacement of these alkoxy groups with other substitutents may improve potency, selectivity, bioavailability, and/or plasma half-life (a measure of how long the administered drug stays available for therapeutic effect). Thus, position of the substituents providing alpha7 selectivity may also improve the pharmacokinetic properties of the arylidene-anabaseine.

Thus, in some embodiments, are provided 3-arylidene-anabaseines that are useful in the treatment of conditions mediated by alpha7 nicotinic receptors. Conditions which may be treated with the 3-arylidene-anabaseines described herein (and pharmaceutical formulations thereof), include conditions in which the desired therapy includes the stimulation of the alpha7 nicotinic receptors (i.e., use of the 3-arylidene compounds described herein which are alpha7 nicotinic receptor agonists) or the inhibition of the alpha7 nicotinic receptors (i.e., use of the 3-arylidene compounds described herein which are alpha7 nicotinic receptor antagonists).

The activity and/or selectivity of the 3-arylidene-anabaseine compounds described herein, including whether a particular compound is an agonist (including partial agonist or full agonist) or antagonist of the alpha7 nicotinic receptor can be determined using methods known to the skilled artisan, particularly in view of the teachings provided herein. Methods for the characterization of the 3-arylidene-anabaseine compounds can also be found, for example, in U.S. Pat. Nos. 5,581,785; 5,741,802; 5,977,144; and 6,630,491, the disclosures of which are incorporated by reference in their entirety.

In certain embodiments, the 3-arylidene-anabaseines, which are alpha7 nicotinic receptor agonists, may be used in the treatment of conditions that are treatable by the stimulation of the alpha7 nicotinic receptor, including, for example, neurological conditions (e.g., AD, Parkinson's Disease; vascular dementia; age-related cognitive decline (AACD); mild cognitive impairment (MCI); AIDS-related dementia; schizophrenia; bipolar disorder; stimulant addiction (e.g., to cocaine, amphetamines, etc.); psychoses (e.g., manic psychoses, etc.); enhancing cognitive behavior (e.g., enhancing learning, memory retention, etc.); glutamate-induced toxicity toward cortical cells; inflammation (e.g., the stimulation of alpha7 receptors in peripheral macrophages, etc.); conditions treatable by the stimulation of angiogenesis (e.g., wound healing (e.g., diabetic ulcers, wounds in non-diabetics, etc.)) and other conditions known to be treatable by the stimulation of alpha7 nicotinic receptors (e.g., conditions as described in U.S. Pat. Nos. 5,581,785; 5,741,802; 5,977,144; and 6,630,491)).

In addition, agonism of the alpha7 nicotinic receptor has also been linked to treatment of the additional conditions, including, but not limited to, inflammatory bowel disease (including, but not limited to, ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotropic lateral sclerosis (ALS), cognitive dysfunction, tinnitus, hypertension, bulimia, anorexia, obesity, cardiac arrythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, stroke, traumatic brain injury (TBI), Huntington's Chorea, tardive dyskinesia, hyperkinesia, dyslexia, multi-infarct dementia, age related cognitive decline, epilepsy, including petit mal absence epilepsy, senile dementia, attention deficit hyperactivity disorder (ADHD) and Tourette's Syndrome.

In certain embodiments, the condition to be treated is a neurodegenerative condition. For example, AD, Parkinson's Disease, vascular dementia, AACD, MCI, AIDS-related dementia, schizophrenia, bipolar disorder, stimulant addiction (e.g., to cocaine, amphetamines, etc.) psychoses (e.g., manic psychoses, etc.). In some embodiments, the condition to be treated is AD, Parkinson's Disease, or vascular dementia. In other embodiments, the condition is schizophrenia.

Inflammation is one of several mechanisms employed by the body to fight infections and in normal circumstances is deployed only for sufficient time to alleviate or eliminate the source of disease or foreign invader. Part of the immune response is activation of macrophages. These cells release cytokines such as tumor necrosis factor (TNF) that induce expression of molecules that enhance inflammation.

Unfortunately, the immune response is not always confined to the location where it is needed. This may lead to sepsis (e.g., when TNF and the bacteria it is recruited to fight enter the systemic blood circulation) or, the immune system may begin to attack the body it is intended to protect. Chronic inflammatory disorders such as Crohn's Disease, certain forms of arthritis and even heart disease are now thought to be precipitated by inflammation. Additionally, there are many diseases now thought to result from an autoimmune response, including systemic lupus erythematosus, autoimmune hemolytic anemia, membranous glomerulonephritis, autoimmune polyendocrinopathies, autoimmune thyroiditis, idiopathic thrombocytopenic purpura, Addison's disease, insulin-dependent diabetes mellitus, etc. Acute inflammation of specific organs may also be treated with the same alpha7 nAChR agonists.

Thus, in some embodiments, the 3-arylidene-anabaseines, which are alpha7 nicotinic receptor agonists, may be used in the treatment of conditions that include inflammation as a symptom or precursor. For example, in some embodiments the condition to be treated is an autoimmune condition. In particular embodiments, the condition is systemic lupus erythematosus, autoimmune hemolytic anemia, membranous glomerulonephritis, autoimmune polyendocrinopathies, autoimmune thyroiditis, idiopathic thrombocytopenic purpura, Addison's disease or insulin-dependent diabetes mellitus.

The compounds of the present invention that are being developed as selective alpha7 nAChR drugs for treatment of inflammation and autoimmune diseases are agonists. The relation between alpha7 receptors on macrophages and cytokine secretion (TNF, IL-4, IL-6) has been determined from studies in which the vagus nerve was stimulated (to produce TNF) in alpha7-deficient mice, resulting in an exaggerated inflammatory response to an immunostimulatory lipopolysaccharide because alpha 7 receptors on macrophages normally are stimulated by the vagally-released acetylcholine and this inhibits TNF secretion from the macrophages. The presence of alpha7 receptors on macrophages is therefore considered to make them an excellent target for controlling inflammation by employing these new compounds in cases where there is an excessive proliferation of macrophages in the peripheral system. Some compounds of the invention are targeted for use in treatment of peripheral system inflammation such as sepsis. The compounds selected would not cross the blood brain barrier and therefore would remain outside the central nervous system. Arylidene-anabaseines expected to have these properties include the protected and de-protected glucuronide metabolites of DMXBA and, as a particular example, the compound shown:

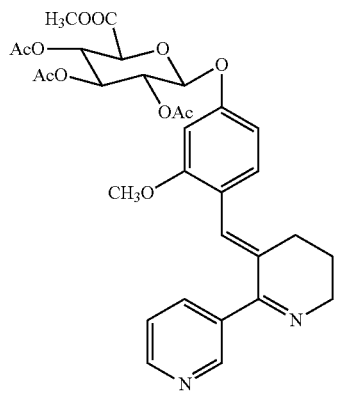

In particular embodiments of the 3-benzylidene-glucuronidyl-anabaseines, an additional acetylated glucuronidyl (as shown above) is included at a position other than 4" on the benzylidene ring. Thus, where the 3-arylidene-anabaseine is a 3-benzylidene-glucuronidyl-anabaseine, $R^1$ can additionally be an acetylated glucuronidyl group.

It is believed that alpha7 nicotinic receptor agonists may be useful in stimulating angiogenesis in wound healing and other conditions in which there is inadequate tissue perfusion. New tissue requires a robust blood supply in order to function efficiently and tissue lacking sufficient oxygenation may become necrotic. Development of new blood vessels is of prime importance in recovery of damaged heart tissue. The brain is the site of several types of insults, including stroke and vascular dementia and there is a decrease in number of microvessels in the aging brain (Uspenskaia, et al., 2004). In selected cases therefore, it may be beneficial to target cerebral microvessels in the basal lamina with the agents of the present invention in order to stimulate neoangiogenesis and increase blood flow and distribution in the brain.

Thus, in some embodiments, the 3-arylidene-anabaseines, which are alpha7 nicotinic receptor agonists, may be used in the treatment of conditions that are treatable by the stimulation of angiogenesis. For example, in some embodiments, the condition to be treated is a wound. In particular embodiments, the wound is a diabetic ulcer. In other embodiments the wound is a non-healing wound in a non-diabetic individual. Additional conditions that may be treated include those described in U.S. Pat. Nos. 6,417,205 and 6,720,340, the disclosures of which are incorporated by reference herein in their entirety. For example, the 3-arylidene-anabaseines, which are alpha7 nicotinic receptor agonists, may be used as a therapeutic approach to enhance angiogenesis in the treatment of coronary, peripheral, or other occlusive arterial diseases; and for the enhancement of wound healing and the improved vascularization of surgically transplanted tissues or organs (e.g., skin grafts or reattached limbs).

In particular embodiments the 3-arylidene-anabaseines, which are alpha7 nicotinic receptor antagonists, may be used in the treatment of conditions that are treatable by the inhibition of the alpha7 nicotinic receptor, including, for example, conditions that are treatable by the inhibition of angiogenesis (e.g., proliferative retinopathies, e.g., macular degeneration (including age-related, etc.; retinopathy of prematurity, etc.; and conditions associated with hyperproliferation, e.g., cancer, etc., including those conditions described in, for example WO03/068208, which is hereby incorporated by reference in its entirety).

For example, conditions and disorders amenable to treatment with 3-arylidene-anabaseines, which are alpha7 nicotinic receptor antagonists, include, but are not limited to, cancer; atherosclerosis; proliferative retinopathies such as diabetic retinopathy; age-related maculopathy; retrolental fibroplasia; excessive fibrovascular proliferation as seen with chronic arthritis; psoriasis; and vascular malformations such as hemangiomas, and the like.

The instant methods are useful in the treatment of both primary and metastatic solid tumors, including carcinomas, sarcomas, leukemias, and lymphomas. Of particular interest is the treatment of tumors occurring at a site of angiogenesis. Thus, the methods are useful in the treatment of any neoplasm, including, but not limited to, carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). The instant methods are also useful for treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, the instant methods are useful for reducing metastases from the tumors described above either when used alone or in combination with radiotherapy and/or other chemotherapeutic agents.

Other conditions and disorders amenable to treatment using the methods of the instant invention include autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemangiomas, and capillary proliferation within atherosclerotic plaques; Osler-Webber Syndrome; plaque neovascularization; telangiectasia; hemophiliac joints; angiofibroma; and excessive wound granulation (keloids).

Inhibition of angiogenesis would be desirable in certain medical conditions, such as in tumor cell proliferation and in some forms of retinal (macular) degeneration. Alpha7 nAChR antagonists could be useful in inhibiting angiogenesis, as new blood vessel growth is necessary for growth of solid tumors. An anabaseine alpha7 nAChR antagonist that is polar, and/or ionized and/or conjugated to another inactive molecule such as a complex carbohydrate or a polyethylene glycol that confers on the molecule pharmacokinetic advantages and limits its diffusion to the compartment of administration may be useful as an angiogenesis inhibitor in treating certain conditions. Such an arylidene-anabaseine type alpha7 nAChR antagonist could also be directly administered into the arterial blood perfusing the tumor to achieve even greater selectivity of action.

Thus, in some embodiments, the 3-arylidene-anabaseines, which are alpha7 nicotinic receptor antagonists, may be used in the treatment of proliferative neuropathies.

In certain embodiments, the 3-arylidene-anabaseines, which are alpha7 nicotinic receptor antagonists, may be used in the treatment of proliferative diseases.

As used herein, the terms "alpha7 nicotinic acetyl choline receptor antagonist," "alpha7 nicotinic antagonist," and "alpha7 nicotinergic receptor antagonist," and cognates thereof, refer to compounds that bind to the alpha7 nicotinic acetylcholine receptor (nAChR) and inhibit the alpha7 nicotinic receptor (e.g., provide a pharmacological effect, for example, reduction of angiogenesis). The antagonist effect of a compound may be determined using methods routine in the field, for example, by measuring electrophysiologically or radioisotopically the ion flux or change in intracellular calcium concentration as described herein. If a compound is not an agonist (as measured described herein), identification of antagonism of the alpha7 receptor can be measured by determining the compound's $IC_{50}$ determined by co-application of concentrations of acetylcholine, as described in detail herein. Relatedly, alpha7 nicotinic antagonists can "inhibit" alpha7 nAChR function upon binding.

As used herein, the term "selectively binds," "selective binding," and cognates thereof refer to anabaseine compounds that preferentially bind to the alpha7 nAChR versus the alpha4beta2 nAChR. Binding to the alpha7 and alpha4beta2 nAChR (including relative binding to each of these receptors) can be determined by the skilled artisan using the methods known in the art, in particular in view of the teachings provided herein. In particular, the assays used to determine selective binding are according to Marks and Collins for [$^{125}$I]alpha-bungarotoxin experiments (for alpha7 receptor binding) and a modified method by Pabreza for [$^{3}$H]cytisine experiments (for alpha4beta2), used as described in the "methods" section of the Examples, and in Example 1 of the present specification.

In particular embodiments, the 3-arylidene-anabaseine is an antagonist of the alpha7 nicotinic receptor. In certain of these embodiments, the antagonist is 6'-methyl-DMXBA, 6'-methyl-3-cinnamylidene-anabaseines, 6'-methyl-3-arylidene-anabaseines, 3-(4-thiomethoxybenzylidene)-anabaseine, 3-(4-difluromethoxybenzylidene)-anabaseine, or 3-(4-dimethylaminopropoxybenzylidene)-anabaseine. In some embodiments, the antagonist is 3-(4-thiomethoxybenzylidene)-anabaseine.

Formulation and Dosage

The 3-arylidene-anabaseine compounds or pharmaceutical formulations thereof described herein will generally be used in an amount effective to achieve the intended result, for example in an amount effective to treat or prevent the particular condition being treated. The 3-arylidene-anabaseine compounds or pharmaceutical formulations thereof may be administered therapeutically to achieve therapeutic benefit. By "therapeutic benefit" is meant eradication or amelioration of the underlying condition being treated and/or eradication or amelioration of one or more of the symptoms associated with the underlying condition such that the patient reports an improvement in feeling or condition, notwithstanding that the patient may still be afflicted with the underlying condition. Therapeutic benefit also includes halting or slowing the progression of the condition, regardless of whether improvement is realized.

The amount of the formulations administered in order to administer an effective amount of 3-arylidene-anabaseine compounds or pharmaceutical formulations thereof will depend upon a variety of factors, including, for example, the particular condition being treated, the frequency of administration, the particular 3-arylidene-anabaseine compounds or pharmaceutical formulations thereof being administered, the severity of the condition being treated and the age, weight and general health of the individual, the adverse effects experienced by the individual being treated, etc. Determination of an effective dosage is within the capabilities of those skilled in the art in view of the teachings provided herein.

Compositions containing 3-arylidene-anabaseine compound(s) (and any additional pharmaceutical agent as described herein, e.g., a chemotherapeutic agent, anti-angiogenesis agent, pro-angiogenesis agent, etc.) may be administered in several ways, including orally, parenterally, intraperitoneally, intradermally or intramuscularly. Pharmaceutical forms suitable for injection include sterile aqueous solutions or dispersions for extemporaneous preparation of the solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained by the use of a coating such as lecithin, by the maintenance of the required particle size in case of a dispersion and by the use of surfactants. The prevention of the action of microorganisms can be effected by various antibacterial and antifungal agents such as parabens, chlorobutanol, phenol, sorbic acid, thimerosal and the like. In many cases, isotonic agents may be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral dosage forms are also contemplated. Pharmaceutical compositions of the invention which are suitable for oral administration can be presented as discrete dosage forms, including, but not limited to, tablets (e.g., chewable tablets), caplets, capsules and liquids such as flavored syrups. Dosage forms containing predetermined amounts of active ingredients may be prepared by well known methods of pharmacy. See, e.g., *Remington's Pharmaceutical Sciences* (1990) 18$^{th}$ ed., Mack Publishing Co., Easton, Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral, liquid, or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivates (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferable from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other cellulosses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The pH of a pharmaceutical composition or dosage form, or of the tissue where the composition or dosage form is applied, may be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients to improve delivery. Stearates for example can serve as a lipid vehicle for the formulation, as an emulsifying agent or surfactant, and as a delivery-enhancing or penetration-enhancing agent. Salts, hydrates or solvates of the active ingredients can be used to further adjust the properties of the resulting compositions.

Upon formulation, solutions are administered in a manner compatible with the dosage formulation and in such amount as is therapeutically effective. The formulations are easily administered in a variety of dosage forms preferably as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intradermal and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see, for example, *Remington's Pharmaceutical Sciences*, 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLES

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or composition are to be considered to fall within the scope of the invention disclosed herein.

Materials

[$^{125}$I]α-bungarotoxin and [$^3$H]cytisine were obtained from Perkin Elmer Life and Analytical Sciences (Billerica, Mass.). BCA protein reagent A and B as well as Albumin Standard was purchased from Pierce (Rockford, Ill.). 1-octanol and acetonitrile HPLC grade were purchased from Fisher Scientific (Fair Lawn, N.J.). Monobasic and dibasic sodium phosphate were obtained from Fisher Scientific (Fair Lawn, N.J.). Cell culture media was purchased from American Tissue Culture Collection (ATCC) (Manassas, Va.). Hygromycin B was obtained from Calbiochem (La Jolla, Calif.). Penicillin/Streptomycin and fetal bovine serum were purchased from Cellgro by Mediatech (Herndon, Va.). Trypsin (1:250) solution was purchased from Irvine Scientific (Santa Ana, Calif.). The Flexstation calcium assay kit and membrane potential kit, were obtained from Molecular Devices (Sunnyvale, Calif.). All other chemicals were ACS grade and were obtained from either Sigma Chemical Co. (St. Louis, Mo.) or from Fisher Scientific (Fair Lawn, N.J.).

Methods

Radioligand Binding Studies

Assays were performed using the experimental compound to compete for its nAChR binding site with a radioligand that specifically labels either the α4β2 or the α7 nAChR in homogenized Sprague-Dawley rat brain membrane. These assays were used to determine the $IC_{50}$ of the experimental compounds, which is then used to determine the $K_I$ with the Cheng-Prusoff equation.

Radioligand binding assays were performed according to Marks and Collins for the [$^{125}$I]α-bungarotoxin experiments and a modified method by Pabreza for the [$^3$H]cytisine experiments. To assess the binding affinity of the compounds for the α7 nAChR, a concentration of 1 nM [$^{125}$I]α-bungarotoxin was incubated with 0.2 mg of rat brain homogenate, a concentration (ranging from 5 nM-50 µM) of 3-arylidene-anabaseine compound or 1 mM nicotine in order to determine non-specific binding. The final volume was brought up to 0.5 ml with a 2 mg/ml concentration of bovine serum albumin (BSA) suspended in 50 mM tris binding saline at a pH of 7.4 (120 mM NaCl, 5 mM KCl, 2 mM $CaCl_2$, 1 mM $MgCl_2$, 50 mM tris buffer) in order to reduce non-specific binding. To assess total binding, only the radioligand and the tissue with 2 mg/ml BSA in tris binding saline were incubated together.

The 3-arylidene-anabaseine compound was suspended in 50 mM Tris binding saline, with 2 mg/ml BSA, if it was a salt, or in methanol if it was a free base, and dilutions were made in 2 mg/ml BSA Tris binding saline. The final solutions were incubated at 37° C. for approximately 2.5 hours. Once the reaction was assumed to be at equilibrium, it was stopped by harvesting the tissue onto GF/C filters, which were soaked for 45 minutes in a 0.5% polyethylenamine solution to reduce non-specific binding of the radioligand to the filter, using a Brandel tissue harvester. The filters were then placed in gamma tubes and counted on a Beckman counter for 5 minutes per sample. The counts per minute were then assessed, the results were entered, and the $IC_{50}$s and $K_I$s were determined using the software program Graphpad Prism®. The [$^3$H]cytisine experiments were performed in a similar manner. First the addition of all of the components: 1 nM [$^3$H]cytisine, 3-benzylidene-3-arylidene-anabaseine compound (5 nM-50 µM), 0.2 mg rat brain homogenate, and 2 mg/ml BSA Tris solution at a pH of 7.4 to bring the final volume up to 0.5 ml in each tube.

To assess non-specific binding, 1 mM nicotine was added in place of the 3-arylidene-anabaseine. To assess total binding, only the radioligand, tissue, and BSA Tris solution were added. The incubation time and the temperature were altered in this protocol to produce the greatest difference between total and non-specific binding and to maximize the affinity of the radioligand for the receptor, respectively. The incubation time for [$^3$H]cytisine was 4 hours at 4° C. The reaction was stopped using a Brandel tissue harvester and the filters were placed in scintillation vials with a 30% Scintasafe scintillation cocktail overnight. The samples were then placed into a Beckman scintillation counter for 5 minute counts per sample. The counts per minute were entered into GraphPad Prism® where the $IC_{50}$s and the $K_I$s were assessed.

Rat brain membrane was obtained frozen from Pel-Freez Biologicals (Rogers, Ariz.). The protein concentration of the rat brain homogenate was assessed using the bicinchoninic acid (BCA) protein assay kit from Pierce (Rockford, Ill.).

Octanol/Water Partition Coefficients

P is the ratio of the concentration of an un-ionized form of a compound in octanol relative to the unionized concentration of the compound in an aqueous phase containing 150 mM NaCl (to approximate physiological conditions), after the two phases have equilibrated. Log P values were determined for each test compound by RP-HPLC analysis. Approximately 1 mg of each compound was weighed out and placed in equal volumes, 3 ml 10 mM sodium phosphate buffer, pH 7.4, which contained 150 mM NaCl, and 1-octanol. Previously, equal volumes of the sodium phosphate buffer and 1-octanol were added to a separatory funnel and allowed to equilibrate overnight. The equilibrated sodium phosphate buffer was checked prior to its addition to the compound for a pH of 7.4. Once these phases were added to the weighed compound, the solutions were allowed to equilibrate overnight on a gentle shaker at room temperature. The samples were centrifuged at 1×g for 5 minutes and octanol phase carefully removed with a Pasteur pipette. The pH of the water phase was remeasured in order to calculate the corrected Log P value.

Since large concentrations of octanol cannot be directly injected into the HPLC without affecting the elution of the compound being measured, the compound was extracted from the separated octanol phase with an acidic 150 mM NaCl solution adjusted to a pH of approximately 2.6 (with 100 mM glacial acetic acid). The acidic saline solution was allowed to gently mix with the octanol phase for 20 minutes on a shaker at room temperature. The samples containing the octanol and acidic saline phases were then centrifuged at 1,000×g for 5 minutes and the upper octanol phase was carefully removed with a Pasteur pipette. This back extraction step was repeated at least two and sometimes three times. All three or four back extracted solutions for a particular compound were then combined. Both the original aqueous and the back extracted octanol phases were then diluted with 50 mM ammonium acetate buffer, pH 4.5. The diluted samples were then transferred by pipette to autosampler tubes and subsequently 350-500 ml of each diluted sample was injected into the HPLC. The area under the curve (AUC) of an absorbance peak was determined for samples from both (octanol and aqueous) of the original phases. Taking into account the dilutions of each sample phase during its preparation for HPLC determination, Log P (taking into consideration the percent ionization at pH 7.4) was then calculated.

Spectrophotometric pKa Determination

The pKa of the most basic (imine) nitrogen of each test compound was determined by analysis of the pH dependence of the imine electronic absorbance spectrum at room temperature using a 50 mM potassium phosphate buffer in the presence of 150 mM NaCl. Thirteen different pH values in the titration region were evaluated (pH: 4, 5, 6, 7, 7.2, 7.5, 7.8, 8, 8.2, 8.5, 8.8, 9, 10). A specific concentration of 3-benzylidene-3-arylidene-anabaseine compound, $1.3 \times 10^{-3}$ M, was added to the potassium phosphate buffers at varied pH values. Each tube was then vortexed and immediately read in a Beckman spectrophotometer. The same glass cuvette was used with every sample. The glass cuvette was thoroughly rinsed with distilled deionized water between different pH samples. The wavelength scan was set to a range of 250-600 nm. The pH with the highest change in absorbance was determined. The wavelength at the highest change in absorbance and the absorbance values for all of the different pH samples at this wavelength were entered into the Enzfitter software (Elsevier-Biosoft, Cambridge, UK) in order to estimate each pKa value.

Chiral Chromatography

Separation by chiral chromatography is an attractive alternative to fractional crystallization of optically-active salts because it can provide the desired enantiomer more quickly and in greater purity. While chiral chromatographic methods for the separation of nicotine enantiomers have been published, no one previously reported the separation of the enantiomers of any anabaseine compound. We succeeded in the complete separation of the 4-methyl-DMXBA and 5-methyl-DMXBA using a Chiral Technologies (West Chester, Pa.) OJ-H (10 mm inner diameter X 250 mm length) column eluted with a linear solvent gradient of increasing polarity by computer programmed mixture of increasing proportions of Buffer B with starting buffer A (Buffer A composition was 94.9% hexane, 5% isopropanol and 0.1% diethylamine; Buffer B composition was 84.9% hexane, 15% isopropanol and 0.1% diethylamine). After injection of the racemic compound, the column was developed over a period of 30 minutes with the gradient mentioned (0% B to 60% B). The racemic 6-methyl-DMXBA was similarly separated, but the B Buffer now contained 74.9% hexane, 25% isopropanol and 0.1% diethylamine; the A Buffer was the same as mentioned above. Eluting compounds were measured by absorbance measurements using a photodiode array detector. The relative amounts were estimated by electronic integration of the absorbance peaks. The two enantiomers displayed identical absorbance spectra and absorbance peak areas, as expected. The eluting compounds were collected with an Isco Foxy fraction collector equipped with PeakTrak software, and were concentrated on a SpeedVac evaporation system in dim light before being subjected to radioligand binding analysis.

Cell Culture

The human epithelial cell line SH-EP1 expressing the recombinant human α7 nAChR was obtained from R. J. Lukas (St. Joseph's Hospital and Medical Center, Phoenix, Ariz.). This cell line is native nAChR-null. Cells were maintained in Dulbecco's Modified Eagle's Medium supplemented with 5% (w/v) fetal bovine serum, 10% heat-inactivated horse serum, penicillin/streptomycin at 100 µg/ml, 2 µg/ml Amphotericin B, 0.4 mg/ml hygromycin B, and 2.2 mg/ml sodium bicarbonate in a humidified atmosphere containing 5% $CO_2$ at 37° C.

The rat pituitary GH4C1 cell line expresses the rat α7 nAChR (M. Quik, Parkinson's Institute in Sunnyvale, Calif.). This cell line is a clonal line that does not endogenously express nicotinic receptors. Cells were maintained in F-10 nutrient mixture supplemented with 10% (w/v) fetal bovine serum (FBS), penicillin/streptomycin at 100 µg/ml, and 0.4 mg/ml hygromycin B, in a humidified atmosphere containing 5% $CO_2$ at 37° C. The human rhabdomyosarcoma TE-671 cell line expressing the fetal muscle nAChR (J. W. Daly, (National Institutes of Health, Bethesda, Md.). This cell line endogenously expresses the fetal muscle nicotinic receptor. Cells were maintained in Dulbecco's Modified Eagles Medium supplemented with 10% (w/v) fetal bovine serum (FBS), and penicillin/streptomycin 100 µg/ml, in a humidified atmosphere containing 5% $CO_2$ at 37° C. Cells were harvested weekly using 0.25% trypsin and seeded at a dilution of 1:3-1:8. Media was changed every 2-3 days. For experiments, cells were plated onto poly-d-lysine-coated (50 µg/ml) 96-well, black-walled, transparent bottomed plates. All experiments were initiated at confluency, which was usually after an overnight incubation. Other alpha7-expressing cells were also cultured essentially in the same manner as in the two examples above.

Example 1

Measurement of Alpha7 Receptor Binding Selectivities

After decapitation, washed whole rat brain membranes (200 µg of protein) were prepared according to the method used by Marks and Collins (1982). Displacement of $^{125}$I-labelled alpha-bungarotoxin (BTX) measured binding to alpha7 receptors; displacement of [$^3$H]-labelled cytisine measured binding to alpha4beta2 receptors. Before use, the washed membranes were resuspended in 500 µl receptor binding assay saline (pH 7.4) consisting of 120 mM NaCl, 5 mM KCl, 2 mM CaCl$_2$, 1 mM MgCl$_2$ and 50 mM Tris-HCl. [$^3$H]cytisine (35 Ci/mmole)-binding displacement experiments were performed essentially according to Flores et al. (1992), except that the incubation time was increased to 4 hr at 0 to 4° C. to ensure equilibrium during the competition binding assay. Binding of 125I-BTX (136 Ci/mmole) was performed at 37C.° for 3 h; the saline solution mentioned above also contained 2 mg/ml bovine serum albumin. Nonspecific binding of each radioligand was measured in the presence of 1.0 mM nicotine. After incubation, membranes with bound radioligand were collected on Whatman GF/C glass filber filters presoaked for 45 min in 0.5% polyethylenimine and washed three times with 3.0 ml of ice-cold buffer by vacuum filtration on a harvester (Brandel, Gaithersburg, Md.). Bound [3H] cytosine was measured in a liquid scintillation counter, whereas [125]BTX was measured with use of a Biogamma counter (both from Beckman Coulter). Binding studies were analyzed using Prism software (GraphPad Software Inc., San Diego, Calif.). All Ki values were calculated from the Cheng-Prusoff equation, using a Kd value for each radioligand that had been experimentally determined under conditions identical with those of the displacement experiments. The alpha7 binding selectivity of each compound shown in Table 1 was estimated by dividing the Ki for aplha4beta2 binding by the Ki for alpha7 binding. The alpha7 binding selectivity of each compound relative to DMXBA (Table 1) was calculated by dividing the Ki for alpha4beta2 binding by the Ki for alpha7 binding and then dividing this product by the measured alpha7 selectivity of DMXBA (1.95 reported in Table 3 of Kern et al., 2004 Mol. Pharmacol. 65, page 62).

TABLE 1

RAT BRAIN ALPHA7 RECEPTOR RADIOLIGAND BINDING DATA FOR SELECTED 3-(DMXB)-METHYL-ANABASEINES AND 3-(4-GLUCURONIDINYL-2-METHOXYBENZYLIDENE)-ANABASEINE RETENTION TIMES FOR CHIRAL COLUMN SEPARATED ENANTIOMERS ARE ALSO INCLUDED

| COMPOUND | CHIRAL COLUMN RETENTION TIME | RELATIVE A7/A4B2 SELECTIVITY |
| --- | --- | --- |
| Anabaseine | | 0.69 |
| DMXBA (GTS-21) | | 1.00* |

TABLE 1-continued

RAT BRAIN ALPHA7 RECEPTOR RADIOLIGAND BINDING DATA FOR SELECTED 3-(DMXB)-METHYL-ANABASEINES AND 3-(4-GLUCURONIDINYL-2-METHOXYBENZYLIDENE)-ANABASEINE RETENTION TIMES FOR CHIRAL COLUMN SEPARATED ENANTIOMERS ARE ALSO INCLUDED

| COMPOUND | CHIRAL COLUMN RETENTION TIME | RELATIVE A7/A4B2 SELECTIVITY |
| --- | --- | --- |
| (S,R)-4-Methyl-Anabaseine | | 0.69 |
| (S,R)-4-Methyl-DMXBA | | 4.10 |
| Most selective enantiomer of 4-Methyl-DMXBA | (21 min. ChCol Ret T) | 8.34 |
| Least selective enantiomer of 4-Methyl-DMXBA | (26 min. ChCol Ret T) | 1.28 |
| (S,R)-5-Methyl-Anabaseine | | 0.38 |
| (S,R)-5-Methyl-DMXBA | | 1.31 |
| Most selective enantiomer of 5-Methyl-DMXBA | (25 min. ChCol Ret T) | 2.34 |
| Least selective enantiomer of 5-Methyl-DMXBA | (27 min. ChCol Ret T) | 1.03 |
| (S,R)-6-Methyl-Anabaseine | | 1.19 |
| (S,R)-6-Methyl-DMXBA | | 3.67 |
| Most selective enantiomer of 6-Methyl-DMXBA | (21 min. ChCol Ret T) | 5.34 |
| Least selective enantiomer of 6-Methyl-DMXBA | (29 min. ChCol Ret T) | 2.93 |
| 4'-Methyl-Anabaseine | | — |
| 4'-Methyl-DMXBA | | 14.8 |
| 3-(4-Beta-Glucuronidyl-2-methoxyB)A | | 9.40 |

*Receptor selectivity of DMXBA is arbitrarily expressed as 1.0 to facilitate comparison of other compounds with DMXBA. The actual rat alpha7 selectivity of DMXBA is 1.95.

Example 2

Fused Ring Substituted Benzylidene-Anabaseines

Table 2 shows physical and binding properties of some 3-substituted benzylidene-anabaseines. Binding was determined using the procedure described in Example 1.

TABLE 2

RECEPTOR-BINDING AND PHYSICAL PROPERTIES OF SOME FUSED RING 3-SUBSTITUTED ANABASEINES

| Compound Name | Structure | Ki (μM) α7 | Ki (μM) α4β2 | Ki α4β2/α7 Ratio* | PKa | % ionized | Log P |
| --- | --- | --- | --- | --- | --- | --- | --- |
| 3-[3,4-(Ethylenedioxy)benzylidene]-anabaseine | 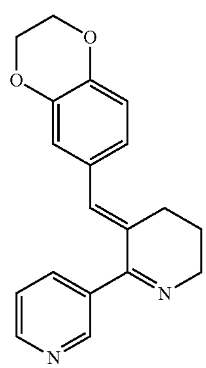 [SMILES: C(=C1/CCCN=C1c1cccnc1)/c1ccc2c(c1)OCCO2] | 0.20 ± 0.01 n = 2 | 0.52 ± 0.01 n = 2 | 2.60 | 7.56 ± 0.03 | 59.11 | 3.103 |

TABLE 2-continued

RECEPTOR-BINDING AND PHYSICAL PROPERTIES OF SOME FUSED RING 3-SUBSTITUTED ANABASEINES

| Compound Name | Structure | Ki (µM) α7 | Ki (µM) α4β2 | Ki α4β2/α7 Ratio* | PKa | % ionized | Log P |
|---|---|---|---|---|---|---|---|
| 3-[3,4-(Methylene-dioxy)benzylidene]-anabaseine | 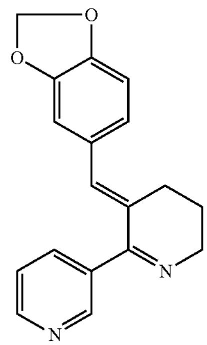 [SMILES: C(=C1/CCCN=C1c1cccnc1)/c1ccc2c(c1)OCO2] | 0.23 ± 0.002 n = 2 | 0.70 ± 0.07 n = 2 | 3.04 | 7.64 ± 0.04 | 63.48 | 2.428 |
| 3-[(6-Methoxy-naphth-2-yl)methylene]-anabaseine | 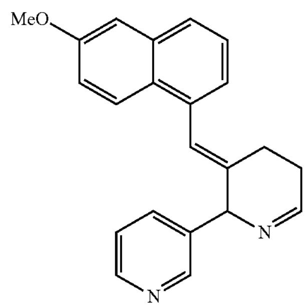 [SMILES: COc1ccc2c(/C=C3\CCC=NC3c3cccnc3)cccc2c1] | 0.37 ± 0.03 n = 2 | 0.60 ± 0.10 n = 2 | 1.62 | 7.29 ± 0.12 | 43.67 | 2.653 |
| 3-[(Benzofuran-2-yl)methylene]-anabaseine | 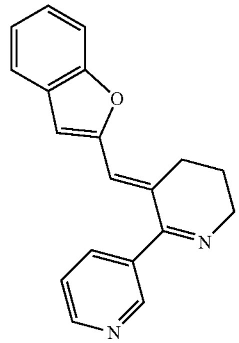 [SMILES: C(=C1/CCCN=C1c1cccnc1)/c1cc2ccccc2o1] | 0.15 ± 0.003 n = 2 | 5.92 ± 1.06 n = 2 | 39.5 | 9/2/04 | 33.90 | 3.86 ± 0.40 |

*The alpha7 receptor selectivities in this table are not normalized with respect to DMXBA selectivity, as are the selectivities of the compounds in Table 1 (see footnote to Table 1 for actual DMXBA selectivity).

Example 3

Synthesis of 3-(2,4-Diacetoxybenzylidene)-Anabaseine

To a solution of sodium hydroxide (0.060 g, 1.50 mmole) in water (0.75 ml) at room temperature and strong stirring, isopropanol (4 ml) was added. When the mixture became clear, 2,4-dihydroxybenzylidene-anabaseine dihydrochloride (0.071 g, 0.20 mmole) was added and next acetic anhydride (0.104 ml, 0.112 g, 1.10 mmole) was added dropwise. After strong stirring at room temperature for 30 minutes the isopropanol was removed in a vacuum (at 45° C.), to the residue ethyl acetate (5 ml) was added and the mixture was washed with saturated sodium chloride solution (2×0.5 ml). The organic solution was dried over magnesium sulfate and evaporated in a vacuum (at 45° C.), giving the crude product (0.064 g, 88%). The product was purified by column chromatography on silica gel (7 g) with acetone-methanol (8-2) giving the pure product (0.043 g, 59%). 1H-NMR (CDCl3) delta 8.72 (dd, J=2.4, 0.9, 1H), 8.63 (dd, J=4.8, 1.8, 1H), 7.78 (dt, J=7.8, 2.1, 1H), 7.38 (d, J=8.7, 1H), 7.33 (ddd, J=7.8, 4.8, 0.9, 1H), 7.04 (dd, J=8.4, 2.4, 1H), 6.94 (d, J=2.4, 1H), 3.95-3.87 (m, 2H), 2.74-2.65 (m, 2H), 2.29 (s, 3H), 2.16 (s 3H), 1.87-1.77 (m, 2H).

Example 4

Synthesis of 3-(4-Methylthiobenzylidene)-anabaseine dihydrochloride

To a suspension of anabaseine dihydrochloride hydrate (0.101 g, 0.40 mmole) and 4-methylthiobenzaldehyde (0.069 g, 0.45 mmole) in dry ethanol (1.5 ml), concentrated hydrochloric acid (1 drop) was added and stirred in an oil bath of 70-75° C. in argon atmosphere for 24 hours. The reaction mixture was cooled in an ice bath for 3 hours, filtered and washed three times with ice-cold ethanol under argon atmosphere and dried in vacuum at room temperature over phosphorus pentoxide overnight, giving the pure product (0.14 g, 95%) as a yellow powder, mp. 219-221° C. (decomp.). 1H-NMR (DMSO-d6) delta 9.01-8.92 (m, 2H), 8.29 (dt, J=7.8, 1.8, 1H), 7.84 (dd, J=7.8, 5.1, 1H), 7.57 (d, J=8.7, 2H), 7.37 (d, J=8.7, 2H), 7.21 (s, 1H), 3.86-3.76 (m, 2H), 3.04-2.95 (m, 2H), 2.53 (s, 3H), 2.11-1.98 (m, 2H).

Example 5

Synthesis of 3-(4-Acetamidobenzylidene)-anabaseine dihydrochloride

A suspension of anabaseine dihydrochloride hydrate (0.101 g, 0.40 mmole) and 4-N-acetylbenzaldehyde (0.073 g, 0.45 mmole) in dry ethanol was stirred at 70-75° C. for 24 hours, then left to crystallize in a refrigerator overnight. The separated crystalline material was filtered and washed with ice-cold dry ethanol (three times) under argon atmosphere and dried at room temperature in a desiccator over phosphorus pentoxide, giving the pure product (0.132 g, 87%). 1H-NMR (DMSO-d6) delta 10.58 (s, 1H), 8.97 (dd, J=5.1, 1.5, 1H), 8.94 (d, J=1.8, 1H), 8.26 (dt, J=7.8, 1.8, 1H), 7.82 (dd, J=8.1, 5.1, 1H), 7.77 (d, J=8.7, 2H), 7.61 (d, J=8.7, 1H), 7.16 (s, 1H), 3.87-3.75 (m, 2H), 3.07-2.96 (m, 2H), 2.15-1.98 (m, 2H).

Example 6

Synthesis of 3-(4-Aminocarbonylbenzylidene)-anabaseine

To a solution of 4-carboxybenzaldehyde (1.50 g, 0.010 mole) in dry tetrahydrofuran (20 ml), 4-methylmorpholine (2.20 ml, 2.02 g, 0.020 mole) was added, cooled to −5° C., and with rapid stirring, ethyl chloroformate (0.96 ml, 1.09 g, 0.010 mole) was added in 5 minutes (the inside temperature remained under 0° C.). After 30 minutes of stirring at 0° C. it was cooled to −5° C. and 0.5 M ammonia solution in 1,4-dioxane (22 ml, 0.011 mole) was added in 7 minutes (the inside temperature remained under 0° C.). After 30 minutes of stirring at 0° C., the ice-bath was removed and left to warm up to room temperature. Dichloromethane (50 ml) and water (20 ml) was added and the white crystals were filtered, washed with water (3×5 ml) and with dichloromethane (2×3 ml), and dried under an infrared lamp, giving the pure product (0.47 g, 33%), mp: 165-170° C.

To a solution of 4-aminocarbonylbenzaldehyde (0.37 g, 2.5 mmole) and anabaseine dihydrochloride hydrate (0.75 g, 3.0 mmole) in dry ethanol (30 ml), concentrated hydrochloric acid (3 drops) was added and stirred in an oil bath of 85° C. for 14 days. After cooling, it was evaporated in a vacuum, the residue was dissolved in water (10 ml), sodium hydrogen carbonate (0.5 g) was added, and the mixture was extracted with chloroform (3×5 ml). The combined extracts were dried (magnesium sulfate), decolorized (activated carbon), and evaporated in a vacuum. The residue (0.82 g) was treated with dichloromethane-methanol mixture (9-1), filtered, the crystals were washed three times with dichloromethane, and dried under an infrared lamp, giving the product (0.11 g, 15%), as white crystals. It can be further purified by recrystallization from n-propanol, mp: 224-226° C. 1H-NMR (DMSO-d6) delta 8.66 (d, J=2.1, 1H), 8.62 (dd, J=4.8, 1.5, 1H), 7.99 (br s, 1H), 7.91-7.84 (m, 3H), 7.49-7.41 (m, 3H), 6.61 (s, 1H), 3.82-3.74 (m, 2H), 2.85-2.75 (m, 2H), 1.79-1.67 (m, 2H).

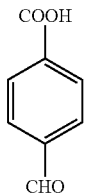 1. ClCOOEt, NMM/THF 2. NHdrioxan 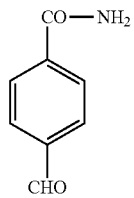

Example 7

Synthesis of 3-(4-Ethylcarbamoyloxybenzylidene)-anabaseine

To a suspension of 3-(4-hydroxybenzylidene)-anabaseine (0.053 g, 0.2 mmole) in dry acetonitrile (2 ml), ethyl isocyanate (0.079 ml, 0.071 g, 1.0 mmole) was added and stirred at 50-55° C. for one day while the reaction mixture was protected from moisture. Further ethyl isocyanate (0.079 ml, 0.071 g, 1.0 mmole) was added to the reaction mixture and the stirring was continued at 50-55° C. for an additional 4 days. The clear solution was evaporated in a vacuum (at 45° C.). The residue was dissolved in dry dichloromethane (2 ml), evaporated in a vacuum, dissolved again in dry benzene (2 ml), the insoluble material was filtered and the solution was evaporated in a vacuum (45° C.), giving the pure product (0.056 g, 83%). 1H-NMR (CDCl3) delta 8.74 (d, J=1.5, 1H), 8.64 (dd, J=4.8, 1.5, 1H), 7.82 (dt, J=7.5, 1.8, 1H), 7.33 (ddd, J=7.5, 4.8, 0.9, 1H), 7.28 (d, J=8.7, 2H), 7.31 (d, J=8.7, 1H), 6.62 (s, 1H), 5.02 (br s, 1H), 3.93-3.82 (m, 2H), 3.40-3.25 (m, 2H), 2.86-2.77 (m, 2H), 1.89-1.77 (m, 2H), 1.22 (t, J=7.2, 3H).

Example 8

Synthesis of 3-[(6-Methoxy-naphth-2-yl)-methylene]-anabaseine dihydrochloride To a mixture of magnesium turnings (0.48 g, 20 mmole) and dry ether (10 ml) under argon atmosphere, iodomethane (1.30 ml, 2.96 g, 21 mmole) was added drop-by-drop in 15 minutes with slow stirring. When the ether started to boil, the mixture was cooled slightly in a cold water bath. The mixture was stirred for 30 minutes to get a solution of methyl magnesium iodide. At ice cooling, dry tetrahydrofuran (5 ml) and then a solution of 6-methoxy-tetralone-1 (Comp. A, Aldrich, 1.76 g, 10 mmole) in dry tetrahydrofuran (5 ml) was added drop-by-drop in 15 minutes. The reaction mixture was stirred at ice cooling for 1 hour and at room temperature for an additional 1 hour. To the white suspension at ice cooling and stirring, an ice cold solution of ammonium chloride (1.64 g, 30 mmole) in water (10 ml) was added drop-by-drop in 2 minutes and stirred for 15 minutes. It was separated and the aqueous phase extracted with ether (3×5 ml), the combined organic phases were combined, dried (magnesium sulfate) and evaporated in a vacuum. The residue (1.72 g) was purified by chromatography on a silica gel (50 g) with hexane-ether (9-1, v/v, Rf 0.56) giving the pure product 6-Methoxy-1-methyl-3,4-dihydronaphthalene (Compound B, 1.41 g, 81%) as a pale yellow oil.

To a solution of Compound B (0.44 g, 2.5 mmole) in dry dimethylformamide (1.3 ml, 16.8 mmole) at ice cooling and stirring under argon atmosphere, phosphorus oxychloride (0.62 ml, 6.65 mmole) was added drop-by-drop in 2 minutes. The reaction mixture was stirred in an oil bath of 70-75° C. for 3 hours. After cooling in an ice bath, ice (6 g) was added, then sodium acetate (anhydrous, 3.7 g) was added, and the mixture (pH ~6) was warmed in an oil bath at 70-75° C. for 15 minutes. After cooling, it was extracted with ether (1×10 ml and 3×5 ml), the combined organic solutions were washed with water (3×3 ml), dried (magnesium sulfate), decolorized (with activated carbon), and evaporated. The residue (0.33 g) was recrystallized from cyclohexane (2 ml) and dried over potassium hydroxide in a vacuum giving the pure product 6-Methoxy-1-methyl-3,4-dihydro-2-naphthaldehyde (Compound C, 0.22 g, 44%) as light brown crystals, mp. 70-72° C.

To a suspension of anabaseine dihydrochloride hydrate (0.101 g, 0.40 mmole) and Compound C (0.084 g, 0.45 mmole) in dry ethanol (1.5 ml), concentrated hydrochloric acid (1 drop) was added and stirred in an oil bath of 70-75° C. in argon atmosphere for 24 hours. The reaction mixture was cooled in an ice bath for 3 hours, filtered and washed three times with ice cold ethanol under argon atmosphere, and dried in a vacuum at room temperature

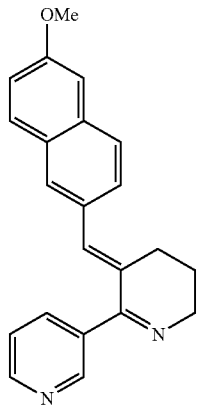 [SMILES: COc1ccc2cc(/C=C3\CCCN=C3c3cccnc3)ccc2c1]

3-[(6-Methoxy-naphth-2-yl)-methylene]-anabaseine dihydrochloride (Compound D) over phosphorus pentoxide overnight, giving the pure product 3-(6-Methoxy-naphth-2-yl-methylene)-anabaseine dihydrochloride (Compound D, 0.11 g, 69%) as orange colored powder, mp. 223-226 CC (decomp.). 1H-NMR (DMSO-d6) delta 9.05-8.97 (m, 2H), 8.35 (dt, J=8.1, 1.8, 1H), 8.18 (s, 1H), 7.95-7.82 (m, 3H), 7.70 (dd, J=8.7, 1.2, 1H), 7.41 (d, J=2.7, 1H), 7.37 (s, 1H), 7.25 (dd, J=9.0, 2.4, 1H), 3.91 (s, 3H), 3.89-3.80 (m, 2H), 3.19-3.07 (m, 2H), 2.16-2.02 (m, 2H).

Example 9

Synthesis of 3-[(6-Methoxy-1-methyl-3,4-dihydronaphth-2-yl)-methylene]-anabaseine (D)

6-Methoxy-1-methyl-3,4-dihydronaphthalene (Compound B)

To a mixture of magnesium turnings (0.48 g, 20 mmole) and dry ether (10 ml) under argon atmosphere, iodomethane (1.30 ml, 2.96 g, 21 mmole) was added drop-by-drop in 15 minutes at slow stirring. When the ether started to boil, the mixture was cooled a little down by a cold water bath. The mixture was stirred for 30 minutes to get a solution of methyl magnesium iodide. At ice cooling, dry tetrahydrofuran (5 ml) and then a solution of 6-methoxy-tetralone-1 (Comp. A, Aldrich, 1.76 g, 10 mmole) in dry tetrahydrofuran (5 ml) was added drop-by-drop in 15 minutes. The reaction mixture was stirred at ice cooling for 1 hour and at room temperature for an additional 1 hour. To the white suspension at ice cooling and stirring, an ice cold solution of ammonium chloride (1.64 g, 30 mmole) in water (10 ml) was added drop-by-drop in 2 minutes and stirred for 15 minutes. It was separated and the aqueous phase extracted with ether (3×5 ml), the combined organic phases were combined, dried (magnesium sulfate) and evaporated in a vacuum. The residue (1.72 g) was purified by chromatography on silica gel (50 g) with hexane-ether (9-1, v/v, Rf 0.56), giving the pure product (1.41 g, 81%) as a pale yellow oil.

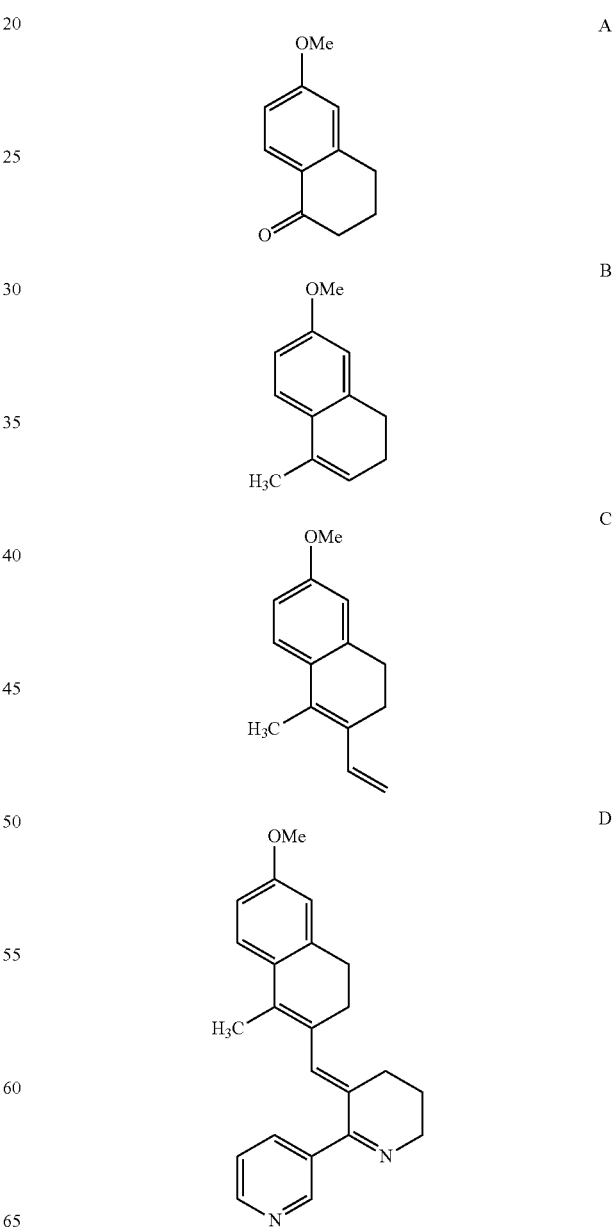

6-Methoxy-1-methyl-3,4-dihydro-2-naphthaldehyde (Compound C)

To a solution of 6-methoxy-1-methyl-3,4-dihydronaphthalene (0.44 g, 2.5 mmole) in dry dimethylformamide (1.3 ml, 16.8 mmole) at ice cooling and stirring under argon atmosphere, phosphorus oxychloride (0.62 ml, 6.65 mmole) was added drop-by-drop in 2 minutes. The reaction mixture was stirred in an oil bath of 70-75° C. for 3 hours. After cooling in ice bath, ice (6 g) was added, then sodium acetate (anhydrous, 3.7 g) was added, and the mixture (pH ~6) was warmed in an oil bath at 70-75° C. for 15 minutes. After cooling, it was extracted with ether (1×10 ml and 3×5 ml), the combined organic solutions were washed with water (3×3 ml), dried (magnesium sulfate), decolorized (with activated carbon), and evaporated. The residue (0.33 g) was recrystallized from cyclohexane (2 ml) and dried over potassium hydroxide in a vacuum, giving the pure product (0.22 g, 44%) as light brown crystals, mp. 70-72° C.

To a suspension of anabaseine dihydrochloride hydrate (0.101 g, 0.40 mmole) and 6-methoxy-1-methyl-3,4-dihydro-2-naphthaldehyde (C, 0.091 g, 0.45 mmole) in dry ethanol (1.5 ml) concentrated hydrochloric acid (1 drop) was added and stirred in an oil bath of 70-75° C. in argon atmosphere for 24 hours. The reaction mixture was cooled in ice bath for 3 hours, the unchanged anabaseine dihydrochloride (0.06 g, 0.26 mmole) was filtered and washed three times with ice cold ethanol under argon atmosphere. The combined ethanolic solutions were evaporated in a vacuum, the residue (0.10 g) was dissolved in water (1 ml), potassium hydrogen carbonate (0.1 g) was added, and extracted with dichloromethane (3×1 ml). The combined organic solutions were dried (magnesium sulfate), decolorized (activated carbon), and evaporated in a vacuum. The residue (0.06 g) was chromatographed on silica gel (5 g) with ether-triethylamine (8-2, v/v, Rf 0.21), giving the pure product (Compound D, 0.017 g, yield 12.3%, conversion 20.5%) as light brown thick oil. 1H-NMR (CDCl3) delta 8.73 (d, J=2.4, 1H), 8.62 (d, J=4.8, 1.8, 1H), 7.81 (dt, J=7.8, 1.8, 1H), 7.34 (dd, J=7.8, 4.8, 1H), 7.23 (d, J=8.4, 1H), 6.75 (dd, J=8.4, 2.7, 1H), 6.70 (d, J=2.4, 1H), 6.45 (s, 1H), 3.92-3.85 (m, 2H), 3.81 (s, 3H), 2.77-2.67 (m, 2H), 2.54-2.45 (m, 2H), 2.38-2.28 (m, 2H), 1.94 (s, 3H), 1.86-1.75 (m, 2H).

Example 10

Synthesis of 3-(4-Hydroxybenzylidene)-4'-methylanabaseine dihydrochloride

To a suspension of 4'-methylanabaseine dihydrochloride (0.099 g, 0.40 mmole) and 4-hydroxybenzaldehyde (0.055 g, 0.45 mmole) in dry ethanol (1.5 ml), concentrated hydrochloric acid (1 drop) was added and stirred in an oil bath of 70-75° C. in argon atmosphere for 20 hours. The reaction mixture was cooled in an ice bath for 3 hours, filtered and washed three times with ice cold ethanol under argon atmosphere and dried in a vacuum at room temperature over phosphorus pentoxide overnight, giving the pure product (0.111 g, 79%) as a pale yellow powder, mp. 260 262° C., (decomp.). 1H-NMR (DMSO-d6) delta 8.84 (d, J=5.4, 1H), 8.81 (s, 1H), 7.77 (d, J=5.4, 1H), 7.55 (d, J=9.0, 2H), 7.04 (s, 1H), 6.91 (d, J=8.7, 2H), 3.94-3.72 (m, 2H), 3.11-2.90 (m, 2H), 2.39 (s, 3H), 2.15-1.98 (m, 2H).

Example 11

Synthesis of 3-[(Indol-3-yl)methylene]-anabaseine dihydrochloride

To a suspension of anabaseine dihydrochloride hydrate (0.093 g, 0.40 mmole) and indole-3-carboxaldehyde (0.064 g, 0.44 mmole) in dry ethanol (3 ml), concentrated hydrochloric acid (2 drops) was added and stirred at 75-80° C. for one day, then left to crystallize in a refrigerator for 3 days. The separated crystalline material was filtered and washed with ice-cold dry ethanol (three times) under argon atmosphere and dried at room temperature in a desiccator over phosphorus pentoxide, giving the pure product (0.102 g, 71%). 1H-NMR (DMSO-d6) delta 8.99 (dd, J=5.1, 1.8, 1H), 8.95 (d, J=1.8, 1H), 8.33 (d, J=3.3, 1H), 8.27 (dt, J=8.1, 1.8, 1H), 7.84 (dd, J=8.1, 5.1, 1H), 7.57-7.51 (m, 2H), 7.43 (d, J=7.8, 1H), 7.30-7.23 (m, 1H), 7.19-7.12 (m, 1H), 3.80-3.71 (m, 2H), 2.98-2.89 (m, 2H), 2.18-2.06 (m, 2H).

Example 12

Synthesis of 3-(4-Glucuronido-2-methoxybenzylidene)-anabaseine

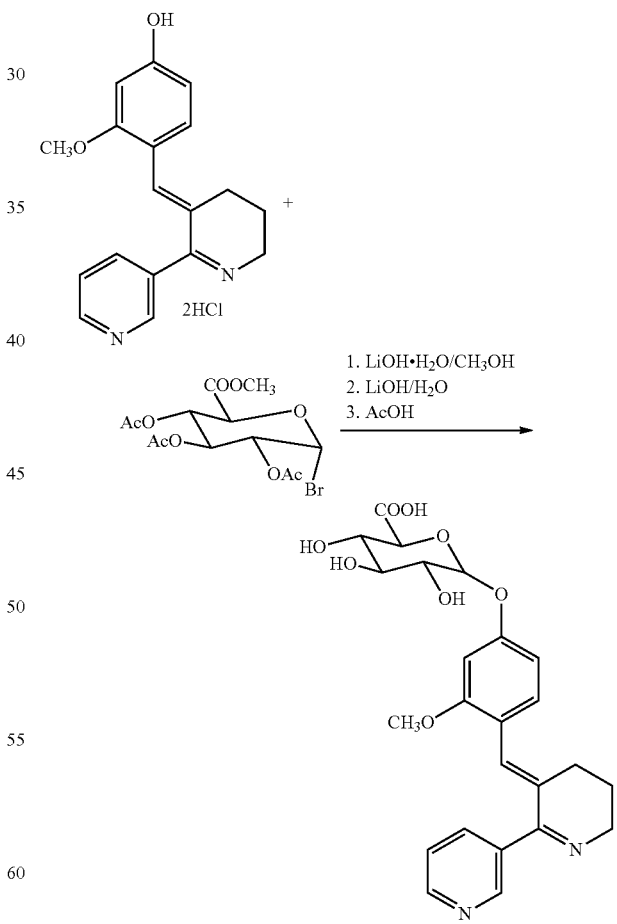

To a suspension of 3-(4-hydroxy-4-methoxybenzylidene)-anabaseine (0.100 g, 0.27 mmole) in dry methanol (2 ml) at room temperature with stirring, lithium hydroxide hydrate (0.034 g, 0.81 mmole) was added. Next, to the formed solution, acetobromoalpha-D-glucuronic acid methyl ester (0.107 g, 0.27 mmole) was added and stirred for 30 minutes. To the reaction mixture, water (2 ml) and lithium hydroxide hydrate (0.034 g, 0.81 mmole) were added and stirred for a further 30 minutes. The reaction mixture was evaporated in a vacuum at room temperature to about 1 ml, and acetic acid (2 drops) was added. The precipitation was removed, washed with a small amount of methanol and the combined solutions were evaporated to about 0.5 ml and cooled at −2° C. for 2 days. The precipitation was filtered, washed with a small amount of methanol and the combined solutions were evaporated in a vacuum at room temperature. The residue (0.060 g) was purified by HPLC (CAN/H$_2$O/0.1% TFA), giving the product (9.9 mg, 7.8%) as a light yellow amorphous solid. HR-FAB 471.1777 M++1), calculated for C$_{24}$H$_{27}$N$_2$O$_8$: 471.1767). Its 1H NMR was in good agreement with the literature data (Azuma et al., 1999) for 3-(4-glucuronido-2-methoxy)benzylidene-anabaseine isolated as a urinary metabolite after administration of 3-(2,4-dimethoxy)benzylidene-anabaseine.

Example 13

Synthesis of 4-Methyl-anabaseine (New Synthesis)

β-Methyl-δ-valerolactone (Compound B, Synthesis Scheme in Example 14)

To a suspension of sodium borohydride (8.00 g, 0.20 mole) in anhydrous tetrahydrofuran (240 ml) at ice cooling and stirring under argon atmosphere, β-methylglutaric anhydride (Comp. A, Aldrich, 25.60 g, 0.20 mole) was added in 3 minutes and stirred at ice cooling for 10 minutes and at room temperature for 19 hours. To the suspension at ice cooling and with stirring, 1:1 hydrochloric acid (80 ml) was added very cautiously over 20 minutes, and stirred at ice cooling for 15 minutes and at room temperature for 5 hours. The mixture was concentrated in rotavapor at 55° C. at 50 Hgmm. The suspension was filtered and first the filtered salt and then the solution was extracted with chloroform (5×25 ml), dried (magnesiun sulfate), and evaporated. The residue (22.51 g) was purified by vacuum distillation, collecting the main fraction at 84-91° C. at 4.6 Hgmm, giving the pure product (17.35 g, 76%) as a colorless thick oil.

Ethyl 5-bromo-3-methylglutarate (Compound C, Synthesis Scheme in Example 14) A solution of β-methyl-δ-valerolactone (17.12 g, 0.15 mole) in dry ethanol (35 ml) was saturated with dry hydrogen bromide gas at ice cooling and stirring, and then was stored at room temperature in a closed round bottom flask for 3 days. The mixture was poured onto a mixture of water (150 ml) and ice (150 g). After the ice melted, the mixture was extracted with dichloromethane (3×25 ml), the combined extracts were washed with sodium hydrogen carbonate solution (1×25 ml of 5% solution in water), dried (magnesium sulfate), and evaporated at 55° C. in a good vacuum, giving the pure product (31.33 g, 94%) as a colorless thick oil. If necessary, the product can be distilled, collecting the main fraction at 103-108° C. in 13 Hg mm.

Ethyl 5-azido-3-methylvalerate (Compound D, Synthesis Scheme in Example 14) To a solution of ethyl 5-bromo-3methylvalerate (31.24 g, 0.14 mole) in dry dimethylsulfoxyde (140 ml), sodium azide (13.65 g, 0.21) was slowly added with strong stirring. The suspension was stirred in an oil bath of 47-50° C. overnight. At warming, the sodium azide went slowly into solution and the product started to separate. After cooling to room temperature, the suspension was poured into water (350 ml) and extracted with ether (3×100 ml). The combined extracts were washed with saturated sodium chloride solution (2×100 ml), dried (magnesium sulfate), and evaporated (50° C. at 2 Hg mm) giving the pure product (25.04 g, 97%) as a light yellow oil.

β-Methyl-δ-valerolactam (Compound E, Synthethis Scheme in Example 14) To a solution of ethyl 5-azido-3-methylvalerate (4.44 g, 24 mmole) in dry tetrahydrofuran (25 ml), triphenyphosphine (6.29 g, 24 mmole) was added at stirring. The reaction mixture warmed up (to about 40° C.) and nitrogen gas evolved. After the gas evolution ceased, water (0.43 ml, 24 mmole) was added and the reaction mixture was stirred overnight (18 hours). The clear solution was evaporated (in good vacuum at 40° C.), the solid residue was suspended in a mixture of ether (50 ml) and hexane (50 ml) and stirred for 2 hours. The triphenylphosphine oxide was filtered, washed with ice cold ether (5×10 ml), and the combined solutions were evaporated (in good vacuum at 45° C.). The solid residue (3.91 g) was chromatographed on silica gel (100 g) with ethyl acetate-methanol mixture (9-1, v/v, R$_f$0.22, visualization with P—Mo-acid), giving the pure product (2.52 g, 93%) as not hygroscopic white solid, mp: 89-91° C.

N-BOC-β-Methyl-δ-valerolactam (Compound F, Synthesis Scheme in Example 14) To a solution of β-methyl-δ-valerolactam (0.56 g, 5 mmole) in dry dichloromethane (10 ml) under argon atmosphere, triethylamine (0.70 ml, 0.51 g, 5 mmole), di-tert-butyl dicarbonate (2.18 g, 10 mmole), and 4-dimethylaminopyridine (0.61 g, 5 mmole) were added and stirred at room temperature for 23 hours. The reaction mixture was evaporated in good vacuum at 55° C., and the residue (1.75 g) was purified by column chromatography on silica gel (60 g) with ethyl acetate (Rf 0.61, visualization with P—Mo-acid), giving the pure product (0.94 g, 88%) as a thick oil.

4-Methyl-anabaseine (Compound G, Synthesis Scheme in Example 14) A stirred solution of 3-bromopyridine (0.67 ml, 1.11 g, 7.0 mmole) in dry ether (17 ml) was cooled to −90° C. (with hexane-liquid nitrogen) and under argon atmosphere, butyllithium solution (2.5 M in hexane, 2.8 ml, 7.0 mmole) was added drop-by-drop in 7 minutes and the mixture further stirred for 20 minutes. At −90° C. N-BOC-β-methyl-δ-valerolactam (1.49 g, 7.0 mmole) in dry THF (10 ml) was added very slowly (in 45 minutes) and further stirred for 3 hours. To the cold solution, 1N hydrochloric acid (7.0 ml, 7.0 mmole) was slowly added and the mixture was left to warm to room temperature. After separation, the aqueous phase was extracted with ether (5×10 ml), the combined organic phases were dried (magnesium sulfate) and evaporated in a vacuum. The residue (1.95 g) was dissolved at ice cooling in trifluoroacetic acid (8.75 ml), then further stirred at room temperature for 3.5 hours. After evaporation (in water vacuum at 40° C.), sodium hydroxide solution (6 g sodium hydroxide in 14 ml water) was added to reach pH 10-11 and extracted with ether (40×10 ml). The combined organic solutions were dried (magnesium sulfate) and evaporated, giving pure product (0.86 g, 70%) as a colorless thick oil.

Example 14

Synthesis of 3-(4-Hydroxybenzylidene)-4-methyl-anabaseine dihydrochloride

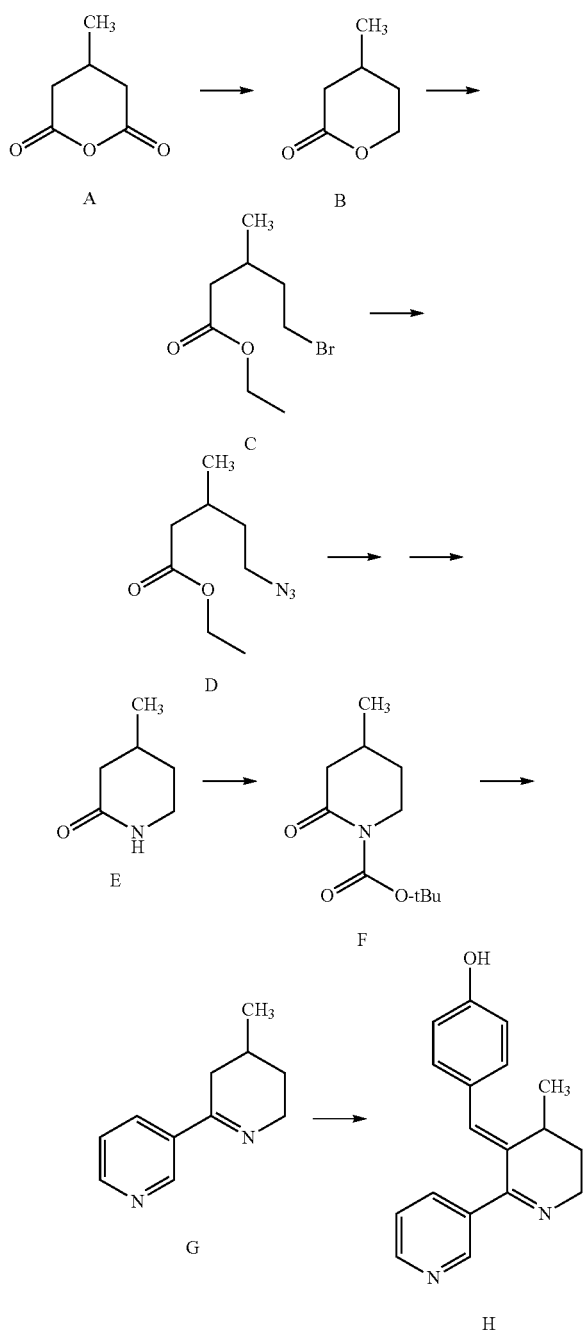

To a solution of 4-methyl-anabaseine (Compound G, 0.35 g, 2.0 mmole) in dry ethanol (15 ml), concentrated hydrochloric acid (0.4 ml, ~4.8 mmole) and p-hydroxy benzaldehyde (0.27 g, 2.2 mmole) were added and under argon atmosphere in an oil bath of 70-75° C. was stirred for 19 hours. After standing, the resulting suspension at +8~for 3 days the yellow crystals were filtered and washed three times with ice-cold ethanol under argon atmosphere and dried in a vacuum over phosphorus pentoxide at room temperature for 4 hours giving the pure product 3-(4-Hydroxybenzylidene)-4-methyl-anabaseine dihydrochloride (Compound H) (0.33 g, 47%) as yellow powder, mp. 240-244~(decomp.). 1H-NMR (DMSO-d6) delta 8.98 (dd, J=5.1, 1.5, 1H), 8.95 (d, J=1.8, 1H), 8.27 (dt, J=7.8, 1.8, 1H), 7.84 (dd, J=7.8, 5.1, 1H), 7.55 (d, J=8.7, 2H), 7.06 (s, 1H), 6.94 (d, J=8.7, 2H), 3.96-3.76 (m, 2H), 3.63-3.50 (m, 1H), 2.15-2.04 (in, 1H), 2.04-1.89 (m, 1H), 1.38 (d, 3=7.2, 3H).

REFERENCES

The following references, to the extent that they provide exemplary procedural or other details supplementary to those set forth herein, are specifically incorporated by reference. The disclosures of all references cited throughout the specification are hereby specifically incorporated by reference in their entirety.

Kem, W. R., "The brain alpha7 nicotinic receptor may be an important therapeutic target for the treatment of Alzheimer's dieses: studies with DMXBA (GTS-21), Behav Brain Res 113(1-2); 169-181 (2002).

Li, Y; He, Y. J., King, M. A., Meyer, E. M., and Millard, W. J., "The selective alpha7 nicotinic agonist DMXB counteracts the ethanol-induced release of mitochondrial cytochrome c", 26(1/2): Abstract No. 526.14, November 4-9 (Gainesville, Fla.), Soc. For Neuroscience Abstracts (2000).

U.S. Pat. No. 5,217,975

U.S. Pat. No. 5,510,478

U.S. Pat. No. 4,798,829

WO 2004/019943 (Mar. 11, 2004) "3-arylidene-anabaseine compounds useful in the treatment of neurodegenerative diseases"

Pat. App. Pub. No. US 2004/0087616 (May 6, 2004)

Simosky, J. K., Stevens, K. E. and Freedman, R. Curr Drug Target CNS Neurol Disord April 149-162 (2002).

Papke, R. L., Research Grant G M57481 Abstract, 2003.

Azuma, R., Komuro, M., Korsch, B. H., Andre, J. C., Onnagawa, O., Black, S. R. and Matthews, J. M. "Metabolism and disposition of GTS-21, a novel drug for Alzheimer's disease" Xenobiotica, v. 29(7), 747-762 (1999)

Tracy, et al., Science 254:470-474 (19—)

Li, Y. King, M. A. and Meyer, E. M. "alpha7 nicotinic receptor-mediated protection against ethanol-induced oxidative stress and cytotoxicity in PC12 cells" Brain Res, 861:165-167, Apr. 7, 2000.

Kerjaschki, D., Regele, H. M., Moosberger, I., Nagy-Bojarski, K., Watschinger, B., Soleiman, A., Birner, P., Krieger, S., Hovorka, A., Silberhumer, G., Laakkonen, P., Petrova, T., Langer, B. and Raab, I., "Lymp[hatic neoangiogenesis in human kidney transplants is associated with immunologically active lymphocytic infiltrates", J. Am. Soc. Nephrol. 15:603-612 (2004).

Uspenskaia, O., Liebetrau, M., Hermis, J., Danek, A. and Hamann, G. F., "Aging is associated with increased collagen type IV accumulation in the basal lamina of human cerebral microvessels", BMC Neuroscience, 5:37, (2004).

Flores, C. M., Rogers, S. W., Pabreza, L. A., Wolfe, V. B. and Kellar, K. L. "A subtype of nicotinic cholinergic receptor in rat brain is composed of α4 and β2 subunits and is up-regulated by chronic nicotine treatment" Mol Pharmacol. 41:31-37 (1992).

Marks, M. J. and Collins, A. C. "Characterization of nicotine binding in mouse brain and comparison with the binding of alpha-bungarotoxin and quinuclidinyl benzylate", Mol Pharmacol. 22:554-564 (1982).

Kern, W. R., Mahnir, V. M., Prokai, L., Papke, R. M., Cao, X. F., LeFrancois, S., Wildeboer, K., Porter-Papke, J., Prokai-Tatrai, K., and Soti, F. (2004). Hydroxy metabolites of the Alzheimer's drug candidate DMXBA (GTS-21): Their interactions with brain nicotinic receptors, and brain penetration. Mol. Pharmacol. 65: 56-67.

Zoltewicz, J. A., Bloom, L. B. and Kem. W. R. (1989) Quantitative determination of the ring-chain hydrolysis equilibrium constant for anabaseine and related tobacco alkaloids. J. Org. Chem. 54, 4462-4468.

Zoltewicz J A, Prokai-Tatrai K, Bloom L B and Kem W R (1993) Long range transmission of polar effects of cholinergic 3-arylideneanabaseines. Conformations calculated by molecular modelling. Heterocycles 35, 171-179.

Kem, W. R. (1973) Biochemistry of Nemertine Toxins, In: *Marine Pharmacognosy: Marine Biotoxins as Probes of Cellular Function*. (Martin, D. F. and Padilla, G. M., Eds.). Monographs on Cell Biology Series, Academic Press, NY, Ch. II, pp. 37-84.

Kern, W. R. (1971) A study of the occurrence of anabaseine in Paranemertes and other nemertines. Toxicon 9, 23-32.

Kem W R, Mahnir V M, Papke R L and Lingle C (1997) Anabaseine is a potent agonist upon muscle and neuronal alpha-bungarotoxin sensitive nicotinic receptors. J. Pharmacol. Exper. Therap. 283, 979-992.

Kitagawa, H., Takenouchi, T., Azuma, A., Wesnes, K., Kramer, W. G., and Clody, D. E., and Burnett, A. L. (2003) Safety, pharmacokinetics, and effects on cognitive function of multiple doses of GTS-21 in healthy, male volunteers. Neuropsychopharmacol. 28: 542-551.

Li, Y., Meyer, W. M., Walker, D. W., Millard, W. J., He, Y. J., and King, M. A. (2002) Alpha7 nicotinic receptor activation inhibits ethanol-induced mitochondrial dysfunction, cytochrome c release and neurotoxicity in primary rat hippocampal neuronal cultures. J. Neurochem. 81: 853-858.

Stokes C, Porter-Papke, Horenstein, Kern, McCormack and Papke R L (2004) The structural basis for GTS-21 selectivity between human and rat nicotinic alpha7 receptors. Mol. Pharmacol. 66, 14-24.

Olincy A, Harris, Johnson, Pender, Kongs, Allensworth, Ellis, Zerbe, Leonard, Stevens, Stevens, Martin, Adler, Soti, Kem and Freedman, R. An alpha7 nicotinic cholinergic agonist enhances cognitive function in schizophrenia. Arch. Gen. Psychiatr. (in press).

Radcliffe, K. A., and Dani, J. A. 1998. Nicotinic stimulation produces multiple forms of increased glutamatergic synaptic transmission. J. Neurosci. 18:7075-83.

Picciotto, M. R., Zoli, M., Lena, C. Bessis, A., Lallemand, Y., LeNovere, N., Vincent, P., Pich, E M., Brulet, P., and Changeux, J. P. 1995. Abnormal avoidance learning in mice lacking functional high-affintiy nicotine receptor in the brain. Nature, 374:65-7.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:
1. A 3-benzylidene-anabaseine of the formula:

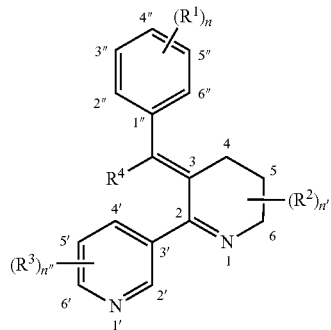

where $R^1$ is, independently, acetoxy, acetamido, amino, dimethylcarbamoyl, diethylcarbamoyl, methylcarbamoyl, ethylcarbamoyl, difluoromethoxy, diethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino or thiomethoxy and n is 0-5; $R^2$ is independently $C_1$-$C_3$ alkyl and n' is 1, wherein at least one $R^2$ is present at position 4, 5, or 6; $R^3$ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; $R^4$ is hydrogen or $C_1$-$C_3$ alkyl or $C_1$-$C_3$ alkylhydroxy; or a pharmaceutically acceptable salt, clathrate, stereoisomer, enantiomer, or combination thereof.

2. The 3-benzylidene-anabaseine of claim 1, wherein $R^1$ is, independently, hydroxy, amino, methylamino, thiomethoxy, or methoxy.

3. The 3-benzylidene-anabaseine of claim 2, wherein each $R^1$ is methoxy.

4. The 3-benzylidene-anabaseine of claim 1, wherein $R^1$ is at the 2" and 4" positions.

5. The 3-benzylidene-anabaseine of claim 1, wherein n is 1 and $R^1$ is at the 4" position.

6. The 3-benzylidene-anabaseine of claim 1, wherein the 3-benzylidene-anabaseine is a α7 nicotinic receptor agonist.

7. The 3-benzylidene-anabaseine of claim 1, wherein the 3-benzylidene-anabaseine is a α7 nicotinic receptor antagonist.

8. A 3-benzylidene-glucuronide-anabaseine of the formula:

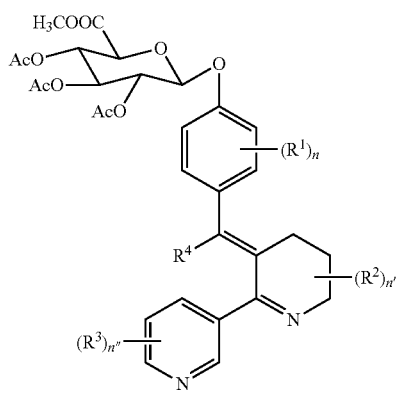

where R¹ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino, acylated glucuronidyl, or thiomethoxy and n is 1; R² is independently $C_1$-$C_3$ alkyl and n' is 0-3; R³ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; R⁴ is hydrogen, $C_1$-$C_3$ alkyl or $C_1$-$C_3$ alkylhydroxy; or a pharmaceutically acceptable salt, clathrate, stereoisomer, enantiomer, or combination thereof.

9. The 3-benzylidene-glucuronide-anabaseine of claim 8, wherein the anabaseine is a α7 nicotinic receptor agonist.

10. The 3-benzylidene-glucuronide-anabaseine of claim 8 wherein the anabaseine is a α7 nicotinic receptor antagonist.

11. The 3-benzylidene-anabaseine of claim 1, wherein n" is 1 and R³ is $C_1$-$C_3$ alkyl.

12. The 3-benzylidene-anabaseine of claim 11, wherein R³ is methyl.

13. The 3-benzylidene-anabaseine of claim 11, wherein R³ is 4'-methyl.

14. The 3-benzylidene-anabaseine of claim 1, wherein the said 3-benzylidene-anabaseine is enriched in one enantiomer and shows greater selectivity for the α7 nicotinic receptor versus the α4β2 nicotinic receptor when compared to the other enantiomer of the 3-benzylidiene-anabaseine.

15. The 3-benzylidene-anabaseine of claim 1, wherein the said 3-benzylidene-anabaseine is enriched in one enantiomer and shows greater selectivity for the α7 nicotinic receptor versus the α4β2 nicotinic receptor when compared to the racemic mixture of the 3-benzylidiene-anabaseine.

16. The 3-benzylidene-anabaseine of claim 1, wherein R² is methyl or ethyl.

17. The 3-benzylidene-anabaseine of claim 1, wherein R² is 4-methyl.

18. The 3-benzylidene-anabaseine of claim 1, wherein R² is 5-methyl.

19. The 3-benzylidene-anabaseine of claim 1, wherein R² is 6-methyl.

20. The 3-benzylidene-anabaseine of claim 1, wherein R² is 6-ethyl.

21. The 3-benzylidene-anabaseine of claim 1, wherein R² is 4-(R)-methyl.

22. The 3-benzylidene-anabaseine of claim 1, wherein R² is 5-(R)-methyl.

23. The 3-benzylidene-anabaseine of claim 1, wherein R² is 6-(S)-methyl.

24. The 3-benzylidene-anabaseine of claim 1, wherein R² is 6-(S)-ethyl.

25. The 3-benzylidene-glucuronide-anabaseine of claim 8, wherein R¹ is $C_1$-$C_3$ alkoxy.

26. The 3-benzylidene-glucuronide-anabaseine of claim 8, wherein R¹ is methoxy.

27. The 3-benzylidene-glucuronide-anabaseine of claim 8, wherein R¹ is 2"-methoxy.

28. A 3-benzylidene-glucuronide-anabaseine of the formula:

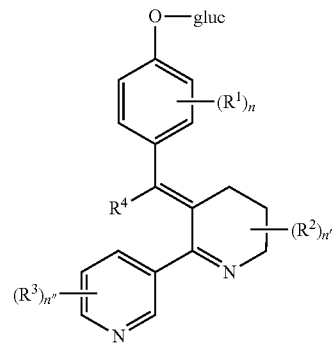

where R¹ is, independently, acetoxy, acetamido, amino, dimethylcarbamoyl, diethylcarbamoyl, methylcarbamoyl, ethylcarbamoyl, difluoromethoxy, dimethylaminopropoxy, trimethylammoniumpropoxy, trimethylammoniumpentoxy, $C_1$-$C_3$ alkyl, $C_1$-$C_3$ alkylhydroxy, hydroxyl, $C_1$-$C_3$ alkoxy, trifluoromethoxy, methylamino, acylated glucuronidyl, or thiomethoxy and n is 0-4; R² is independently $C_1$-$C_3$ alkyl and n' is 0-3; R³ is independently $C_1$-$C_3$ alkyl, $C_1$-$C_3$ alkylhydroxy, $C_1$-$C_3$ alkoxy, cyano, halo, phenoxy, phenyl, pyridyl or benzyl and n" is 0-4; R⁴ is hydrogen, $C_1$-$C_3$ alkyl or $C_1$-$C_3$ alkylhydroxy; gluc is glucuronidyl optionally esterified with a $C_1$-$C_4$ alkylhydroxy and where the glucuronidyl hydroxy groups can be acylated with a $C_1$-$C_3$ acyl group; or a pharmaceutically acceptable salt, clathrate, stereoisomer, enantiomer, or combination thereof.

29. The 3-benzylidene-glucuronide-anabaseine of claim 28, wherein R¹ is $C_1$-$C_3$ alkoxy.

30. The 3-benzylidene-glucuronide-anabaseine of claim 28, wherein R¹ is methoxy.

31. The 3-benzylidene-glucuronide-anabaseine of claim 28, wherein R¹ is 2"-methoxy.

32. A method of selectively stimulating alpha7 nicotinic receptors, comprising the step (a) administering a therapeutically effective amount of a 3-benzylidene-anabaseine of claim 6 to an individual in need thereof.

33. A method of selectively stimulating alpha7 nicotinic receptors, comprising the step (a) administering a therapeutically effective amount of a benzylidene-glucuronide-anabaseine of claim 9 to an individual in need thereof.

34. A method of selectively inhibiting alpha7 nicotinic receptors, comprising the step (a) administering a therapeutically effective amount of a 3-benzylidene-anabaseine of claim 7 to an individual in need thereof.

35. A method of selectively inhibiting alpha7 nicotinic receptors, comprising the step (a) administering a therapeutically effective amount of a benzylidene-glucuronide-anabaseine of claim 10 to an individual in need thereof.

36. A pharmaceutically acceptable composition comprising at least one of the-3-benzylidene anabaseines of claim 1 and one or more pharmaceutically acceptable carriers, excipients, diluents, stabilizers or preservatives.

37. A pharmaceutically acceptable composition comprising at least one of the 3-benzylidene-glucuronide-anabaseine of claim 8 and one or more pharmaceutically acceptable carriers, excipients, diluents, stabilizers or preservatives.

* * * * *